(12) United States Patent
Merwin et al.

(10) Patent No.: US 11,842,798 B2
(45) Date of Patent: Dec. 12, 2023

US011842798B2

(54) NATURAL PRODUCT AND GENETIC DATA ANALYSIS AND DISCOVERY SYSTEM, METHOD AND COMPUTATIONAL PLATFORM THEREFOR

(71) Applicant: Adapsyn Bioscience Inc., Hamilton (CA)

(72) Inventors: Nishanth Merwin, Brampton (CA); Chris DeJong, Hamilton (CA); Chad Johnston, Boston, MA (US); Gregory Chen, Thornhill (CA); Haoxin Li, Hamilton (CA); Michael Skinnider, Vancouver (CA); McLean Edwards, Hillsburgh (CA); Nathan Magarvey, Oakville (CA); Phil Rees, Toronto (CA)

(73) Assignee: Adapsyn Bioscience Inc., Hamilton (CA)

( * ) Notice: Subject to any disclaimer, the term of this patent is extended or adjusted under 35 U.S.C. 154(b) by 1462 days.

(21) Appl. No.: 16/062,075

(22) PCT Filed: Dec. 14, 2016

(86) PCT No.: PCT/CA2016/051472
§ 371 (c)(1),
(2) Date: Jun. 13, 2018

(87) PCT Pub. No.: WO2017/100917
PCT Pub. Date: Jun. 22, 2017

(65) Prior Publication Data
US 2018/0373833 A1  Dec. 27, 2018

Related U.S. Application Data

(60) Provisional application No. 62/359,803, filed on Jul. 8, 2016, provisional application No. 62/359,795, filed on Jul. 8, 2016, provisional application No. 62/266,865, filed on Dec. 14, 2015.

(51) Int. Cl.
| | |
|---|---|
| *G16B 5/20* | (2019.01) |
| *G16B 5/00* | (2019.01) |
| *G16B 15/00* | (2019.01) |
| *G16B 20/00* | (2019.01) |
| *G16B 40/00* | (2019.01) |
| *C12Q 1/68* | (2018.01) |
| *C12N 15/10* | (2006.01) |
| *G16B 99/00* | (2019.01) |
| *G16B 20/50* | (2019.01) |
| *G16B 40/10* | (2019.01) |
| *G16B 20/20* | (2019.01) |
| *G16B 20/30* | (2019.01) |

(52) U.S. Cl.
CPC ............... *G16B 5/20* (2019.02); *C12N 15/10* (2013.01); *C12N 15/1089* (2013.01); *C12Q 1/68* (2013.01); *G16B 5/00* (2019.02); *G16B 15/00* (2019.02); *G16B 20/00* (2019.02); *G16B 20/20* (2019.02); *G16B 20/30* (2019.02); *G16B 20/50* (2019.02); *G16B 40/00* (2019.02); *G16B 40/10* (2019.02); *G16B 99/00* (2019.02)

(58) Field of Classification Search
None
See application file for complete search history.

(56) References Cited

U.S. PATENT DOCUMENTS

2015/0148242 A1    5/2015   Magarvey et al.

FOREIGN PATENT DOCUMENTS

WO        2013181758 A1    12/2013

OTHER PUBLICATIONS

Eddy, S.R. Accelerated Profile HMM Searches. PLoS Comput Biol 7, e1002195. (2011).
Edgar R.C. Muscle: multiple sequence alignment with high accuracy and high throughput. Nucleic Acids Res 32, 1792-1797 (2004).
Engelhardt, K., Degnes, K.F. and Zotchev, S.B. (2010) Isolation and characterization of the gene cluster for biosynthesis of the thiopeptide antibiotic TP-1161. Appl Environ Microbiol, 76, 7093-7101.
Finn, R.D., Clements, J. & Eddy, S.R. Hmmer web server: interactive sequence similarity searching. Nucleic Acids Res 39, W29-37 (2011).
Fischbach, M. A. & Walsh, C. T. Antibiotics for emerging pathogens. Science 325, 1089-1093 (2009).
Fischbach, M.A. & Clardy, J. One pathway, many products. Nature Chemical Biology 3, 353-355 (2007).
Fischbach, M.A. & Walsh, C.T. Assembly-line enzymology for polyketide and nonribosomal peptide antibiotics: Logic, machinery, and mechanisms. Chem Rev 106, 3468-3496 (2006).
Arnison, P.G., Bibb, M.J., Bierbaum, G., Bowers, A.A., Bugni, T.S., Bulaj, G., Camarero, J.A., Campopiano, D.J., Challis, G.L., Clardy, J. et al. (2013) Ribosomally synthesized and post-translationally modified peptide natural products: overview and recommendations for a universal nomenclature. Nat Prod Rep, 30, 108-160.

(Continued)

*Primary Examiner* — G. Steven Vanni
(74) *Attorney, Agent, or Firm* — Knobbe, Martens, Olson & Bear, LLP

(57) ABSTRACT

A method for linking a natural product and gene cluster is disclosed. In some embodiments, monomers of natural products are predicted from a gene sequence. In other embodiments, monomers of natural products are predicted from a chemical structure of a natural product. In another embodiment, monomers predicted from gene sequences are aligned with monomers predicted from chemical structures.

15 Claims, 56 Drawing Sheets

Specification includes a Sequence Listing.

(56) References Cited

OTHER PUBLICATIONS

Fisher, R.A.Y., Frank Statistical tables for biological, agricultural and medical research (3rd ed.). (Oliver & Boyd, London; 1948).
Fluhe, L., Burghaus, O., Wieckowski, B.M., Giessen, T.W., Linne, U. and Marahiel, M.A. (2013) Two [4Fe-4S] clusters containing radical SAM enzyme SkfB catalyze thioether bond formation during the maturation of the sporulation killing factor. J Am Chem Soc, 135, 959-962.
Fluhe, L., Knappe, T.A., Gattner, M.J., Schafer, A., Burghaus, O., Linne, U. and Marahiel, M.A. (2012) The radical SAM enzyme AlbA catalyzes thioether bond formation in subtilosin A. Nat Chem Biol, 8, 350-357.
Forsberg, K.J. et al. The shared antibiotic resistome of soil bacteria and human pathogens. Science 337, 1107-1111 (2012).
Foulston, L.C. and Bibb, M.J. (2010) Microbisporicin gene cluster reveals unusual features of lantibiotic biosynthesis in actinomycetes. Proc Natl Acad Sci U S A, 107, 13461-13466.
Freeman, M.F., Gurgui, C., Helf, M.J., Morinaka, B.I., Uria, A.R., Oldham, N.J., Sahl, H.G., Matsunaga, S. and Piel, J. (2012) Metagenome mining reveals polytheonamides as posttranslationally modified ribosomal peptides. Science, 338, 387-390.
Fu, C. et al. Biosynthetic studies of telomycin reveal new lipopeptides with enhanced activity. J. Am. Chem. Soc. 137, 7692-7705 (2015).
Garcia De Gonzalo, C.V., Zhu, L., Oman, T.J. and van der Donk, W.A. (2014) NMR structure of the S-linked glycopeptide sublancin 168. ACS Chem Biol, 9, 796-801.
Gaudiano, G., Bravo, P. & Qiulico, A. The structure of lucensomycin from Streptomyces lucensis. I. Tetrahedron Lett 30, 3559-3565 (1966).
Gibson, M.K., Forsberg, K.J. & Dantas, G. Improved annotation of antibiotic resistance determinants reveals microbial resistomes cluster by ecology. ISME J. 9, 207-216 (2015).
Bachmann, B.O. & Ravel, J. in Methods in Enzymology, vol. vol. 458 181-217 (Academic Press, 2009).
Goss, R.J.M., Shankar, S. & Fayad, A.A. The generation of "unNatural" products: Synthetic biology meets synthetic chemistry. Nat. Prod. Rep. 29, 870-889 (2012).
Gourevitch, A. et al. Microbiological studies on telomycin. Antibiot. Annu. 856-862, (1957-1958).
Hadjithomas, M. et al. IMG-ABC: A knowledge base to fuel discovery of biosynthetic gene clusters and novel secondary metabolites. mBio 6, e00932-15 (2015).
Haft, D.H., Basu, M.K. and Mitchell, D.A. (2010) Expansion of ribosomally produced natural products: a nitrile hydratase- and Nif11-related precursor family. BMC Biol, 8, 70.
Hamamoto, H. et al. Lysocin E is a new antibiotic that targets menaquinone in the bacterial membrane. Nat. Chem. Biol. 11, 127-133 (2015).
Hayashi, S., Ozaki, T., Asamizu, S., Ikeda, H., Omura, S., Oku, N., Igarashi, Y., Tomoda, H. and Onaka, H. (2014) Genome mining reveals a minimum gene set for the biosynthesis of 32-membered macrocyclic thiopeptides lactazoles. Chem Biol, 21, 679-688.
Hertweck, C. The Biosynthetic Logic of Polyketide Diversity. Angew Chem Int Edit 48, 4688-4716 (2009).
Huang, E. and Yousef, A.E. (2015) Biosynthesis of paenibacillin, a lantibiotic with N-terminal acetylation, by Paenibacillus polymyxa. Microbiol Res, 181, 15-21.
Huo, L., Rachid, S., Stadler, M., Wenzel, S.C. and Muller, R. (2012) Synthetic biotechnology to study and engineer ribosomal bottromycin biosynthesis. Chem Biol, 19, 1278-1287.
Huson, D.H. & Scornavacca, C. Dendroscope 3: An interactive tool for rooted phylogenetic trees and networks. Syst. Biol. 61, 1061-1067 (2012).
Bachmann, B.O. Biosynthesis: Is it time to go retro? Nature Chemical Biology 6, 390-393 (2010).
Ishida, K., Lincke, T., Behnken, S. & Hertweck, C. Induced Biosynthesis of Cryptic Polyketide Metabolites in a Burkholderia thailandensis Quorum Sensing Mutant. Journal of the American Chemical Society 132, 13966-13968 (2010).
Ivanitskaia, L.P., et al. Use of selective media with lincomycin for the directed screening of antibiotic producers. (Original in Russian.) Antibiotiki 26, 83-86 (1981) (Abtract (Retrieved Oct. 2, 2019).
Jensen, P.R., Chavarria, K.L., Fenical, W., Moore, B.S. & Ziemert, N. Challenges and triumphs to genomics-based natural product discovery J Ind Microbiol Biot 41, 203-209 (2014).
Jian, X.H., Pan, H.X., Ning, T.T., Shi, Y.Y., Chen, Y.S., Li, Y., Zeng, X.W., Xu, J. and Tang, G.L. (2012) Analysis of YM-216391 biosynthetic gene cluster and improvement of the cyclopeptide production in a heterologous host. ACS Chem Biol, 7, 646-651.
Kawai, F. et al. Cardiolipin domains in Bacillus subtilis Marburg membranes. Journal of Bacteriology vol. 186.5, 1475-1483 (2004).
Keller, S. et al. Action of atrop-abyssomicin C as an inhibitor of 4-amino-4-deoxychorismate synthase PabB. Angew Chem Int Ed Engl. 46, 8284-8286 (2007).
Khayatt, B.I., Overmars, L., Siezen, R.J. & Francke, C. Classification of the Adenylation and Acyl-Transferase Activity of NRPS and PKS Systems Using Ensembles of Substrate Specific Hidden Markov Models. Plos One 8 (2013).
Koch, M.A. et al. Charting biologically relevant chemical space: a structural classification of natural products (SCONP). Proc. Natl. Acad. Sci. USA. 102, 17272-17277 (2005).
Leikoski, N., Liu, L., Jokela, J., Wahlsten, M., Gugger, M., Calteau, A., Permi, P., Kerfeld, C.A., Sivonen, K. and Fewer, D.P. (2013) Genome mining expands the chemical diversity of the cyanobactin family to include highly modified linear peptides. Chem Biol, 20, 1033-1043.
Bacon Schneider, K., Palmer, T.M. and Grossman, A.D. (2002) Characterization of comQ and comX, two genes required for production of ComX pheromone in Bacillus subtilis. J Bacteriol, 184, 410-419.
Li, B., Sher, D., Kelly, L., Shi, Y., Huang, K., Knerr, P.J., Joewono, I., Rusch, D., Chisholm, S.W. and van der Donk, W.A. (2010) Catalytic promiscuity in the biosynthesis of cyclic peptide secondary metabolites in planktonic marine cyanobacteria. Proc Natl Acad Sci U S A, 107, 10430-10435.
Li, J.W. & Vederas, J.C. Drug discovery and natural products: end of an era or an endless frontier? Science 325, 161-50 (2009).
Liao, R., Duan, L., Lei, C., Pan, H., Ding, Y., Zhang, Q., Chen, D., Shen, B., Yu, Y. and Liu, W. (2009) Thiopeptide biosynthesis featuring ribosomally synthesized precursor peptides and conserved posttranslational modifications. Chem Biol, 16, 141-147.
Lin, A.H. et al. The oxazolidinone eperezolid binds to the 50S ribosomal subunit and competes with binding of chloramphenicol and lincomycin. Antimicrob. Agents Chemother. 41, 2127-2131 (1997).
Lincke, T., Behnken, S., Ishida, K., Roth, M. & Hertweck, C. Closthioamide: An Unprecedented Polythioamide Antibiotic from the Strictly Anaerobic Bacterium Clostridium cellulolyticum. Angew Chem Int Edit 49, 2011-2013 (2010).
Ling, L.L. et al. A new antibiotic kills pathogens without detectable resistance. Nature 517, 455-459 (2015).
Machaidze, G., Ziegler, A. & Seelig, J. Specific binding of Ro 09-0198 (cinnamycin) to phosphatidylethanoloamine: a thermodynamic analysis. Biochemistry 41, 1965-1971 (2002).
Magrane, M. & Consortium, U. UniProt Knowledgebase: a hub of integrated protein data. Database (Oxford), bar009. (2011).
Maksimov, M.O., Pelczer, I. and Link, A.J. (2012) Precursor-centric genome-mining approach for lasso peptide discovery. Proc Natl Acad Sci U S A, 109, 15223-15228.
Malcolmson, S.J., Young, T.S., Ruby, J.G., Skewes-Cox, P. and Walsh, C.T. (2013) The posttranslational modification cascade to the thiopeptide berninamycin generates linear forms and altered macrocyclic scaffolds. Proc Natl Acad Sci U S A, 110, 8483-8488.
Johnston, C.W. et al. "An automated Genomes-to-Natural Products platform (GNP) for the discovery of modular natural products" Nat Commun 6 (2015).
Micallef et al. "Genome mining for natural product biosynthetic gene clusters in the Subsection V cyanobacteria", BMC Genomics, vol. 16, No. 1, Sep. 3, 2015.
Skinnider et al. "Genomic charting of ribosomally synthesized natural product chemical space facilitates targeted mining", Pro-

(56) References Cited

OTHER PUBLICATIONS ceedings of the National Academy of Sciences of the United States of America, vol. 113, No. 42, Oct. 3, 2016), pp. E6343-E6351.
Skinnider, M.A. et al. "Genomes to natural products PRediction Informatics for Secondary Metabolomes (PRISM)" Nucleic Acids Res (2015) 43: 9645-9662.
Supplemental Partial European Search Report for corresponding application EP 16 87 4195, dated Apr. 4, 2019 (20 pages).
Walsh et al. "Natural Products Version 2.0: Connecting Genes to Molecules", Journal of the American Chemical Society, vol. 132, No. 8, Mar. 3, 2010, pp. 2469-2493.
Weber T et al. "CLUSEAN: A computer-based framework for the automated analysis of bacterial secondary metabolite biosynthetic gene clusters", Journal of Biotechnology, Elsevier Amsterdam, NL, vol. 140, No. 1-2, Mar. 10, 2009, pp. 13-17.
Courtesy Letter from Canadian Intellectual Property Office—Acknowledgement of Prior Art to Agent dated Jun. 18, 2021 (3 Pages).
Mohimani, Hosein, et al., "Cycloquest: Identification of Cyclopeptides via Database Search of their Mass Spectra against Genome Databases" J. Proteome Res., 10(10); pp. 4505-4512 (2011).
Third Party Prior Art submission un Section 34.1 of the Canadian Patent Act run respect of Canadian Patent Application SN: 3008, 183 2021 (2 pages).
Mohimani, Hosein, et al., "Automated Genome Mining of Ribosomal Peptide Natural Products", ACS Chem. Biol. vol. 9, pp. 1545-1551 (2014).
Mohimani, Hosein, et al., "NRPquest: Coupling Mass Spectrometry and Genome Mining for Nonribosomal Peptide Discovery", J. Nat. Prod. vol. 77, 1902-1909 (2014).
Third Party Observation in European Patent Application No. EP20160874195 issued May 15, 2021.
Altschul, S.F. et al. Gapped BLAST and PSI-BLAST: a new generation of protein database search programs. Nucleic Acids Res 25, 3389-3402 (1997).
Schneider, C.A., Rasband, W.S. & Eliceiri, K.W. NIH Image to ImageJ: 25 years of image analysis. Nat. Meth. 9, 671-675 (2012).
Schramma, K.R., Bushin, L.B. and Seyedsayamdost, M.R. (2015) Structure and biosynthesis of a macrocyclic peptide containing an unprecedented lysine-to-tryptophan crosslink. Nat Chem, 7, 431-437.
Skinnider, M.A. et al. Genomes to natural products PRediction Informatics for Secondary Metabolomes (PRISM). Nucleic Acids Res. 43, 9645-9662 (2015).
Smith, T.F. & Waterman, M.S. Identification of Common Molecular Subsequences. J Mol Biol 147, 195-197 (1981).
Srivastava, A. et al. New target for inhibition of bacterial RNA polymerase: 'switch region'. Curr. Opin. Microbiol. 14, 532-543 (2011).
Steinbeck, C. et al. Recent developments of the Chemistry Development Kit (CDK)—An open-source Java library for chemo- and bioinformatics. Feb. 28, 2005 1-24.
Steinbeck, C. et al. The Chemistry Development Kit (CDK): an open-source Java library for Chemo- and Bioinformatics. J Chem Inf Comput Sci 43, 493-500 (2003).
Thaker, M.N. et al. Identifying producers of antibacterial compounds by screening for antibiotic resistance. Nat. Biotechnol. 31, 922-927 (2013).
Bérdy, J. Thoughts and facts about antibiotics: Where we are now and where we are heading. J. Antibiot. 65, 385-395 (2012).
Tisch, D.E., Huftalen, J.B. & Dickson, H.L. Pharmacological studies with telomycin. Antibiot. Annu. 863-868, (1957-1958).
Tocchetti, A., Maffioli, S., Iorio, M., Alt, S., Mazzei, E., Brunati, C., Sosio, M. and Donadio, S. (2013) Capturing linear intermediates and C-terminal variants during maturation of the thiopeptide GE2270. Chem Biol, 20, 1067-1077.
Tsai, M. et al. *Staphylococcus aureus* requires cardiolipin for survival under conditions of high salinity. BMC Microbiol. 11, 1471-2180-11-13 (2011).

Van Belkum, M.J., Martin-Visscher, L.A. and Vederas, J.C. (2011) Structure and genetics of circular bacteriocins. Trends Microbiol, 19, 411-418.
Vining, L.C. Roles of secondary metabolites from microbes. Ciba Foundation Symposium 171—Secondary Metabolites: their Function and Evolution. (1992).
Vizcaino, M.I. & Crawford, J.M. The colibactin warhead crosslinks DNA. Nat Chem 7, 411-417 (2015).
Walsh, C.T. & Wencewicz, T.A. Prospects for new antibiotics: a molecule-centered perspective. J. Antibiot. 67, 7-22 (2014).
Walsh, C.T., Brien, R.V.O. & Khosla, C. Nonproteinogenic Amino Acid Building Blocks for Nonribosomal Peptide and Hybrid Polyketide Scaffolds. Angew Chem Int Edit 52, 7098-7124 (2013).
Wang, J., Yu, Y., Tang, K., Liu, W., He, X., Huang, X. and Deng, Z. (2010) Identification and analysis of the biosynthetic gene cluster encoding the thiopeptide antibiotic cyclothiazomycin in Streptomyces hygroscopicus 10-22. Appl Environ Microbiol, 76, 2335-2344.
Watrous, J. et al. Mass spectral molecular networking of living microbial colonies. P Natl Acad Sci USA 109, E1743-E1752 (2012).
Bibikova, M.V., Ivanitskaia, L.P. & Singal, E.M. Directed screening of aminoglycoside antibiotic producers on selective media with gentamycin. (Original in Russian.) Antibiotiki 26, 488-492 (1981) (Abstract—retrieved Oct. 2, 2019).
Weber, T. et al. antiSMASH 3.0—a comprehensive resource for the genome mining of biosynthetic gene clusters. Nucl. Acids Res. 43, W237-W243 (2015).
Wieland Brown, L.C., Acker, M.G., Clardy, J., Walsh, C.T. and Fischbach, M.A. (2009) Thirteen posttranslational modifications convert a 14-residue peptide into the antibiotic thiocillin. Proc Natl Acad Sci U S A, 106, 2549-2553.
Wilson D.N. Ribosome-targeting antibiotics and mechanisms of bacterial resistance. Nat. Rev. Microbiol. 12, 35-48 (2014).
Wuster, A. and Babu, M.M. (2008) Conservation and evolutionary dynamics of the agr cell-to-cell communication system across firmicutes. J Bacteriol, 190, 743-746.
Young, T.S. and Walsh, C.T. (2011) Identification of the thiazolyl peptide GE37468 gene cluster from Streptomyces ATCC 55365 and heterologous expression in Streptomyces lividans. Proc Natl Acad Sci U S A, 108, 13053-13058.
Yu, Y., Duan, L., Zhang, Q., Liao, R., Ding, Y., Pan, H., Wendt-Pienkowski, E., Tang, G., Shen, B. and Liu, W. (2009) Nosiheptide biosynthesis featuring a unique indole side ring formation on the characteristic thiopeptide framework. ACS Chem Biol, 4, 855-864.
Yu, Y., Guo, H., Zhang, Q., Duan, L., Ding, Y., Liao, R., Lei, C., Shen, B. and Liu, W. (2010) NosA catalyzing carboxyl-terminal amide formation in nosiheptide maturation via an enamine dealkylation on the serine-extended precursor peptide. J Am Chem Soc, 132, 16324-16326.
Ziemert, N., Ishida, K., Liaimer, A., Hertweck, C. and Dittmann, E. (2008) Ribosomal synthesis of tricyclic depsipeptides in bloom-forming cyanobacteria. Angew Chem Int Ed Engl, 47, 7756-7759.
Boakes, S., Cortes, J., Appleyard, A.N., Rudd, B.A. and Dawson, M.J. (2009) Organization of the genes encoding the biosynthesis of actagardine and engineering of a variant generation system. Mol Microbiol, 72, 1126-1136.
Boucher, H. W. et al. Bad bugs, no drugs: no ESKAPE! an update from the Infectious Diseases Society of America. Clin. Infect. Dis. 48, 1-12 (2009).
Breil, B.T., Ludden, P.W. and Triplett, E.W. (1993) DNA sequence and mutational analysis of genes involved in the production and resistance of the antibiotic peptide trifolitoxin. J Bacteriol, 175, 3693-3702.
Bush, K. et al. Tackling antibiotic resistance. Nature Rev. Microbiol. 9, 894-896 (2011).
Callahan, B., Thattai, M. & Shraiman, B.I. Emergent gene order in a model of modular polyketide synthases. P Natl Acad Sci USA 106, 19410-19415 (2009).
Capella-Gutierrez, S., Silla-Martinez, J.M. and Gabaldon, T. trimAl: a tool for automated alignment trimming in large-scale phylogenetic analyses. Bioinformatics 25, 1972-1973 (2009).
Challis, G.L. & Naismith, J.H. Structural aspects of non-ribosomal peptide biosynthesis. Curr Opin Struc Biol 14, 748-756 (2004).

(56) References Cited

OTHER PUBLICATIONS

Anderson, E.. Veith, G. D.; Weininger, D. Smiles: A Line Notation and Computerized Interpreter for Chemical Structures (United States Environmental Protection Agency, Environmental Research Laboratory, Duluth, MN; 1987) 1-4.
Claesen, J. and Bibb, M. (2010) Genome mining and genetic analysis of cypemycin biosynthesis reveal an unusual class of posttranslationally modified peptides. Proc Natl Acad Sci U S A, 107, 16297-16302.
Cociancich, S. et al. The gyrase inhibitor albicidin consists of p-aminobenzoic acids and cyanoalanine. Nat. Chem. Biol. 11, 195-197 (2015).
Cotter, P.D., O'Connor, P.M., Draper, L.A., Lawton, E.M., Deegan, L.H., Hill, C. and Ross, R.P. (2005) Posttranslational conversion of L-serines to D-alanines is vital for optimal production and activity of the lantibiotic acticin 3147. Proc Natl Acad Sci U S A, 102, 18584-18589.
Cox, C.L., Doroghazi, J.R. and Mitchell, D.A. (2015) The genomic landscape of ribosomal peptides containing thiazole and oxazole heterocycles. BMC Genomics, 16, 778.
Cundliffe, E. & Demain, A.L. Avoidance of suicide in antibiotic-producing microbes. J. Ind. Microbiol. Biotechnol. 37, 643-672 (2010).
D'costa, V.M. et al. Sampling the antibiotic resistome. Science 311, 374-377 (2006).
Desjardine, K. et al. Tauramamide, a lipopeptide antibiotic produced in culture by Brevibacillus laterosporus isolated from a marine habitat: Structure elucidation and synthesis. J Nat Prod 70, 1850-1853 (2007).
Ding, Y., Yu, Y., Pan, H., Guo, H., Li, Y. and Liu, W. (2010) Moving posttranslational modifications forward to biosynthesize the glycosylated thiopeptide nocathiacin I in Nocardia sp. ATCC202099. Mol Biosyst, 6, 1180-1185.
Dobashi, K., Naganawa, H., Takahashi, Y., Takita, T. & Takeuchi, T. Novel antifungal antibiotics octacosamicin A and octacosamicin B. II. The structure elucidation using various NMR spectroscopic methods. J Antibiot 41, 1533-1541 (1988).
Donadio, S. et al. Antibiotic discovery in the twenty-first century: current trends and future perspectives. J. Antibiot. 63, 423-430 (2010).
Arias-Cartin, R. et al. Cardiolipin binding in bacterial respiratory complexes: Structural and functional implications. Biochim Biophys Acta. 1817, 1937-1949 (2012).
Doroghazi, J.R. et al. A roadmap for natural product discovery based on large-scale genomics and metabolomics. Nat Chem Biol 10, 963-968 (2014).
Duan, L., Wang, S., Liao, R. and Liu, W. (2012) Insights into quinaldic acid moiety formation in thiostrepton biosynthesis facilitating fluorinated thiopeptide generation. Chem Biol, 19, 443-448.
Barsby, T., Kelly, M.T., Gagne, S.M. & Andersen, R.J. Bogorol A produced in culture by a marine Bacillus sp. reveals a novel template for cationic peptide antibiotics. Org Lett 3, 437-440 (2001).
Medema, M.H. et al. Minimum Information about a Biosynthetic Gene cluster. Nat Chem Biol 11, 625-631 (2015).
Onaka, H., Nakaho, M., Hayashi, K., Igarashi, Y. and Furumai, T. (2005) Cloning and characterization of the goadsporin biosynthetic gene cluster from Streptomyces sp. TP-A0584. Microbiology, 151, 3923-3933.
Mileykovskaya, E. & Dowhan, W. Cardiolipin membrane domains in prokaryotes and eukaryotes. Biochim Biophys Acta. 1788(10), 2084-2091 (2009).
Misiek, M. et al. Telomycin a new antibiotic. Antibiot. Annu. 852-855, (1957-1958).
Morris, R.P., Leeds, J.A., Naegeli, H.U., Oberer, L., Memmert, K., Weber, E., LaMarche, M.J., Parker, C.N., Burrer, N., Esterow, S. et al. (2009) Ribosomally synthesized thiopeptide antibiotics targeting elongation factor Tu. J Am Chem Soc, 131, 5946-5955.
Nakajima, N. et al. Mycoplanecins, novel antimycobacterial antibiotics from Actinoplanes awajinensis subsp. mycoplanecinus subsp. nov. II. Isolation, physico-chemical characterization and biological activities of mycoplanecin A. J. Antibiot. 36, 961-966 (1983).
Nakao, M. et al. Pyloricidins, novel anti-Helicobacter pylori antibiotics produced by Bacillus sp. I. Taxonomy, fermentation and biological activity. J. Antibiot. 54, 926-933 (2001).
Needleman, S.B. & Wunsch, C.D. A general method applicable to the search for similarities in the amino acid sequence of two proteins. J Mol Biol 48, 443-453 (1970).
Ortega, M.A., Velasquez, J.E., Garg, N., Zhang, Q., Joyce, R.E., Nair, S.K. and van der Donk, W.A. (2014) Substrate specificity of the lanthipeptide peptidase ElxP and the oxidoreductase ElxO. ACS Chem Biol, 9, 1718-1725.
Newman, D.J. & Cragg, G.M. Natural products as a source of new drugs over the 30 years from 1981 to 2010. J. Nat. Prod. 75, 311-335 (2012).
Baumann, S. et al. Cystobactamids: Myxobacterial Topoisomerase Inhibitors Exhibiting Potent Antibacterial Activity. Angew. Chem. Int. Edn. Engl. 53, 14605-14609 (2014).
Okada, M., Sato, I., Cho, S.J., Iwata, H., Nishio, T., Dubnau, D. and Sakagami, Y. (2005) Structure of the *Bacillus subtilis* quorum-sensing peptide pheromone ComX. Nat Chem Biol, 1, 23-24.
Okesli, A., Cooper, L.E., Fogle, E.J. and van der Donk, W.A. (2011) Nine post-translational modifications during the biosynthesis of cinnamycin. J Am Chem Soc, 133, 13753-13760.
Oliva, B. et al. Mode of action of the cyclic depsipeptide antibiotic LL-AO341, and partial characterization of a *Staphylococcus aureus* mutant resistant to the antibiotic. J. Antimicrob. Chemother. 32, 817-830 (1993).
Over, B, et al. Natural-product-derived fragments for fragment-based ligand discovery. Nat. Chem. 5, 21-28 (2013).
Ozaki, T., Kurokawa, Y., Hayashi, S., Oku, N., Asamizu, S., Igarashi, Y. and Onaka, H. (2016) Insights into the Biosynthesis of Dehydroalanines in Goadsporin. Chembiochem, 17, 218-223.
Paradis, E., Claude, J. & Strimmer, K. APE: analyses of phylogenetics and evolution in R language. Bioinformatics 20, 289-290 (2004).
Payne, D.J. et al. Drugs for bad bugs: confronting the challenges of antibacterial discovery. Nat Rev Drug Discov. 6, 29-40 (2007).
Rahman, S.A., Bashton, M., Holliday, G.L., Schrader, R. & Thornton, J.M. Small Molecule Subgraph Detector (SMSD) toolkit. J Cheminformatics 1 (2009).
Rateb, M.E., Zhai, Y., Ehmer, E., Rath, C.M., Wang, X., Tabudravu, J., Ebel, R., Bibb, M., Kyeremeh, K., Dorrestein, P.C. et al. (2015) Legonaridin, a new member of linaridin RiPP from a Ghanaian Streptomyces isolate. Org Biomol Chem, 13, 9585-9592.
Rutledge, P.J. & Challis, G.L. Discovery of microbial natural products by activation of silent biosynthetic gene clusters. Nat Rev Microbiol 13, 509-523 (2015).
Oliver O.M. et al., "Localization of Anionic Phospholipids in *Escherichia coil* Cells" J. Bateriol, vol. 196, No. 19, pp. 386-3398 (2014).
International Search Report in International Application No. PCT/CA2016/051472, dated Mar. 6, 2017.
Written Opinion in International Application No. PCT/CA2016/051472, dated Mar. 6, 2017.
Chris A DeJong et al: "Polyketide and Nonribosomal Peptide Retro-Biosynthesis and Global Gene Cluster Matching", Nature Chemical Biology, vol. 12, No. 12, pp. 1007-1014, Dec. 1, 2016.
Cimerancic Peter et al: "Insights into Secondary Metabolism from a Global Analysis of Prokaryotic Biosynthetic Gene Clusters", Cell, vol. 158, No. 2, pp. 412-421, Jul. 17, 2014.
Jacob Gubbens et al: "Natural Product Proteomining, a Quantitative Proteomics Platform, Allows Rapid Discovery of Biosynthetic Gene Clusters for Different Classes of Natural Products", Chemistry and Biology, vol. 21, No. 1, pp. 707-718, Jun. 1, 2014.
Kai Blin et al: "antiSMASH 2.0—A Versatile Platform for Genome Mining of Secondary Metabolite Producers", Nucleic Acids Research, vol. 41, No. W1, pp. W204-W212, May 21, 2013.
Kai Blin et al: "Improved Lanthipeptide Detection and Prediction for antiSMASH", PLOS ONE, vol. 9, No. 2, pp. e89420, Feb. 20, 2014.
Kazuya Yamanaka et al: "Direct Cloning and Refactoring of a Silent Lipopeptide Biosynthetic Gene Cluster Yields the Antibiotic Taromycin A", PNAS, vol. 111, No. 5, pp. 1957-1962, Jan. 21, 2014.

(56) References Cited

OTHER PUBLICATIONS

Marnix, H. Medema et al: "antiSMASH: Rapid Identification, Annotation and Analysis of Secondary Metabolite Biosynthesis Gene Clusters in Bacterial and Fungal Genome Sequences" Nucliec Acids Research, vol. 39, No. suppl. 2., pp. W339-W346, Jun. 14, 2011.

Myco Umemura et al: "MIDDAS-M Motif-Independent De Novo Detection of Secondary Metabolite Gene Clusters Through the Integration of Genome Sequencing and Transcriptome Data" PLOS ONE, vol. 8, No. 12, pp. 1-10, Jan. 1, 2013.

Tilmann Weber et al: "antiSMASH 3.0—A Comprehensive Resource for the Genome Mining of Biosynthetic Gene Clusters", Nucleic Acids Research, vol. 43, No. W1, pp. W237-W243, May 6, 2015.

Yi-Ming Chiang et al: "Recent Advances in Awakening Silent Biosynthetic Gene Clusters and Linking Orphan Clusters to Natural Products in Mircoorganisms", Current Opinion in Chemical Biology, vol. 15, No. 1, pp. 137-143, Nov. 24, 2010.

Supplementary European Search Report in European Application No. EP 16 87 4195, dated Jul. 16, 2019.

FIG. 9
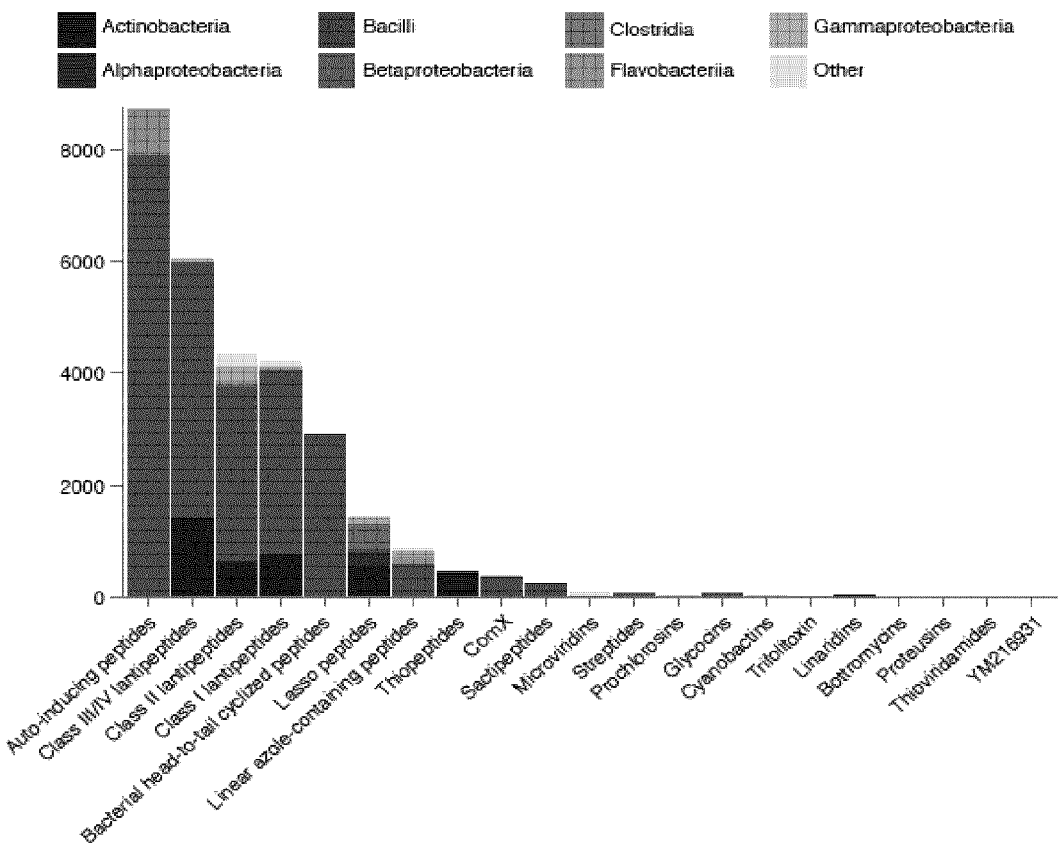
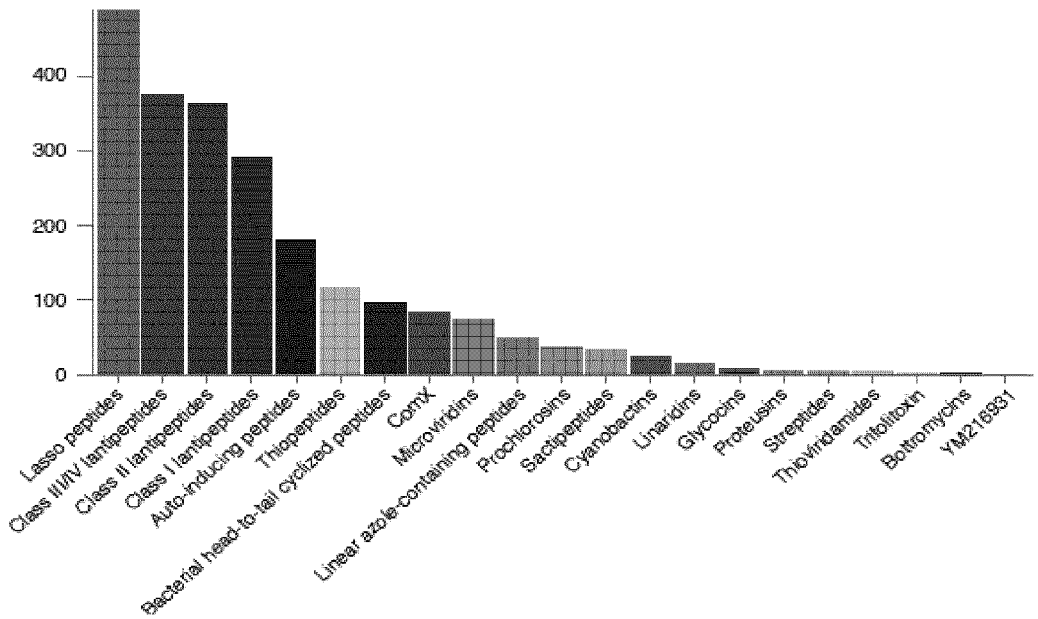

FIG. 16
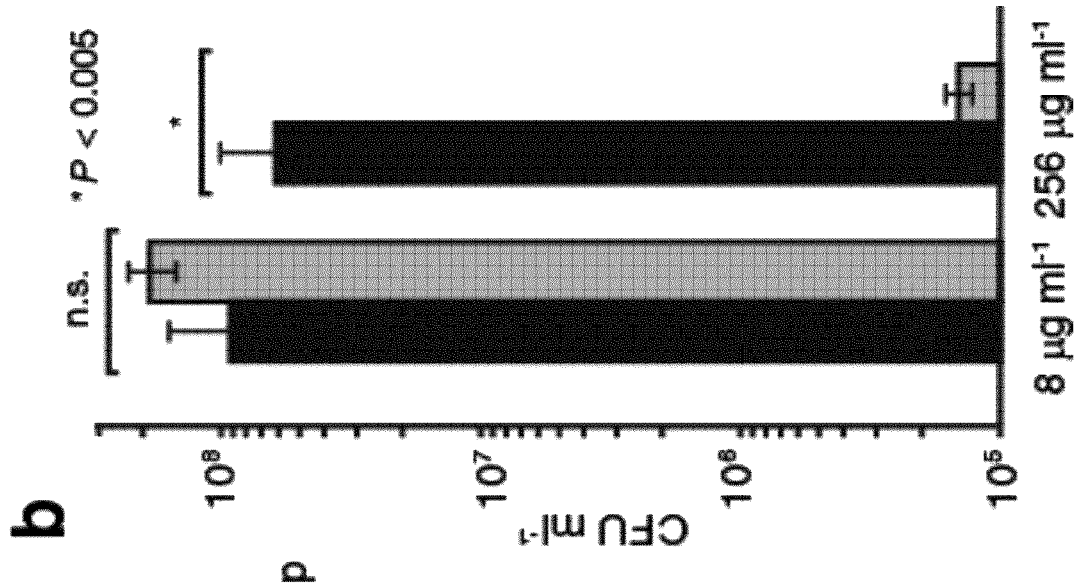
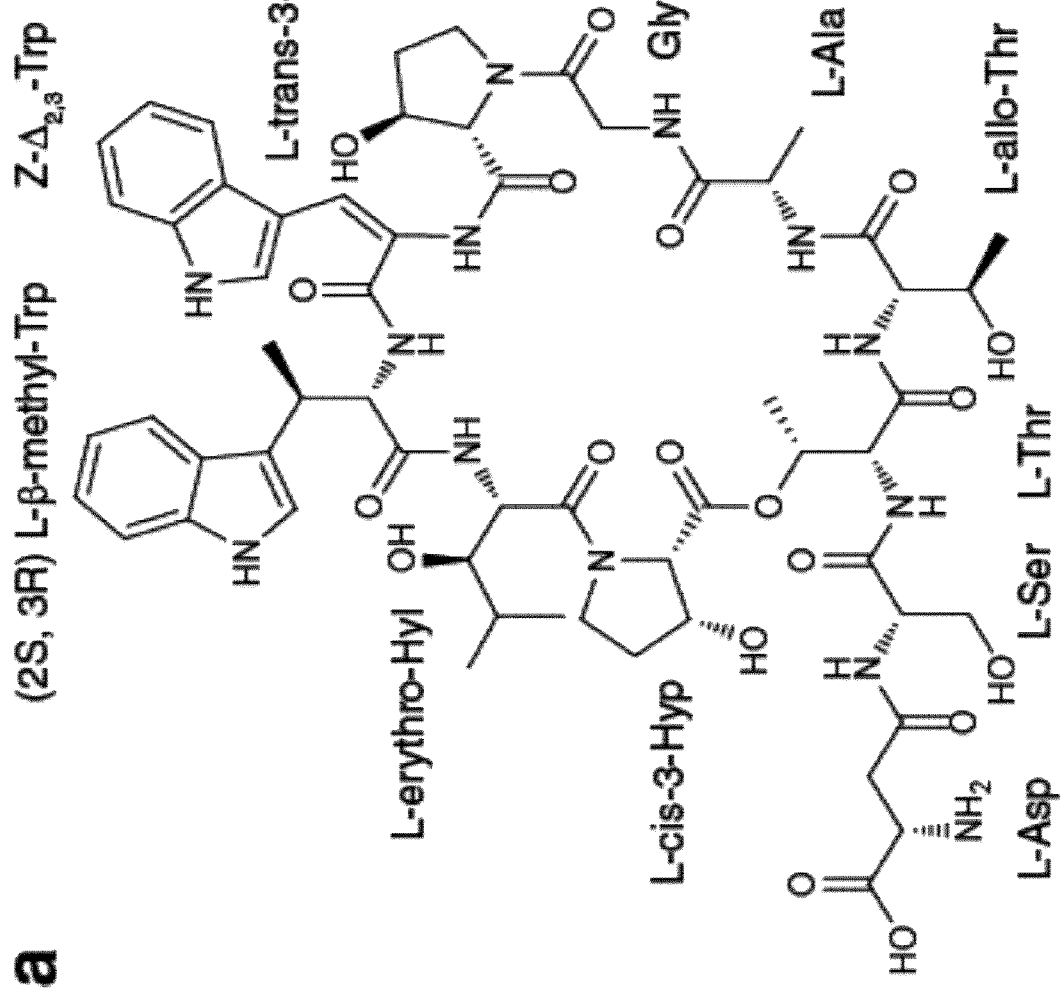

FIG. 19
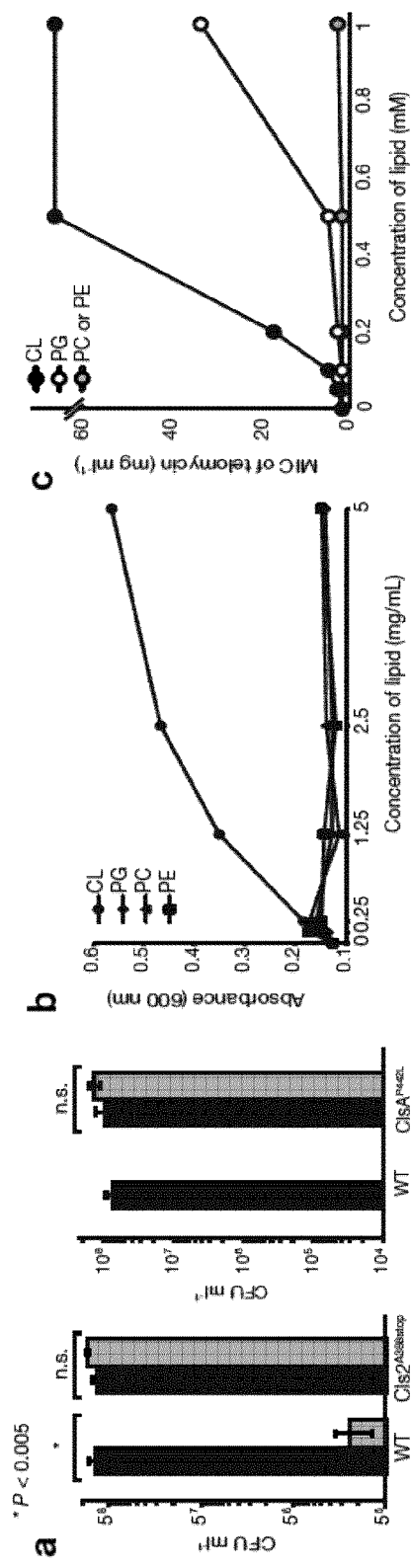
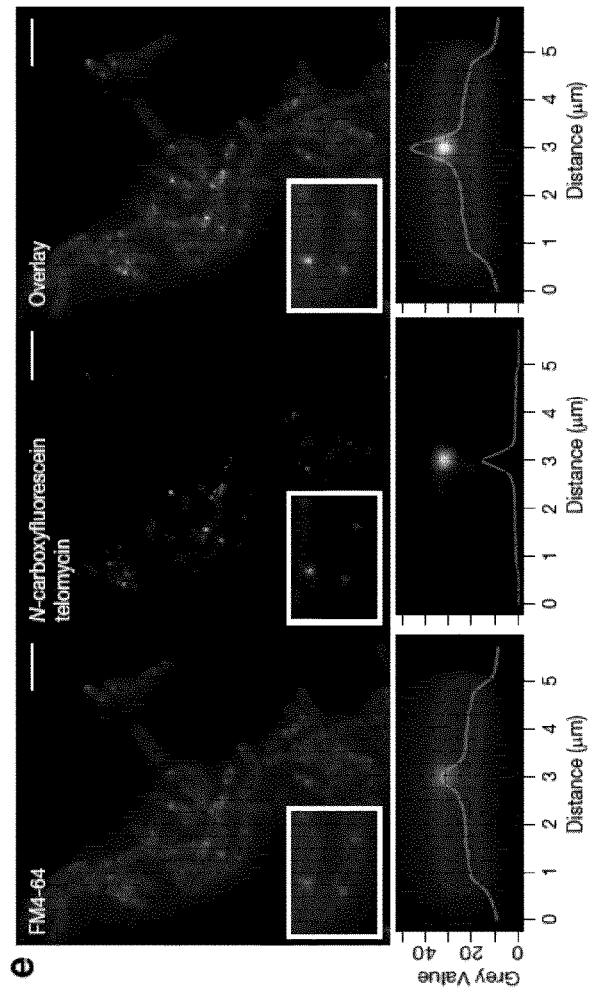
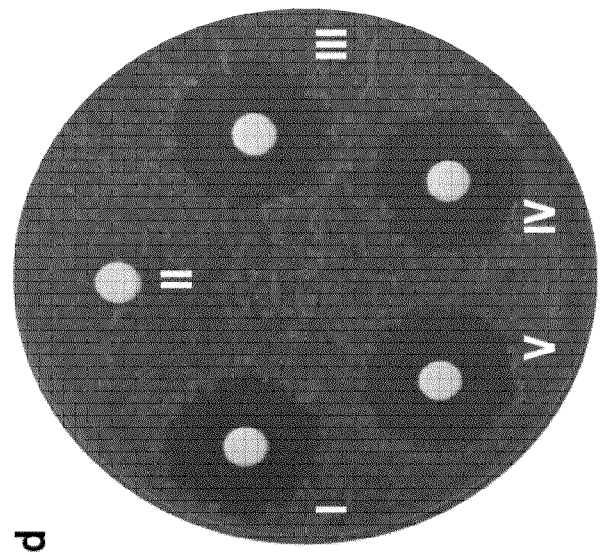

High resolution mass data for telomycin D (4)

| Compound | Formula | Calc. | Obs. | Δppm |
|---|---|---|---|---|
| Telomycin D (4) | C59H80N13O18 [M+H] | 1258.57388 | 1258.57210 | 1.85 |

| Breakage type | Bond breakage reactions | Examples[1] |
|---|---|---|
| Macrolide | | Erythromycin |
| Thioesters | | Thiocoraline |
| Macrolactam | | ML-449 |
| B lactam like structures | | Salinosporimide |
| | | Cephalosporin; penicillin |
| | | Nocardicin |
| Oxazoles | | Chivosazole A |
| Thiazoles | | Curacin |
| Multi-thiazoles | | Bleomycin |
| Kendomycin substructure | | Kendomycin |

FIG. 43

| Breakage type | Bond breakage reactions | Examples[1] |
|---|---|---|
| Avermectin terminal substructure | | Avermectin |
| Avermectin starter substructure | | Avermectin |
| Piercidin type substructure | | Piercidin |
| Anthramycin type substructure | | Anthramycin |
| Epoxiketone type substructure | | Eponemycin |
| Cyclic ether process 1 in PK recognition | $R_1$ is the starter of the polyketide chian, while $R_2$ is the terminus of polyketide chain | Monensin |
| Cyclic ether process 2 in PK recognition | $R_1$ is the starter of the polyketide chian, while $R_2$ is the terminus of polyketide chain | Monensin |
| PK epoxide restoration | $R_1$ is the starter of the polyketide chian, while $R_2$ is the terminus of polyketide chain | Mupirocin |

FIG. 43 (continued)

TABLE 2

| Breakage type | Bond breakage reactions | Examples[1] |
|---|---|---|
| Imide bonds | $R_1-C(OH)=N-R_2 \Rightarrow R_1-C(=O)-NH-R_2$ | Arthrofactin |
| Amide bonds | $R_1-C(=O)-NR_2R_3 \Rightarrow R_1-COOH + HNR_2R_3$ | Arthrofactin |
| Ureido bonds | $R_1R_3N-C(=O)-NR_2R_4 \Rightarrow R_3NH-R_1 + R_4NH-R_2$ | Mycoplanecin D |
| Disulfide bridges | $R_1-S-S-R_2 \Rightarrow R_1-SH + R_2-SH$ | SW163C |
| Ether bridged aromatics | (aryl-O-aryl $\Rightarrow$ aryl-OH + HO-aryl) | Vancomycin |
| Bi-aryl C-C linkages between aromatics | (biaryl $\Rightarrow$ two aryls) | Vancomycin |
| Sulphate groups | $R-O-SO_3H \Rightarrow R-OH + H_2SO_4$ | A-47934 |
| Glycans | (disaccharide $\Rightarrow$ two sugars) | Apoptolidin |

FIG. 44

Rules for RiPP biosynthetic gene cluster detection in PRISM.

| RiPP class | Hidden Markov model hits |
|---|---|
| Autoinducing peptide | AgrB and AgrD |
| Bacterial head-to-tail cyclized peptide | DUF95 and HTT_precursor |
| Bottromycin | BotA and BotC |
| ComX | ComQ and ComX |
| Cyanobactin | PatA and PatE and (PatG or PatG_ox) |
| Glycocin | SunA and SunS |
| Class I lantipeptide | LanB and LanC |
| Class II lantipeptide | LanM |
| Class III/IV lantipeptide | LanKC |
| Lasso peptide | transglutaminases and asparagine_synthases |
| Linaridin | (CypA or LegA) and (CypH or LegH) and CypL |
| Linear azole-containing peptide | (McbB and (McbC or McbD)) or GodG |
| Microviridin | MdnA and (MdnB or MdnC) |
| Prochlorosin | ProcA |
| Proteusin | PoyA and PoyD |
| Sactipeptide | SboA and AlbA |
| Streptide | StrA and StrB and StrC |
| Thiopeptide | LazA and LazB and LazC |
| Trifolitoxin | TfxA and TfxB and TfxB |
| Thioviridamide | TvaA and TvaH |
| YM-216391 | YmA and YmF |

FIG. 45

|  | B. subtilis 168 wildtype | B. subtilis 168 Telo$^R$ | S. aureus Newman wildtype | S. aureus Newman Telo$^R$ |
|---|---|---|---|---|
| (1) | 1 | 16 | 8 | 128 |
| (2) | 1 | 8 | 4 | 32 |
| (3) | 1 | 8 | 4 | 32 |
| (4) | 2 | 16 | 16 | 64 |
| (5) | 4 | 32 | 32 | 128 |
| (6) | 0.5 | 4 | 2 | 8 |
| (7) | 8 | 64 | 32 | >128 |
| (8) | 0.5 | 2 | 4 | 16 |
| di-5-hydroxytryptophan telomycin (9) | >128 | >128 | >128 | >128 |
| di-5-methoxytryptophan telomycin (10) | 8 | 128 | 32 | >128 |

FIG. 46

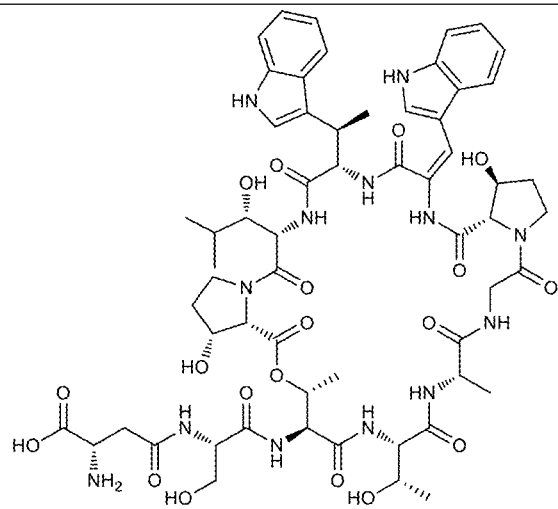
1 Telomycin A
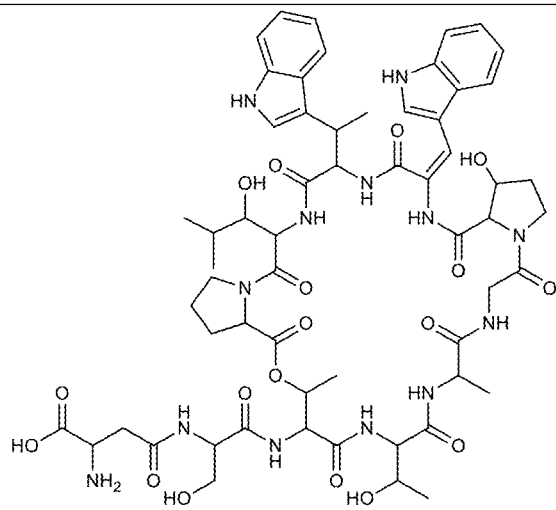
2 Telomycin B
FIG. 47

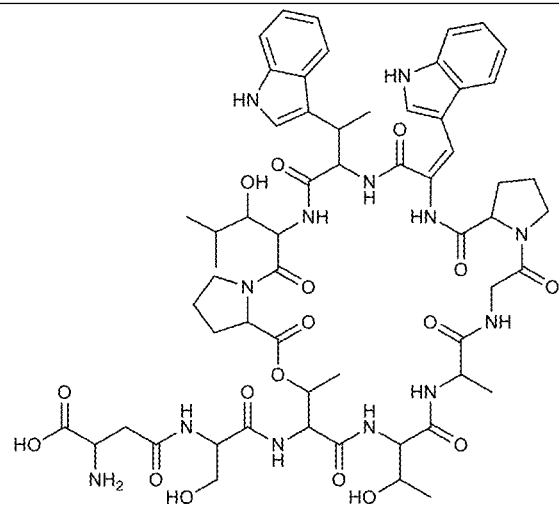
3 Telomycin C
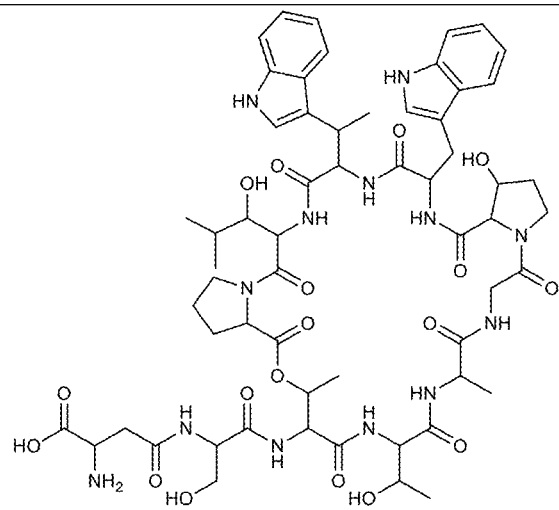
4 Telomycin D
FIG. 47 (continued)

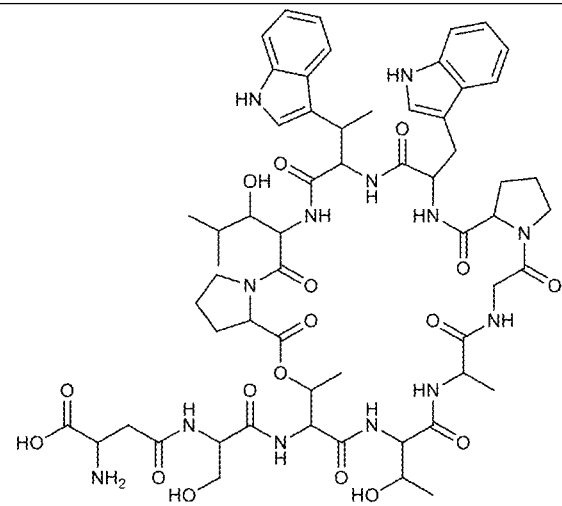
5 Telomycin E
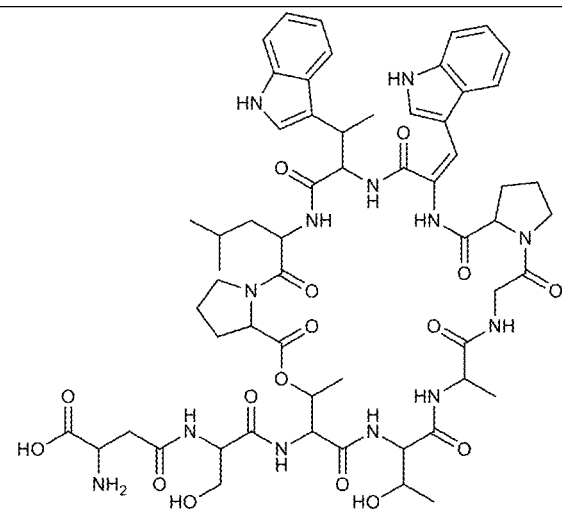
6 Telomycin F
FIG. 47 (continued)

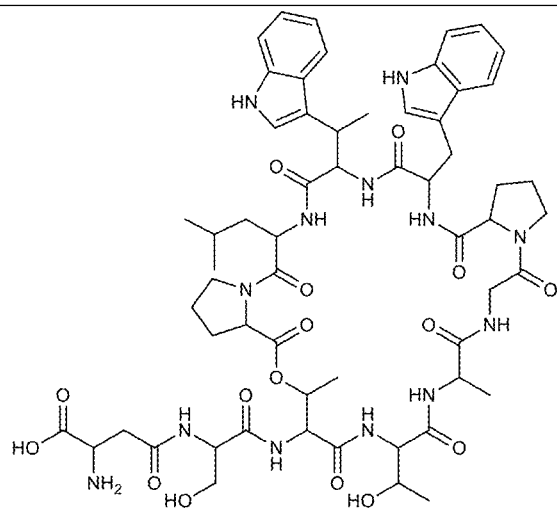
7 Telomycin G
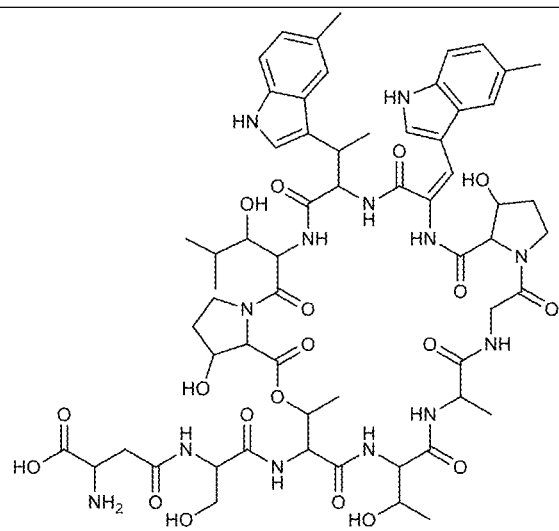
8 Di-5-methyltryptophan telomycin
FIG. 47 (continued)

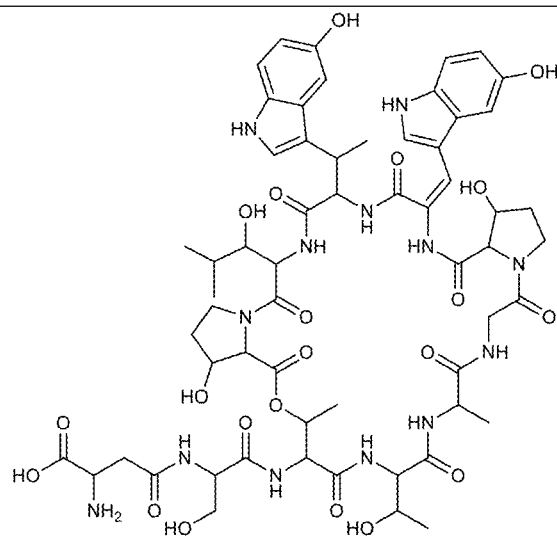
9 Di-5-hydroxytryptophan telomycin
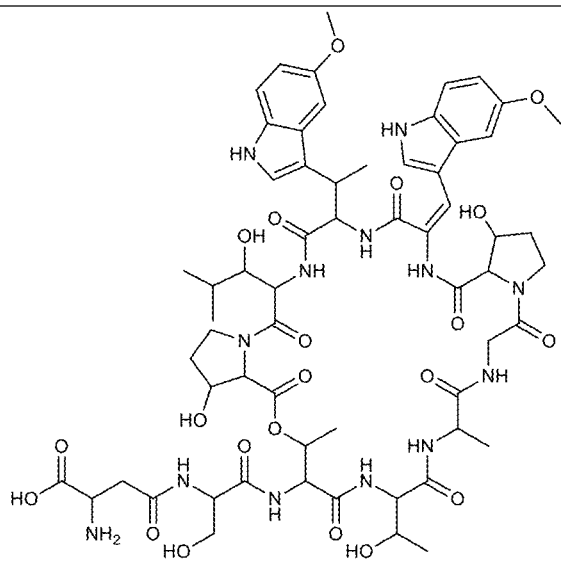
10 Di-5-methoxytryptophan telomycin
FIG. 47 (continued)

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: primer

<400> SEQUENCE: 1
gttttaaaga aatctgcccg                                                   20

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
gcgagacgga ttcttttatt                                                   20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
atgaaggtat ttatcgtgat                                                   20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ttataagaaa taagataatg                                                   20
```

NATURAL PRODUCT AND GENETIC DATA ANALYSIS AND DISCOVERY SYSTEM, METHOD AND COMPUTATIONAL PLATFORM THEREFOR

TECHNICAL FIELD

The present disclosure relates to natural product and genetic data analysis, and, in particular, to a natural product and genetic data analysis and discovery system, method and computational platform therefor.

REFERENCE TO SEQUENCE LISTING

The present application is being filed along with a Sequence Listing in electronic format. The Sequence Listing is provided as a file entitled 56520311_1.TXT, created and last modified on Oct. 26, 2022, which is 1.36 Kb in size. The information in the electronic format of the Sequence Listing is incorporated herein by reference in its entirety.

BACKGROUND

Microbial natural products are an evolved resource of bioactive small molecules which form the foundation of many modern therapeutic regimens. Genome sequencing has revealed that the vast majority of genetically encoded natural products remain unknown[2], an observation which has spurred interest in leveraging bacterial genome sequence data for natural product discovery. Additionally, genome sequencing efforts are uncovering natural product gene clusters at an unprecedented rate, yet only a relatively small portion of these have been associated with known products. This disparity indicates that a number of new gene clusters encode known molecules, and also that many more should produce valuable new natural products. Furthermore, reconciling this genomic sequence data with modern mass spectrographic techniques provides an efficient, directed means to quickly characterize natural products.

Microorganisms craft a wide range of small molecules from modular assembly lines, such as polyketide synthases (PKSs) and nonribosomal peptide synthetases (NRPSs), which are intrinsically capable of creating unique molecular architectures. In addition, peptidic natural products can be produced via a ribosomal pathway, followed by extensive post-translational modification, and these are termed ribosomally produced and post-translationally modified peptides (RiPPs). Following the discovery of penicillin, bioactivity-guided fractionation and screening of microbial cultures has revealed >11,000 PK/NRP products. With few exceptions, clinically relevant antibacterials are derived from microbial natural product antibiotics. Although the scale and size of this natural antibacterial collective has been poorly defined to date, it is composed of valuable chemical structures that have seemingly been honed through natural selection to provide microbes with competitive advantages in their native environment. In addition to antibacterials, microbial natural products are used in oncology, infectious diseases, cardiovascular diseases, immunology and organ transplantation, and a myriad of other conditions.

Extensive biosynthetic characterization has enabled the prediction of structural elements of microbial natural products from sequence data. In the past two decades, a wealth of discovery tools, databases, and chemical structure prediction algorithms have been developed to exploit the assembly line logic of PKSs and NRPSs and facilitate genome-guided efforts for identifying these modular natural products. The disparity between gene cluster being able to be linked, are associated, with known natural products indicates not only that a number of new gene clusters encode known molecules, but also that many more should produce valuable new natural products.

The initial discovery of the erythromycin gene cluster provided a valuable example of how Nature uses modular biosynthetic logic to craft bioactive molecules. Knowledge of the biosynthetic origins of NRP and PK molecules has been thoroughly confirmed by gene knockout studies, which have matched ~568 PK/NRP products to their respective gene clusters. The localized nature of biosynthetic genes also expedited rigorous enzymology studies that defined the unifying principles and specialized reactions within NRP and PK systems. Now, next generation sequencing is significantly accelerating the rate of gene cluster discovery, revealing active biosynthetic loci as well as 'cryptic', silent clusters. In spite of their inherent challenges, several cryptic gene clusters have been shown to be at least minimally or conditionally active, yielding low abundance bioactive products. By leveraging both classical natural products chemistry and our knowledge of biosynthesis, bioinformatic algorithms can be developed to determine which gene clusters produce the >11,000 known NRPs and PKs, and which may yield highly valuable new molecules.

Natural products produced by modular biosynthetic gene clusters frequently possess bioactive chemical scaffolds that have been honed by natural selection, leading to families of molecules that represent variations on a conserved core directed towards a common molecular target. Using new chemoinformatic techniques that can leverage a knowledge of biosynthesis, these families can be elaborated and charted in order to direct efforts towards exotic natural products with little chemical similarity to families with known modes of action. Bioinformatic analysis can also be used to direct efforts towards molecules that are unlikely to possess known targets. While many natural product biosynthesis genes are useful for inferring natural product structures, others can provide clues on natural product function.

Studies of antibacterial resistance genes that are naturally associated with biosynthetic gene clusters have revealed that resistance determinants typically have functions related to a specific class of small molecule, corresponding to a given antibiotic scaffold or its molecular target. As such, resistance genes may provide a unique opportunity to reveal the target of a given antibiotic, independent of structural similarity to known molecules.

In recent years, biosynthetic studies have characterized a growing number of peptidic natural products whose biosynthesis proceeds via a ribosomal pathway, followed by extensive post-translational modification, rather than by modular enzymatic assembly lines as noted above for PKSs and NRPs. These ribosomally produced and post-translationally modified peptides (RiPPs) include several families of natural products with exceptional biological activity and clinical potential. Because RiPPs are genetically encoded by small precursor peptides, their scaffolds can be predicted directly using the genetic code, theoretically facilitating extremely accurate structure predictions which could be used to guide natural product identification. However, the genetic diversity of RiPP precursor peptides, and extraordinary chemical diversity of their post-translational tailoring modifications, has to date largely precluded the development of automated tools for predicting and identifying RiPPs directly from genetic information, analogous to what has already been achieved for NRPS and PKS systems.

A widely accepted system of classification groups RiPPs into a number of distinct families based on shared biosynthetic or structural paradigms. The biosynthesis of all known families of RiPPs proceeds through serial post-translational modifications of a precursor peptide, which is composed of a core peptide that is modified to form the final natural product as well as recognition sequences for biosynthetic enzymes that flank the core peptide at either the N-terminus (leader peptide), C-terminus (follower peptide), or both. Leader and follower peptides are removed from the mature natural product by associated proteases. Post-translational modifications that tailor the core peptide range in complexity from simple head-to-tail macrocyclization, as observed in cyclic bacteriocins, to intricate enzymatic cascades such as those responsible for thiopeptide biosynthesis.

Bioinformatic investigations have revealed that the number of genetically encoded biosynthetic pathways vastly outnumbers known RiPPs. However, the tremendous diversity of RiPPs has led existing tools to focus on individual RiPP classes, and precluded the development of a universal tool for genome-guided RiPP structure prediction. As a result, the chemical space represented by genetically encoded RiPPs has largely remained dark. A computational analysis platform capable of comprehensively identifying RiPP clusters and predicting their genetically encoded products may allow this chemical space to be charted for the first time. Moreover, automated systems to facilitate rapid identification and structural characterization of genetically encoded RiPPs could significantly increase the pace of their discovery Current natural product genome mining techniques offer tools to identify clusters, but lacks a means to differentiate those encoding known versus new products. Increased computational accuracy that can more closely emulate Nature has been illustrated in recent updates to AntiSMASH (Antibiotitics and Secondary Metabolite Analysis Shell) and the highly accurate PRISM (Prediction Informatic for Secondary Matabolomes) engine. Still, predicting natural products from gene clusters remains a challenge due to frequent deviations in collinearity principles (order of genes and modular enzymes to products) and difficulty inferring reactions (e.g. regio-chemistry) from genes. For other natural biomolecules (e.g. proteins), the genetic code translates effectively, and algorithms such as BLAST (Basic Local Alignment Search Tool) readily define relationships and relatedness. Informatic alignment strategies have been useful in determining which genes encode for both known and unknown products, enabling focused investigations. Applying these principles to small molecules may provide a unique tool for rapidly assessing the novelty of downstream natural products directly from genomic data, and thus allow efforts to be focused on new gene clusters and new molecules with medical and industrial potential.

This background information is provided to reveal information believed by the applicant to be of possible relevance. No admission is necessarily intended, nor should be construed, that any of the preceding information constitutes prior art or forms part of the general common knowledge in the relevant art.

SUMMARY

The following presents a simplified summary of the general inventive concept(s) described herein to provide a basic understanding of some aspects of the invention. This summary is not an extensive overview of the invention. It is not intended to restrict key or critical elements of the invention or to delineate the scope of the invention beyond that which is explicitly or implicitly described by the following description and claims.

A need exists for a natural product and genetic data analysis and discovery system, method and computational platform therefor, that overcome some of the drawbacks of known techniques, or at least, provides a useful alternative thereto. Some aspects of this disclosure provide examples of such systems, methods and computational platforms.

In accordance with one aspect, there is provided a method for isolating a new natural product of interest from an input polynucleotide sequence. The method comprises: identifying a given gene cluster defined within the input polynucleotide sequence; determining a set of gene cluster-encoded chemical monomers associated with the given gene cluster; aligning the set of gene cluster-encoded chemical monomers with a similar set of deconstructed chemical monomers associated with deconstruction of a given known natural product; calculating a similarity score between the gene cluster-encoded chemical monomers and the deconstructed chemical monomers; and associating the known natural product with the given gene cluster as being predictably responsible therefor thereby defining the given known natural product as being the new natural product interest.

In some embodiments, the aligning and calculating are implemented for a plurality of known natural products and wherein the new natural product of interest is defined as a highest-scoring one of the known natural products.

In some embodiments, the similarity score is defined at least in part by a Tanimoto coefficient.

In some embodiments, the method further comprises, prior to the aligning: comparing a predicted mass spectral signature predictably associated the given gene cluster based on the set of gene cluster-encoded chemical monomers, with corresponding mass spectral signatures associated with a plurality of known natural products; and selecting the given known natural product as having a similar mass spectral signature at least in part based on the comparing.

In some embodiments of the method the identifying comprises identifying a plurality of gene clusters defined within said input polynucleotide sequence; and the method further comprises, prior to the aligning, comparing at least some of the identified gene clusters with a set of previously known gene clusters to identify a relatively unique one of the identified gene clusters; and the aligning, calculating and associating are executed, at least in part, in respect of the set of gene cluster-encoded chemical monomers associated with the relatively unique gene cluster.

In some embodiments, the method the comparing comprises: respectively aligning the set of gene cluster-encoded chemical monomers associated with each of the identified gene clusters with a similar set of previously known gene cluster-encoded chemical monomers associated with the previously known gene clusters; calculating respective similarity scores based on the aligning of gene cluster-encoded chemical monomers; and defining a lowest-scoring set of gene cluster-encoded chemical monomers as the relatively unique gene cluster.

In some embodiments of the method, the given gene cluster encodes for a ribosomally synthesized and/or post-translationally modified polypeptide (RiPP).

In some embodiments of the method, the given gene cluster encodes for a nonribosomal peptide (NRP).

In some embodiments of the method, the given gene cluster is derived from the polynucleotide sequence via Hidden Markov Modeling.

In some embodiments of the method, the deconstructed chemical monomers are determined by a generalized retobiosynthetic assembly prediction engine (GRAPE).

In some embodiments of the method, the similarity score is calculated via a global alignment for natural products cheminformatics engine (GARLIC).

In some embodiments, the method is automatically implemented by one or more digital processors of a computing platform having an interface to receive as input the input polynucleotide sequence and output the new natural product interest.

In another and/or complementary aspect, there is provided non-transitory computer readable medium having statements and instructions stored thereon to be executed by one or more digital processors of a computing platform to isolate a new natural product of interest from an input polynucleotide sequence by implementing the method for isolating a new natural product of interest from an input polynucleotide sequence, as defined herein.

In yet another aspect, there is provided a computerized system for isolating a new natural product of interest from an input polynucleotide sequence. The system comprises: a computer-readable medium having statements and instructions stored thereon to be executed by one or more digital processors of a computing platform to isolate a new natural product of interest from an input polynucleotide sequence by implementing the method for isolating a new natural product of interest from an input polynucleotide sequence where the one or more digital processors and an interface to receive as input the input polynucleotide sequence is provided and output the new natural product interest.

In some embodiments, the interface is a network interface directly or indirectly interfacing over a data network with the one or more digital processors and the computer-readable medium.

In some embodiments, network interface is a Web interface.

In yet another aspect, there is provided a method for identifying a gene cluster responsible of encoding for a harvested biosynthesized natural product. The method comprises: accessing a mass spectral signature associated with deconstruction of the harvested biosynthesized natural product; determining a sequence of deconstructed chemical monomers associated with the harvested biosynthesized natural product based on the mass spectral signature; aligning the sequence of deconstructed chemical monomers with a similar sequence of gene cluster-encoded chemical monomers associated with a known gene cluster; calculating a similarity score between the deconstructed chemical monomers and the gene cluster-encoded chemical monomers; and associating the known gene cluster with the harvested biosynthesized natural product as being predictably responsible for encoding for at least a part thereof.

In some embodiments, the aligning and calculating are implemented for a plurality of known gene clusters and wherein the natural product is associated with a highest-scoring one of the known gene clusters.

In some embodiments of the method, prior to the determining, comparing the mass spectral signature with a set of previously stored mass spectral signatures so as to isolate a relatively unique mass spectral signature portion and wherein the determining comprises determining the sequence of deconstructed chemical monomers associated with the relatively unique portion to ultimately identify a gene cluster of interest predictably associable therewith.

In some embodiments of the method, the sequence of deconstructed chemical monomers is determined by a generalized retobiosynthetic assembly prediction engine (GRAPE).

In some embodiments of the method, the similarity score is calculated via a global alignment for natural products cheminformatics engine (GARLIC).

In some embodiments of the method, the mass spectral signature is derived from input raw metabolomic data.

In some embodiments, the mass spectral signature comprises a set of mass spectrum peaks.

In some embodiments, the method is automatically implemented by one or more digital processors of a computing platform to output the known gene cluster from processing the mass spectral signature.

In another aspect, there is provided a non-transitory computer readable medium having statements and instructions stored thereon to be executed by one or more digital processors of a computing platform to identify a gene cluster of interest responsible of encoding for a harvested biosynthesized natural product by automatically implementing the method for identifying a gene cluster responsible of encoding for a harvested biosynthesized natural product as herein disclosed and described.

In yet another aspect, there is provided a computerized system for identifying a gene cluster responsible of encoding for a harvested biosynthesized natural product. The system comprises: a computer-readable medium having statements and instructions stored thereon to be executed by one or more digital processors of a computing platform to identify a gene cluster of interest responsible of encoding for a harvested biosynthesized natural product by automatically implementing the method for identifying a gene cluster responsible of encoding for a harvested biosynthesized natural product; the one or more digital processors; and an interface to access the mass spectral signature and output the known gene cluster.

In some embodiments, the interface is a network interface directly or indirectly interfacing over a data network with the one or more digital processors and the computer-readable medium.

In some embodiments, the network interface is a Web interface.

In yet another aspect, there is provided a computational platform for dynamically linking gene clusters with natural products predictably producible therefrom. The platform comprises: a polynucleotide sequence analysis engine operable on an accessed digital polynucleotide sequence to automatically identify: a set of constituent gene clusters for the polynucleotide sequence; and a set of gene cluster-encoded chemical monomers corresponding with each of the set of constituent gene clusters, wherein each the set of gene cluster-encoded chemical monomers is digitally associable with a corresponding digital mass spectral signature related to a predicted natural product producible therefrom; a natural product analysis engine operable on an accessed digital mass spectral signature corresponding to a given natural product to automatically identify a set of deconstructed chemical monomers associated with the given natural product based at least in part on the mass spectral signature; and a molecular similarity scaling engine operable to automatically align given sets of gene cluster-encoded chemical monomers with similar sets of deconstructed chemical monomers to calculate a corresponding similarity score therebetween and thereby digitally associate a new gene cluster-product pair based at least in part on their corresponding similarity score being above a designated similarity threshold.

In some embodiments, the computational platform further comprises a mass spectral signature scaling engine operable to automatically compare an input mass spectral signature corresponding with a predicted or known input natural product, with a set of previously stored mass spectral signatures to identify one or more known or predicted output natural products similar to the predicted or known input natural product.

In some embodiments, the computational platform further comprises an input interface to receive as input a user-selected polynucleotide sequence; wherein the polynucleotide sequence analysis engine identifies a given set of constituent gene clusters related to the user-selected polynucleotide sequence; wherein the molecular alignment engine aligns each of the given set with a set of previously known gene clusters to identify a relatively unique gene cluster associated with the user-selected polynucleotide sequence, and further aligns a set of gene cluster-encoded chemical monomers corresponding with the relatively unique gene cluster with the similar sets of deconstructed chemical monomers to calculate the corresponding similarity score therebetween and thereby digitally associate a new natural product of interest with the relatively unique gene cluster based at least in part on their corresponding similarity score being above a designated similarity threshold.

In some embodiments, the computational platform further comprises: a mass spectral signature scaling engine operable to automatically compare a mass spectral signature associated with a predicted natural product predictably producible from the relatively unique gene cluster, with a set of previously stored mass spectral signatures to identify one or more known natural products similar to the predicted natural product and thus define the similar sets of deconstructed chemical monomers to be used for alignment by the molecular alignment engine in identifying the new natural product of interest.

The examples of the disclosure provide various methods of linking natural products and gene clusters.

In one embodiment, natural product monomers are predicted from a gene sequence.

In another embodiment, natural product monomers are predicted from a chemical structure of a natural product.

In another embodiment, the monomers predicted from a gene sequence are aligned with the monomers predicted from a chemical structure.

In another embodiment, one or more natural products are predicted from a gene sequence.

In another embodiment, one or more gene clusters is predicted from a chemical structure of a natural product.

In another embodiment, targets, chemical origins and families of an antimicrobial natural product are predicted.

In another embodiment, the method is used to identify unknown natural products (depreplication). In another embodiment the unknown natural products are investigated for biological activity.

In another embodiment, the method facilitates the discovery of new natural products.

BRIEF DESCRIPTION OF THE FIGURES

In order that the invention may be better understood, exemplary embodiments will now be described by way of example only, with references to the accompanying drawings, wherein:

FIG. 9A is a plot of biosynthetic geneclusters by RiPP family and taxonomic class.

FIG. 9B is a plot of unique products by RiPP family.

FIG. 16A shows the structure of Telomycin.

FIG. 16B shows the lytic ability of Telomycin against gram positive bacteria.

FIG. 19A graphically depicts lysis by telomycin of sensitive and resistant bacterial strains.

FIG. 19B graphically demonstrates the precipitation of telomycin and cardiolipin, represented by increased turbidity.

FIG. 19C graphically demonstrates the effect of excess cardiolipin on the lytic ability of telomycin.

FIG. 19D graphically and pictorially demonstrates the effect of excess cardiolipin on the lytic ability of telomycin.

FIG. 19E demonstrates fluorescent labeling of telomycin and localization within bacterial cells.

FIG. 43 summarizes Macrocycle & Heterocycle Cleavage Reactions. Each type of bond breakage is shown with the associated retro-synthesis reaction and a compound reflecting the type of bond breakage as an example. The R groups in reactions are used to simplify structures and are independent to each other. The GRAPE breakdowns of all examples are listed at the end of the figure.

FIG. 45 summarizes the rules for RiPP gene cluster detection in PRISM.

FIG. 46 summarizes MICs of telomycin antibiotics (1-10). Sensitive and resistant strains were exposed to telomycins and MICs were measured by microdilution in CAMHB. MICs were determined after 16 h growth, and are shown in μg ml−1.

DETAILED DESCRIPTION

I. Definitions

Figure 1:
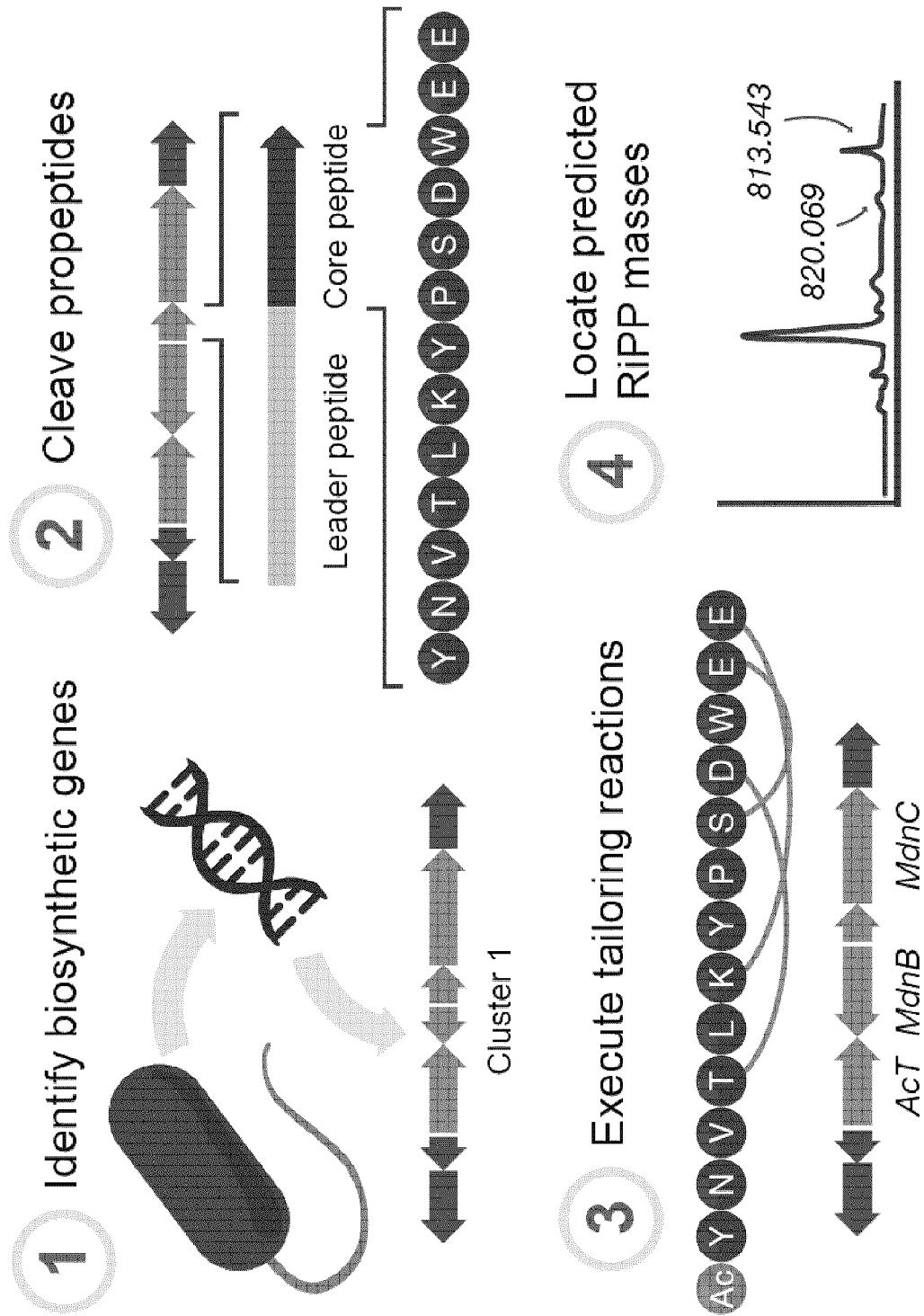
FIG. 1 is a visualization of the PRediction Informatics for Secondary Metabolomes (PRISM) pipeline.

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "an antibiotic" should be understood to present certain aspects with one substance or two or more additional substances.

In embodiments comprising an "additional" or "second" component, such as an additional or second antibiotic, the second component as used herein is chemically different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

II. EMBODIMENTS

Described herein are various embodiments of a natural product and genetic data analysis and discovery system and method, and computational platform therefor, as well as various computation tools and data structures in support thereof. As will be described in greater detail below, the systems considered herein provide and rely on a complex interconnection of distinct data types than can be effectively aligned, compared and linked to efficiently mine new and existing data and data sources in the analysis and discovery of new natural products, genetic clusters, and the underlying molecular and genetic constructs and characteristics associated, or at least predictably associated therewith.

For example, methods and computational systems described herein may be operated to effectively link heretofore disassociated or newly considered gene clusters and/ or natural products. For this purpose, natural products, molecules and/or genetic sequences/clusters characterized herein as new may in fact have already been observed or considered, and data related thereto stored in one or more genetic or molecular data stores, libraries and the like; however, some of the embodiments considered herein seek to newly recognize such previously observed items as being of particular interest, for example, by being relatively unique, rare or by generally exhibiting a relatively heigh dissimilarity when compared to the bulk of known or relatable products and accessible data. Such uniqueness or dissimilarity may thus compel further investigation as to the chemical and/or bioactive properties of such products and their derivatives, as well as to the various new and informative links that may be established, invoked and/or refined based on the analyses, conclusions and predictions rendered available by the systems architecture, functions and associated toolset.

That being said, the data constructs and system architecture described herein, with reference to different embodiments, allow for the execution of diversified data mining investigations not necessarily limited to the identification of potentially new and/or relatively dissimilar products and/or genetic information. Further, many of the computational tools and related processes described herein are in and of themselves particularly innovative and useful in addressing various challenges when confronting the sizeable volume of biotechnological and genetic data available and of potential interest when mining for new or useful solutions and connections.

In one particular embodiment, an intelligent computational platform is executed as a network accessible server-based platform whereby user inputs and processing preferences/characteristics may be delivered via a network interface, such as a Web interface, and processed via one or more backend data process servers to render a digital output via this same interface or again via a delayed electronic correspondence to the user (e.g. post-processing electronic correspondence attachment, data transfer or the like).

The backend architecture of the system may include a series of interconnected data stores and/or processors, or again invoke communicative links to distinct networked or Web-enabled data storing and/or processing services to compile a desired end result. Likewise, embodiements may rather operate locally as a self-contained system. These and other general system architectures will be readily apparent to the person of ordinary skill in the art and should therefore be equally considered to fall within the general scope and nature of the present disclosure.

As noted above, and as will be further detailed below, embodiments of the herein described system and platform may be configured to invoke one or more local or distributed computational tools to process various inputs or internal parameters in the ultimate delivery of output results, while also potentially allowing the system and platform to enrich stored relations and interrelations, and thus promote system self-learning opportunities.

These computational tools/engines include, but as will be detailed below, are not limited to:

- a polynucleotide sequence analysis engine operable on input or accessed polynucleotide sequences, for example, hereinafter interchangeably referred to as PRISM (Prediction Information for Secondary Metabolomes) in accordance with one exemplary embodiment;
- a natural product analysis engine operable on input or accessed spectral signatures corresponding to natural products, for example, hereinafter interchangeably referred to as GRAPE (Generalized Retrobiosynthetic Assembly Prediction Engine) in accordance with one exemplary embodiment;
- a molecular similarity scaling engine operable to automatically align given sets of chemical monometers, whether derived from gene clusters extracted from an input or accessed polynucleotide sequence by PRISM and/or derived from a natural product deconstruction process output from GRAPE, for example, and hereinafter interchangeably referred to as GARLIC (Global Alignment for Natural Product ChemInformatics); and
- a mass spectral signature scaling engine operable to automatically compare mass spectral signatures so to establish similarity links based on an output similarity scale.

The computational tools may be invoked, in different combinations and/or sequences, in different applications of the herein described platform to assist in the execution of certain data mining and association tasks. Other computational tools may also be used, as detailed below, to cooperate with any one or more of the above-noted tools, or independently based on previously stored data and/or recently stored data and links established by the execution of these and related tools in user inputs and queries.

For illustrative purposes, some of these tools are defined in greater detail below, in accordance with a preferred embodiment.

PRISM (Prediction Information for Secondary Metabolomes)

PRISM is a computational tool that relies on the implementation of a database integration algorithm to integrate various genomic databases of known gene sequences known to encode known molecules, so to identify gene clusters in an input sequence when compared with the integrated databases.

Accordingly, where an input gene sequence corresponds with a known sequence in the integrated database, this input sequence will be equally determined to correspond with this known molecule.

An input gene sequence can be mined to discover if this gene sequence is known and what known natural products, if any, can be produced by the assembly of molecules encoded by the input sequence. When a gene sequence is entered, if a gene sequence for a known natural product is matched, and thus a known gene sequence is identified, it can be said that the inputted gene sequence matches a gene cluster to produce the known natural product (previously discovered).

If the gene sequence is not matched, but conserved genetic sequences or gene clusters are matched which are known to encode for particular molecules of a natural product, a prediction can be made regarding how the molecules (amino acids) can be assembled to produce an unknown natural product (newly discovered).

Therefore, a previously unclassified genetic sequence can be inputted to output predictions as to a previously unknown natural product that may be produced by the input genetic sequence.

Conversely, input chemical information (amino acid assembly) related to a target natural product can return which gene clusters may be responsible for producing this target natural product.

As further illustrated below, PRISM can thus be invoked to effectively allow the platform to link an input or accessed gene sequence with constituent gene clusters, and related chemical monomers (e.g. amino acids) and their predictable assembly into a predicted natural product, and a mass spectral signature predictably associated therewith.

More specifically, PRISM is an application designed to identify biosynthetic gene clusters and predict the structures of genetically encoded nonribosomal peptides and type I and II polyketides. PRISM implements a library of nearly 500 hidden Markov models to identify conserved biosynthetic genes and the substrates of adenylation, acyltransferase, and acyl-adenylating enzymes. A simple greedy algorithm is used to identify plausible biosynthetic gene clusters, and rules specific to modular, trans-acyltransferase, and iterative type I polyketides, type II polyketides, and nonribosomal peptides are used to define true clusters. A library of 57 virtual tailoring reactions is leveraged in order to generate a combinatorial library of chemical structures when multiple potential substrates are biosynthetically plausible for one or more tailoring enzymes, including macrocyclization, heterocyclization, aromatization, halogenation, C- and O-glycosylation, O-, N-, and C-methylation, carbamoylation, amination, formylation, phosphorylation, sulfonation, oxidation and reduction, mono- and deoxygenation, Baeyer-Villager rearrangement, and acyl group transfer. A set of hidden Markov models for conserved deoxysugar biosynthesis genes and a BLAST database of natural product glycosyltransferases is used to predict potential combinations of hexose and deoxysugars which tailor the natural product scaffold, and a library of models for type II polyketide cyclases is used to predict the scaffolds of type II polyketides. In addition to generating combinatorial libraries of chemical structures, biosynthetic information detected by PRISM can be aligned to biosynthetic information from other clusters, or to retrobiosynthetic information generated by GRAPE, within the GARLIC alignment.

PRISM also provides a comprehensive structure prediction algorithm which identifies biosynthetic gene clusters and generates libraries of hypothetical structures for 21 families of RiPPs (FIG. 1). Libraries of 154 hidden Markov models and 58 motifs are leveraged to identify RiPP biosynthetic gene clusters, predict precursor peptide cleavage, and execute virtual tailoring reactions, resulting in highly accurate combinatorial structure prediction across a broad range of chemical families. The accuracy of PRISM's structure predictions was validated and was shown to demonstrate unparalleled performance of cluster identification, leader peptide cleavage, and chemical structure generation across all known families of ribosomal natural products. The genomes of over 60,000 microbes was mined to characterize the biosynthetic and structural landscape of RiPPs and comprehensively describe RiPP chemical space. Databases of predicted structures generated by PRISM were combined with automated LC-MS analysis to reveal a new member of the rare RiPP family related to the cytotoxic molecule YM-216391. This analysis reveals the widespread distribution of RiPPs throughout the microbial tree of life, and provides a platform for the targeted, genome-guided discovery of novel RiPPs.

GRAPE (Generalized Retrobiosynthetic Assembly Prediction Engine) (Smiles)

GRAPE is a computational tool which reverse-engineers natural products into their component molecules. For example, from a lysate of bacteria (column filtered fractions to isolate natural products), or an isolated natural product, mass spectral data (MS peaks) can be utilized to determine the chemical structure of a natural product. This natural product can then be computationally reduced into its constituent molecules (amino acids).

Accordingly, GRAPE may be invoked to compute or at least predict links between accessed or input natural products, their mass spectral signature(s), and a small molecule (chemical monomer) assembly associated therewith.

Figure 2:
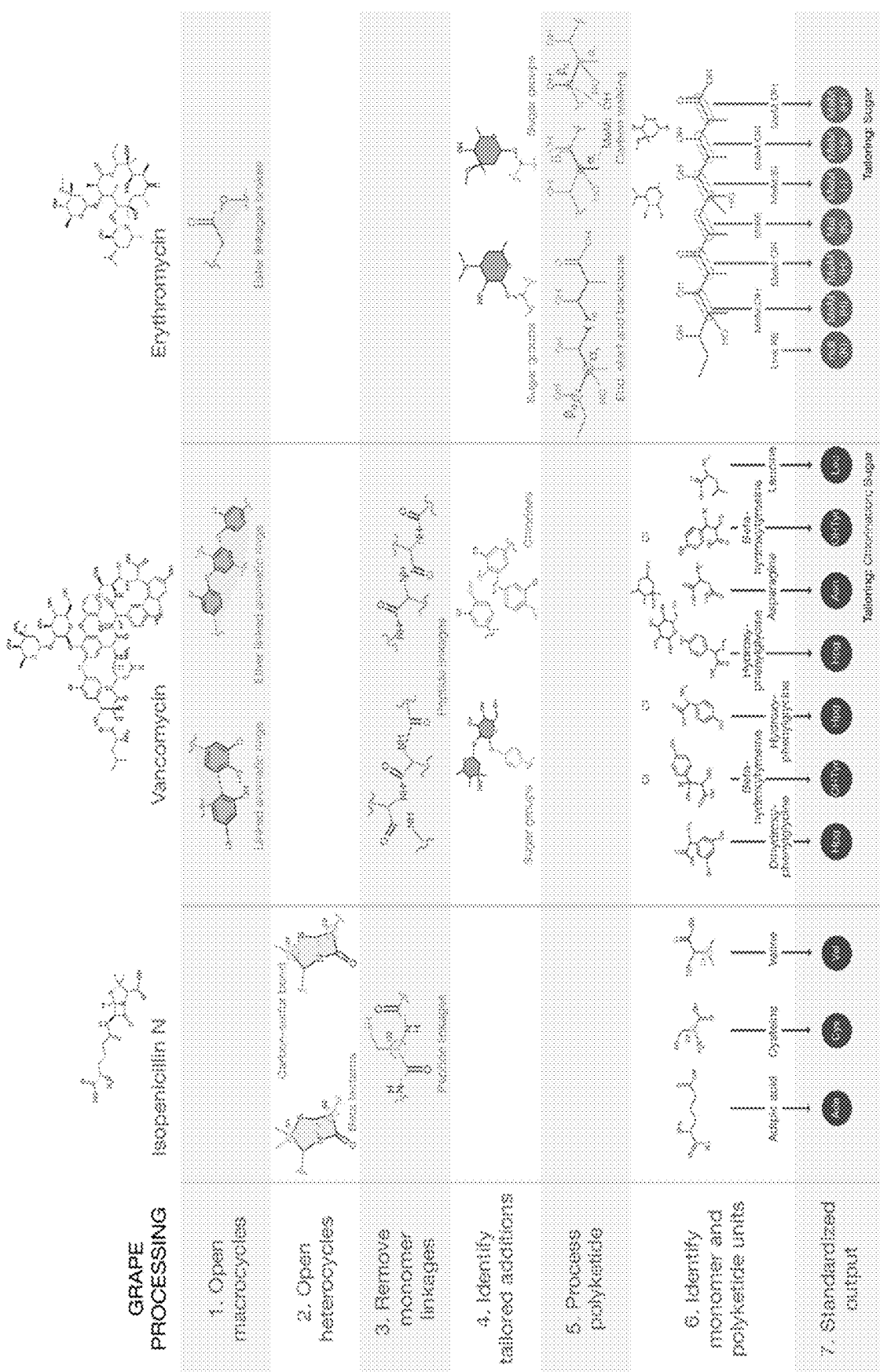
FIG. 2 demonstrates a workflow of Generalized Retro-biosynthetic Assembly Prediction Engine (GRAPE). Three distinct natural products: isopenicillin, a β-lactam, vancomycin, a glycopeptide, and erythromycin, a macrolide, broken down via GRAPE.
Figure 3:
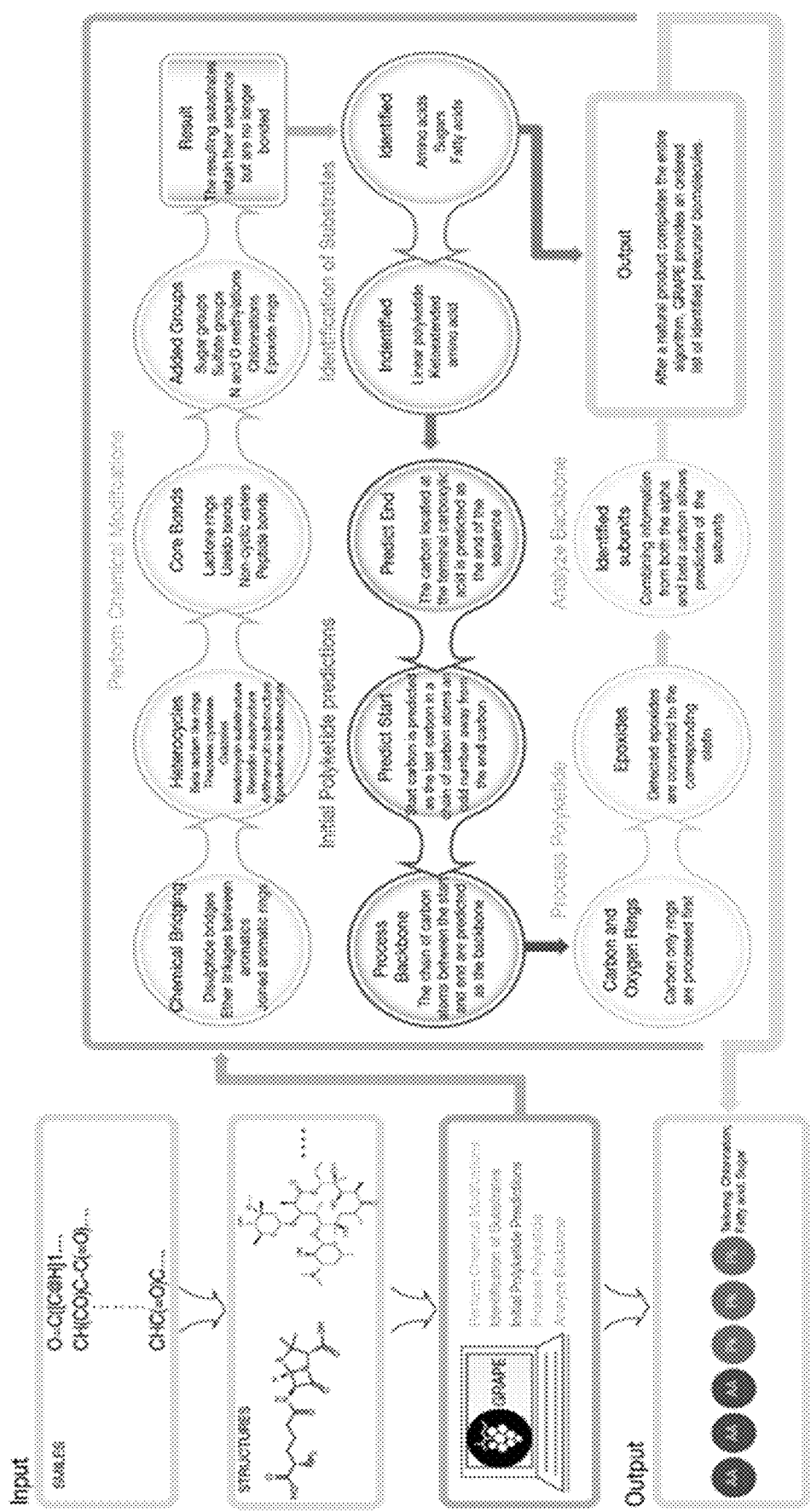
FIG. 3 is a visualization of GRAPE process pipeline. GRAPE takes in small molecule structures in the form of SMILES and breaks them down in the order shown, while capturing details of the chemistries during retro-synthesis. The final output is monomer information for both amino acids (AA) and polyketides (PK), as well as additional tailoring and scaffold information.
Figure 44:
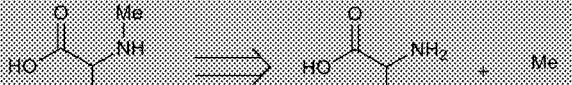
FIG. 44 summarizes Cleaving Chemical Bonds between monomers and tailorings. Each type of bond breakage was shown with the associated retro-synthesis reaction and a compound reflecting the type of bond breakage as an example. The R groups in reactions are used to simplify structures and are independent to each other. The GRAPE breakdowns of all examples were listed at the end of the figure.
Figure 47:
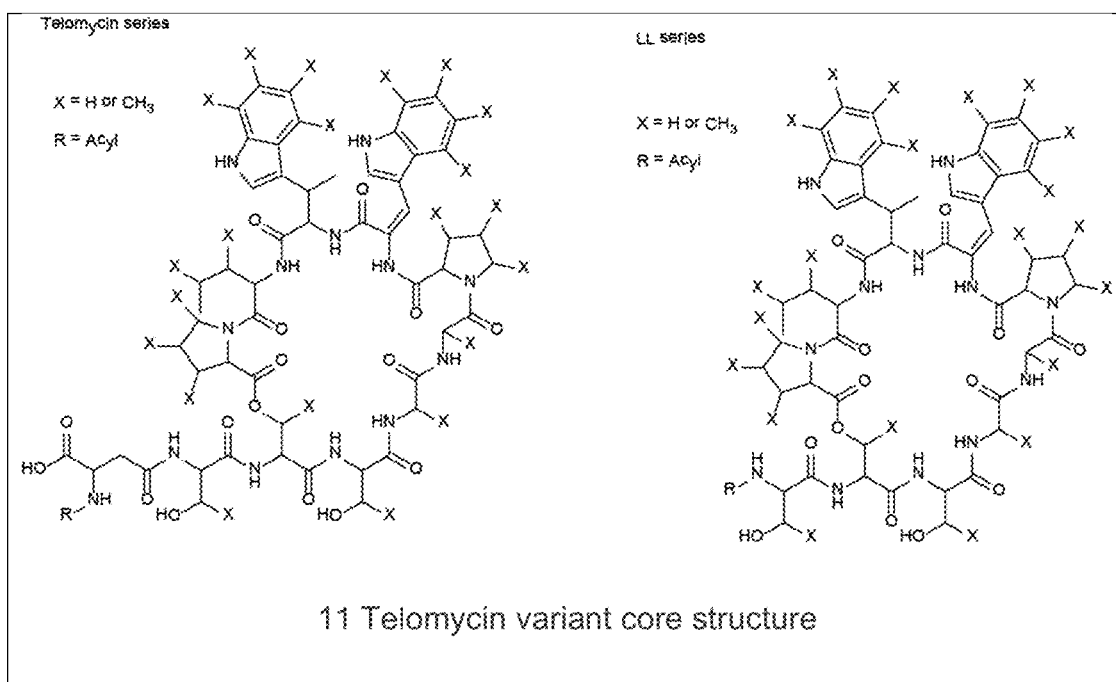
FIG. 47 summarizes structures of Telomycin variants.

More specifically, GRAPE is a computational tool which predicts the biosynthetic assembly of natural products from their chemical structures (FIG. 2). GRAPE was designed to rapidly annotate large chemical databases with a focus on NRP (Non-Ribosomal Peptide) and PK (Polyketide) assembly units. For each chemical structure, GRAPE performs a collection of chemical reactions in reverse, storing relevant biosynthetic information at each step (FIGS. 43 and 44, FIG. 3). GRAPE output consists of two components: an ordered list of monomeric units which correspond to an NRPS or PKS assembly line, and a list of chemical features that correspond to non-assembly line biosynthetic enzymes (FIG. 45). GRAPE was developed in the Java programming language using libraries from the Chemistry Development Kit, and the Maximum Common Subgraph (MCS) algorithm from the Small Molecule Subgraph Detector toolkit (SMSD).

In connection with GRAPE, SMILES (Simplified Molecular-Input Line-Entry System), developed in the 1980's, a line notation system for encoding molecular structure into in text, the SMILES strings is utilized. In a simplified sense, the first atom in a chemical chain is denoted position 1, the next atom is written in following this method until a branch from backbone is found. Then at the atom where the branch is found, the structure of the branch is then noted in brackets using the same format. This allows the chemical structure of a molecule to be written in line of text. Accordingly, when the molecular structure of a molecules is converted into a text line structure, it can then me run through a database and matches against other structures. Essentially it allows the structure of molecules to be expressed in a binary language that can easily be run through databases to find similar structures Given chemical structures as input in SMILES format, GRAPE performs matching against a database of scaffolds and then reverse biosynthetic chemical reactions. Each compound is first compared against scaffolds for non-modular polyketides, enedyines and terpenes. This comparison checks if any of these scaffolds are a substructure of the compound for initial classification. The subsequent reverse biosynthetic chemical reactions fall under four major steps (FIG. 2 and FIG. 3). First, macrocycle-forming chemical bridges are reversed, such as disulfide bonds and ether linkages between aromatic rings. Second, reactions forming heterocyclic structures such as thiazoles, oxazoles, penams, and penems are performed in reverse. Rare chemistries such as those found in kendomycin, avermectin, and piericidin as well as di-cystine linkages are scanned for using substructure and chemistries reversed. Third, core linking bonds, such as peptide bonds, thioesters, and ester linkages, are reversed. After these chemical reactions are performed, the resulting monomeric chemical structures are identified as amino acids, fatty acids, sugars, or small polyketide fragments.

Figure 4:
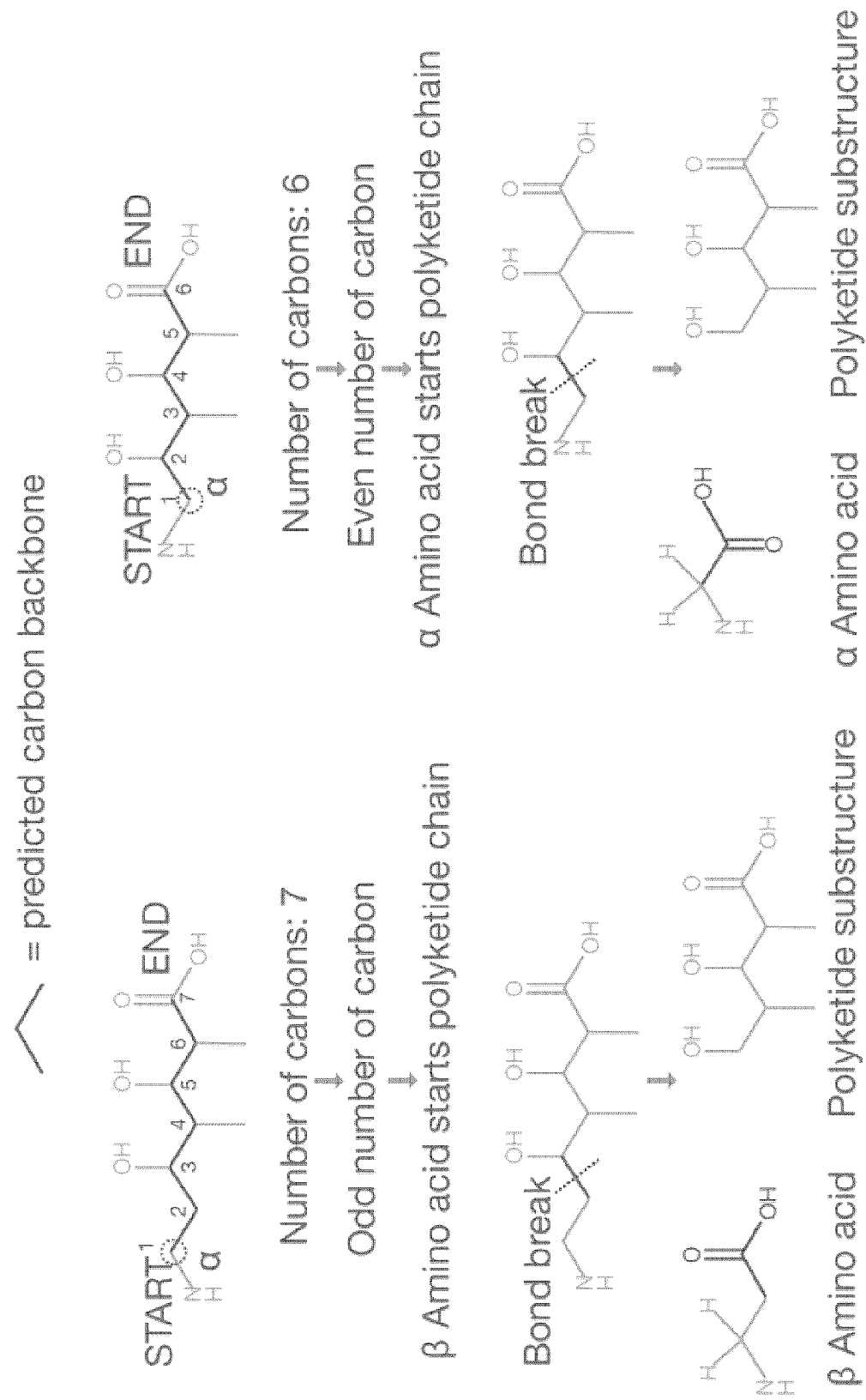
FIG. 4 is a visualization of amino acids as acyl keto-extension units in hybrid polyketides and non-ribosomal peptides. GRAPE identifies the longest carbon only backbone from the α-carbon of the amine to carbonyl carbon of the furthest carboxylic acid. If the carbon chain has an odd number of carbons, the keto-extended amino acid is identified as β-amino acid. The bond between β-carbon and γ-carbon is then broken, and a carboxylic acid is added to the β-carbon to create the β amino acid. If the carbon chain has an even number of carbons, the keto-extended amino acid is identified as α-amino acid. The bond between α-carbon and β-carbon is then broken and a carboxylic acid is added to the α-carbon to create α-amino acid.
Figure 5:
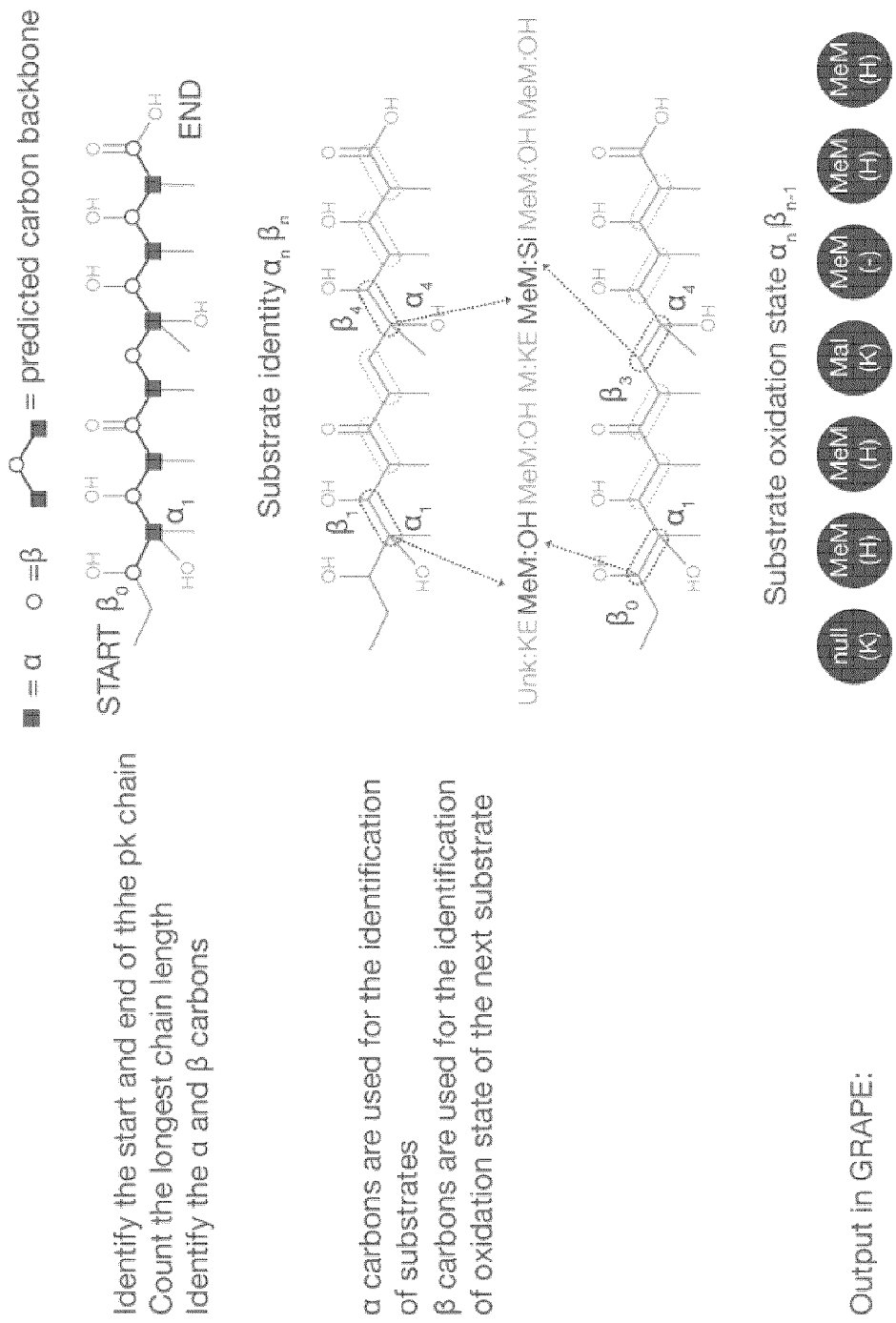
FIG. 5 is a visualization of polyketide carbon walking. GRAPE finds the biosynthetic end carbon (carboxylic acid carbon) and is then able to find the biosynthetic start carbon by locating the furthest carbon away that is in a carbon only chain (no other intermediate atoms) and is not terminal. If the furthest atom away cannot be a β carbon (incorrect number of carbons in the chain) the second furthest away carbon is then used. The states of each α and β carbon are analyzed for the substrate and oxidation state respectively.

Some compounds such as lipomycin and jamaicamide contain amino acids that have been decarboxylated and elongated through polyketide biosynthetic machinery; the reaction mechanism for these structures is reversed, leaving identified amino acid and polyketide components (FIG. 4). Remaining structures are run through chemical checks to identify whether they resemble polyketides (FIG. 5). For these chemical pieces, GRAPE identifies the main polyketide carbon backbone, by first predicting where the biosynthetic end is located (often a carboxylic group), then finds the start carbon and iterates through the structure in a stepwise manner to identify each oxidation state and substrate.

GARLIC (Global Alignment for Natural Product ChemInformatics)

GARLIC is a computational tool that interfaces between PRISM and GRAPE results to provide missing data links between input/unknown gene sequences and input/unknown natural products based on computed and/or predicted molecular similarities. GARLIC can therefore also be invoked to interface between distinct PRISM outputs and/or distinct GRAPE outputs to equally provide effective comparative scales in assigning respective similarity scores between natural product and genetic cluster data sets.

When using GARLIC to interface between PRISM and GRAPE results, GARLIC, using genetic information, a monomer output of an amino acid sequence of a peptide (amino acids) is provided from PRISM to obtain predicted natural products. On the other hand, using mass spectral chemical data a monomer output of an amino acid sequence is provided from GRAPE. Using GARLIC, the monomer sequences outputted from PRISM and the monomer sequences outputted from GRAPE are aligned and a match score is given to automatically determine how well these two independently determined monomer (amino acid) sequences align.

This match scoring allows the validation that either GRAPE can be used to determine the amino acid (molecules) sequence of natural products from mass spectral chemical data or that PRISM can be used to determine the amino acid (molecules) sequence of natural products from genetic sequences.

Accordingly, GARLIC was developed to identify the similarity between GRAPE and PRISM output. GARLIC is an algorithm that assigns a match score between GRAPE and PRISM output. (FIG. 6) PRISM and GRAPE each output two major components: an ordered sequence of monomeric units corresponding to assembly line modules, and a list of enzymes or chemical modifications that are external to the biosynthetic assembly line. GARLIC computes a similarity score between GRAPE and PRISM output using a global alignment score, computed using the Needleman and Wunsch algorithm. Since biosynthetic gene clusters may consist of assembly line PKS and NRPS encoded on multiple open reading frames, GARLIC first finds all permutations and returns the score corresponding to the best-matching permutation. If there are too many permutations to search all space in a reasonable time, a random sample is taken, and the top scoring alignments are taken and reordered, this is done several times, getting closer to the true alignment while searching a fraction of the permutable space.

Information external to the assembly-line sequence is matched between PRISM and GRAPE outputs, then added to the score. We identified a list of biosynthetic features external to the assembly line (FIG. 45). Tailorings such as sulfonations, halogenations, and sugars are matched by the enzymes from the cluster and the potential enzymes for the specific tailoring and for each sugar found in GRAPE the potential genes are combinatorialized and matched. The overall detected type of molecule (such as type 2 polyketide, or enediyne), can be matched to PRISM results, as PRISM also predicts the type of molecule based on known genes responsible for that scaffold. Adding scores in this manner are particularly important for type 2 polyketides, and enedyines whose scaffolds are not broken down by GRAPE to yield monomers.

Global Computational System and Processes

As previously noted, presented herein is a system which links gene sequences and their gene clusters to known and predicted natural products using various computational tools, in a preferred embodiments, based on the alignment of gene sequence analysis engine (i.e. PRISM) outputs and natural product analysis engine (i.e. GRAPE) output via a molecular alignment engine (i.e. GARLIC) which, using effective similarity scales, can rapidly output predicted cluster/product-related pairs amenable to the identification of new (i.e. unique) natural products of interest, amongst other functions.

Figure 33:
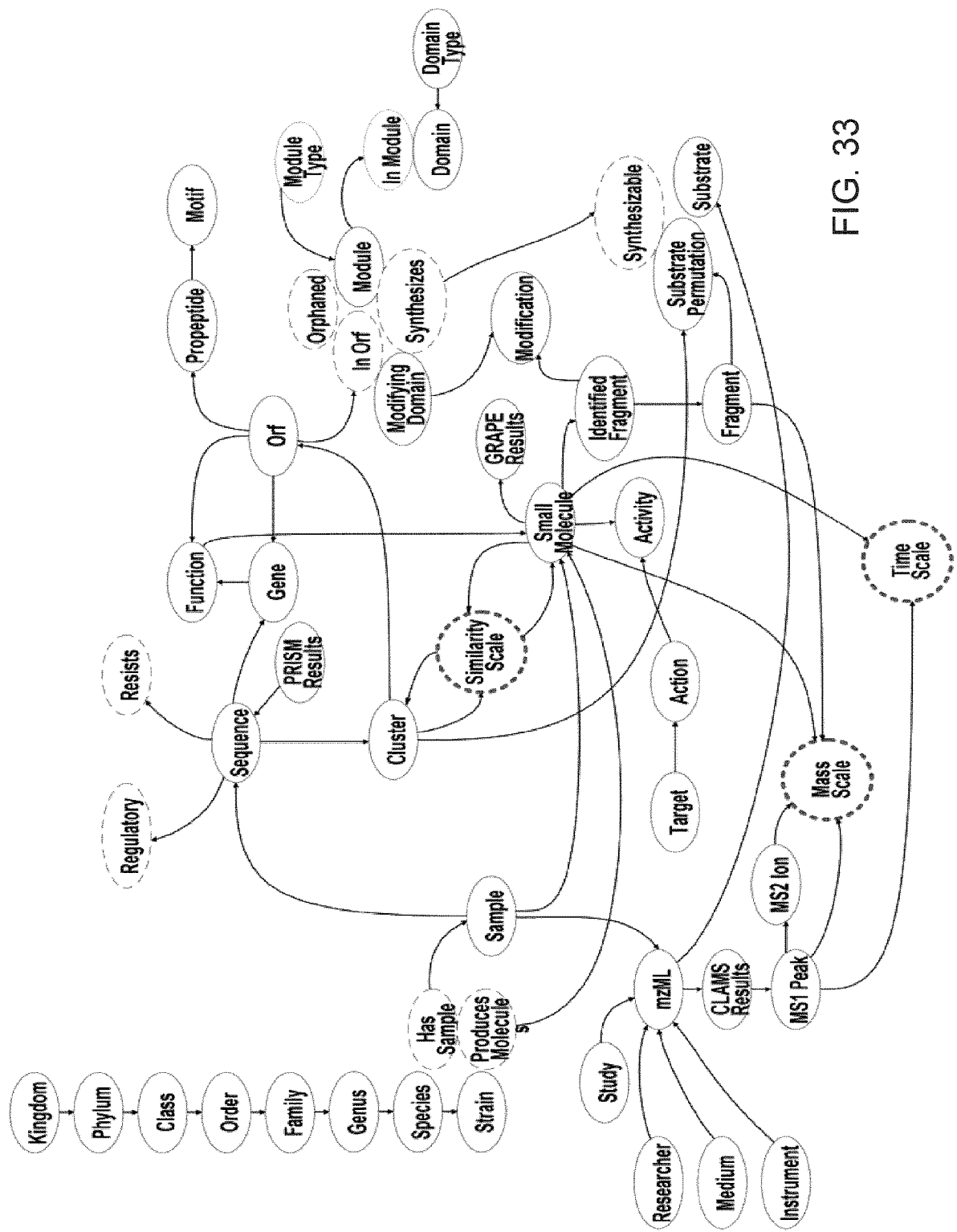
FIG. 33 shows an overall data system architecture for linking gene clusters and natural products, in accordance with one embodiment.

With reference to FIG. 33, a natural product analysis and discovery system will now be described within the context of a graphically illustrated data system architecture and processing implementation, interchangeably referred to herein as the Graph. The Graph is generally represented by a series of entry nodes (solid ovals), non-enterable nodes (dashed ovals) and scales (dotted circles). Generally, the non-enterable nodes define nodes that are intrinsically linked to a single node that it is touching in the schema (e.g. "produces molecules" and "has sample" are respective nodes intrinsically linked to any taxonomy node from "Kingdom" to "Strain"). These non-enterable nodes allow standard connections between different node types so the user or subsequent algorithms don't need to know which taxonomic level they are on, but can get samples or small molecules for them. These generally represent lower level tools for optimization and schema simplicity. In the taxonomy example, the schema is readily capable of going from any taxonomic level to getting the small molecules for them, or the samples, regardless of the taxonomic level. The person of ordinary skill in the art will readily appreciate the utility of such nodes, and their possible alternatives, within the present context.

As shown in the example of FIG. 33, the platform shows the different types of data that can be interconnected in a novel configuration to provide the various features, functions and outputs described herein, in accordance with different embodiments.

On the one side, metabolomics information may be input, captured, accessed and/or stored, in one embodiment, based first on raw metabolomic data (MZML). Such data may be actively acquired and input or otherwise provided or accessed from various available natural product resources and libraries. Associated with the MZML, meta information related to the processing of the MZML may also be accessed, produced and/or stored, in this example, via a Computational Library for the Analysis of Mass Spectra Data (CLAMS), described in further detail below. Generally, each CLAMS results will encompass hundreds of thousands of spectrometric peaks (ms1_peaks), each one representing a single metabolite associated with a given input or stored digital sample. Initially, these will generally represent unknown small molecules, though downstream links may be formed to associate peaks and small molecules for further processing or investigation. In some samples, a given ms1_peak may also be associated with fragmentation information stored as ms2_ions.

On the other side, input, accessed or stored sequences represent genomic information related to a particular strain or like sample, from which unknown clusters may be automatically determined using a sequence processing engine such as PRISM, which can effectively predict the constituent clusters of a given sequence based on a stored or accessed library of genomic models and the like, as introduced above and further detailed below.

As detailed in the below examples, the platform may effectively establish reliable connections between small molecules and clusters by computed similarities stored via the platform's similarity scale, which, in the below example, invokes molecular similarity values computed, in a preferred embodiment, by a molecular alignment engine (i.e. GARLIC), that allows not only for the alignment of output chemical monomers, be they gene-cluster encoded chemical monomers output from a gene sequence analysis engine such as PRISM and/or deconstructed natural product-related chemical monomers output form a natural product analysis engine such as GRAPE. Namely, these scales allow the platform to compute, access and/or store similarity information between clusters and small molecules, as well as inter-cluster similarities and inter-product similarities.

In the illustrated implementation, each small molecule and cluster has it's own scale. Each scale constitutes a connection of nodes, where each has a value (e.g. 0.1, 0.2, 0.3, 0.4, 0.5, . . . ). Other small molecules and clusters are connected to a node on the scale based on their similarity score. Using this approach, the similarity of these data types can be graphically illustrated, so to efficiently determine what clusters/compounds are similar to one another, irrespective of the data's origin, original format and type.

As noted above, a mass scale is also included that connects to anything within the system with a mass (known or predicted), so to effectively identify elements sharing similar masses.

Accordingly, the platform encompasses three major interconnected data types: Small molecules which are connected to clusters via their pieces (fragments) and overall similarity score (e.g. as computed via GARLIC); and are connected to peaks via their fragments and mass to the peaks. Likewise, clusters are connected to peaks by their predicted molecular masses and also by predicted fragments and ms2 ions (and comparable to other known or predicted natural products via the mass scale).

In one example that invokes an overall analysis, a single strain is first sampled to determine which ms1_peaks are associated with each of the strain's clusters. Other known strains are also identified that have similar clusters (i.e. via the similarity scales), and their ms1_peaks used to find common peaks. Other known strains that do not share similar clusters can also be considered to identify common peaks, so to remove such common peaks from the analysis. As one may expect, the number of peaks involved at this step are in the millions, but this comparison can be executed using the illustrated implementation in a matter of seconds on a single thread on one of the system's servers.

With the remaining peaks, the system can automatically identify known peaks by checking if the mass of a given peak matches that of a small molecule (including adducts). The system can also invoke similarities between the small molecule and the cluster to assess how well they match. For relatively poor matches, peaks can be disregarded (i.e. filtered out). Peaks can also be directly compared to the cluster fragments and predicted masses to see how well they match. In the end, the system can compile the clusters for a given strain, where each cluster has a list of candidate peaks and candidate small molecules. The small molecules can also be linked to their activity and target, which information can be used by the system to identify clusters with a potential activity/target.

Figure 34:
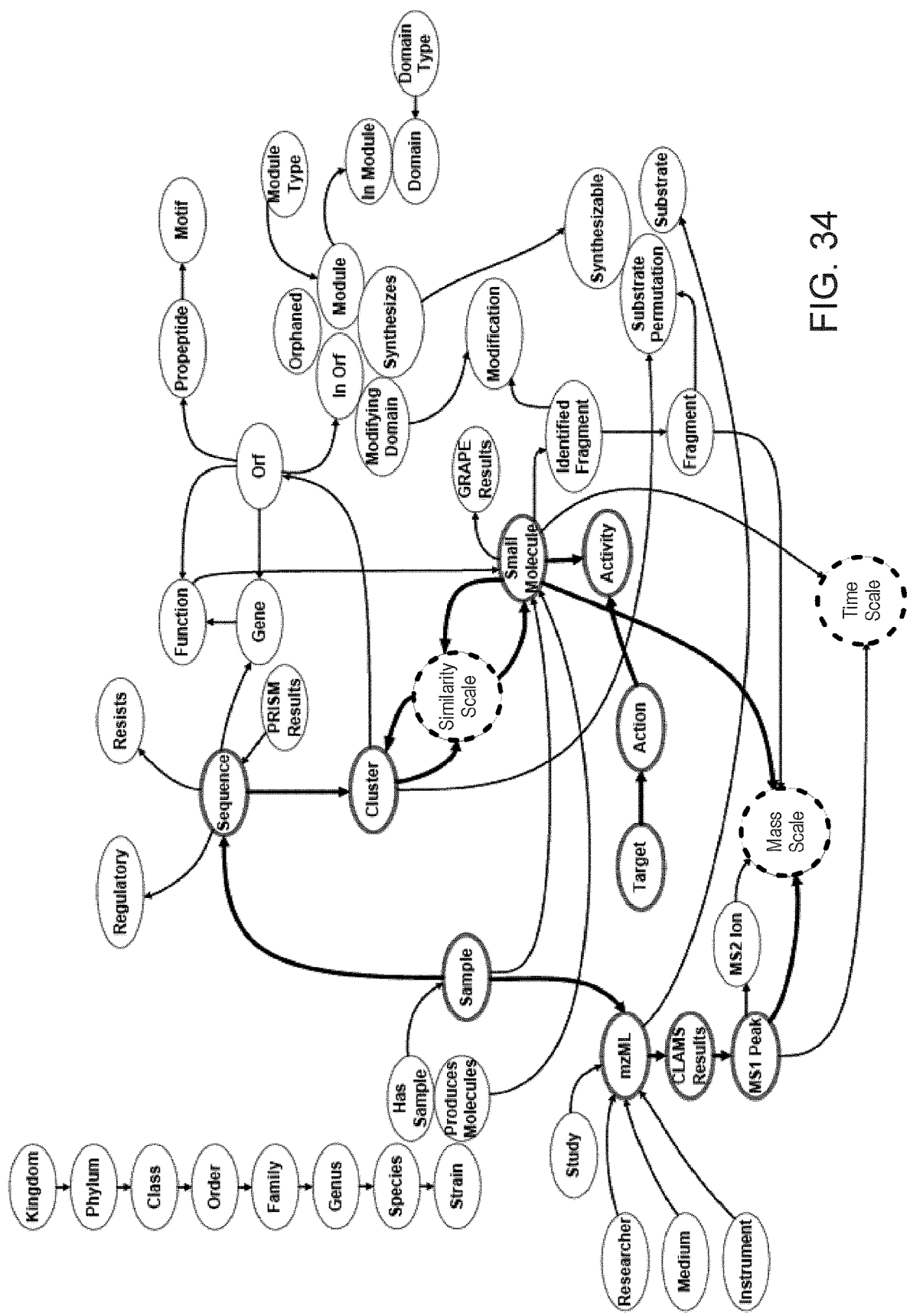
FIG. 34 shows the architecture of FIG. 33 showing in bold Inducer-to-Small-Molecule Relationships for linking gene clusters and natural products.

With reference to FIG. 34, inducer-to-small-molecule relationships are highlighted, in accordance with one illustrative application of the system. For example, a particular sample may be invoked which corresponds with a sample sequence itself linked (e.g. via PRISM results) to a set of constituent clusters. A similarity scale may then be invoked to identify other samples that may share similar clusters, for example, based on previously stored or sampled sequences and constituent cluster relations, or again based on previously or newly sampled chemical structures (small molecules node) predictably encoded by similar clusters. Accordingly, identified sample clusters may be automatically identified to correspond with known clusters and/or structures that may themselves be associated with known natural products. Likewise, unique or rare clusters may also be positively identified as forming part of the sample, thus identifying potential target clusters that may be desirably matched with predicted chemical structures and new natural products (i.e. previously observed and stored natural compounds whose potential bioactive value as a natural product has yet to have been investigated).

Conversely, a sample this time corresponding with raw metabolomics data (MZML) can be logically linked through results from CLAMS associating a set of mass spectrometry peaks with the sample. Respective mass and retention time scales may then be invoked (selectively, concurrently and/or sequentially) to identify other samples that may share similar peaks, for example, based on previously stored or sampled products and their associated peaks, or again based on previously or newly sampled chemical structures (i.e. small molecules predictably encoded by previously identified clusters). Accordingly, identified sample peaks may be automatically identified to correspond with known peaks and/or molecules, and by extension known clusters, which may themselves be associated with known sequences. Likewise, unique or rare peaks may also be positively identified as being manifested by the sample, thus identifying potential target peaks that may be desirably matched with known or predicted chemical structures associated with clusters that may be used to efficiently produce new natural products.

Much like the mess peak analysis scale may act on mass spectrometry peaks, the scale may also or alternatively act on fragmentation information (ms2_ions) to provide similar or complementary links between a sampled metabolome and previously or newly identified small molecules. Generally, the mass scale will be considered to act on a mass spectral signature, which may encompass one or more of the above-noted characteristic types.

Target, action and activity nodes linking to the small molecules node may also contribute in identifying target peaks and/or clusters within the greater context of the above-described examples. For example, for a sample having a specific known activity, the small molecule results provided will be filtered to only show those small molecules known to share this particular activity.

Likewise, a number of other filters, such as a taxonomy filter may be invoked to further isolate results of interest to particular taxonomy characteristics that may be relevant to the downstream application of the identified products. Other result-filtering examples may readily apply, as will be appreciated by the skilled artisan, without departing from the general scope and nature of the present disclosure.

Figure 35:
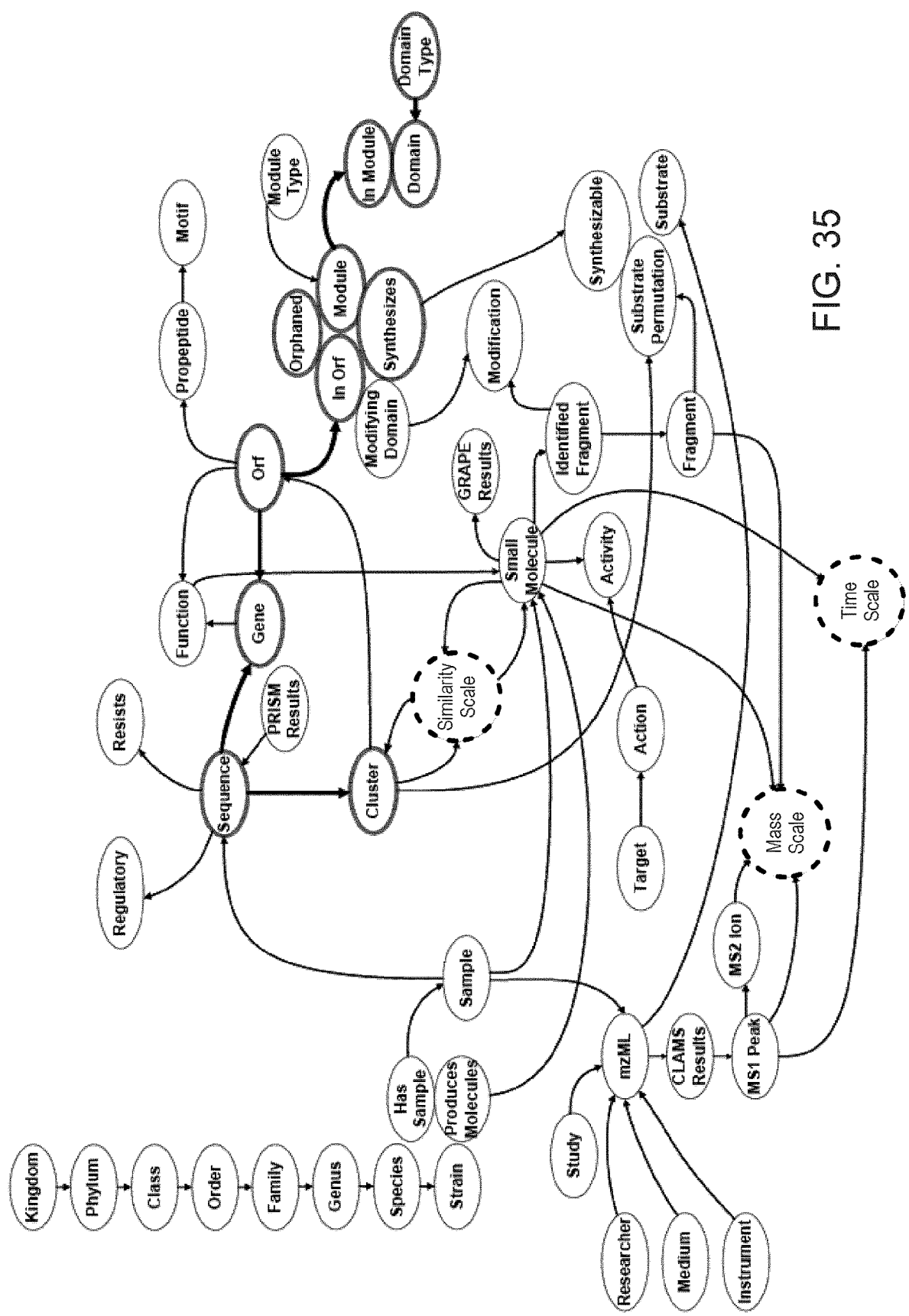
FIG. 35 shows the architecture of FIG. 33 showing in bold Regulator-to-Cluster-Type Relations for linking gene clusters and natural products.
Figure 36:
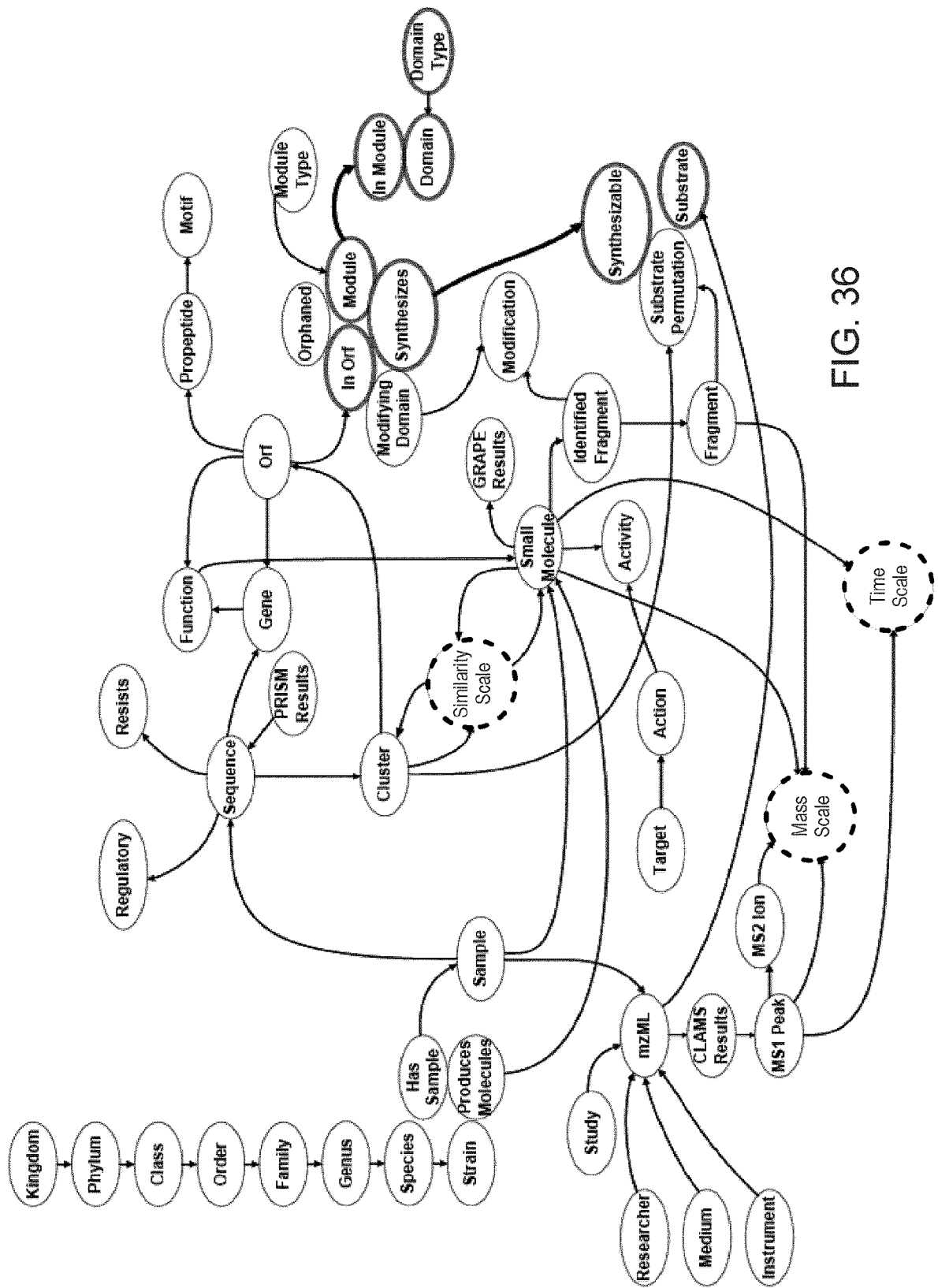
FIG. 36 shows the architecture of FIG. 33 showing in bold Regulator-to-Substrate-Relations for linking gene clusters and natural products.
Figure 37:
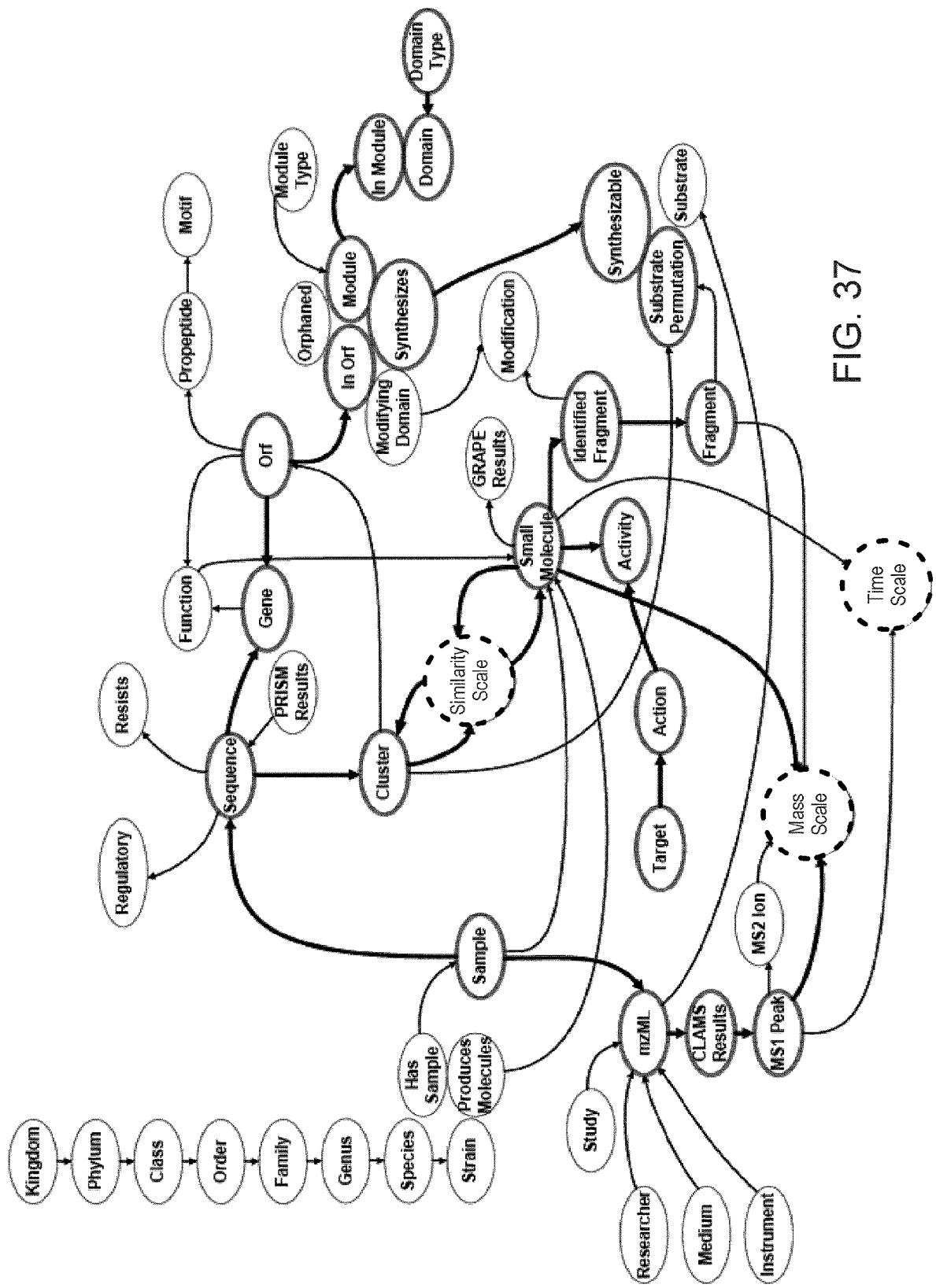
FIG. 37 shows the architecture of FIG. 33 showing all of the relationships used for linking gene clusters and natural products, in accordance with one embodiment.
Figure 38A:
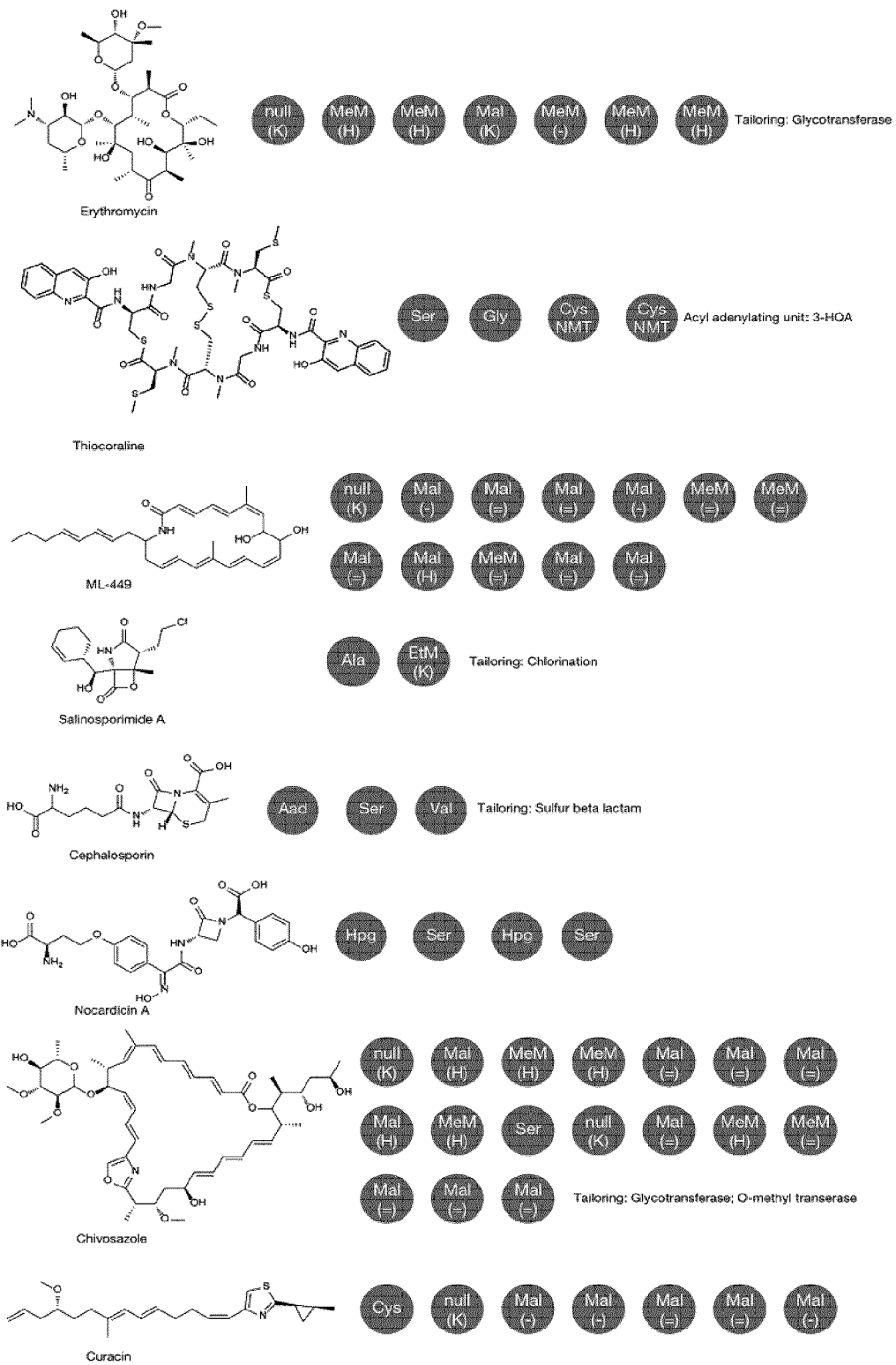
FIGS. 38A and 38B shows chemical structures corresponding to FIG. 43.
Figure 38B:
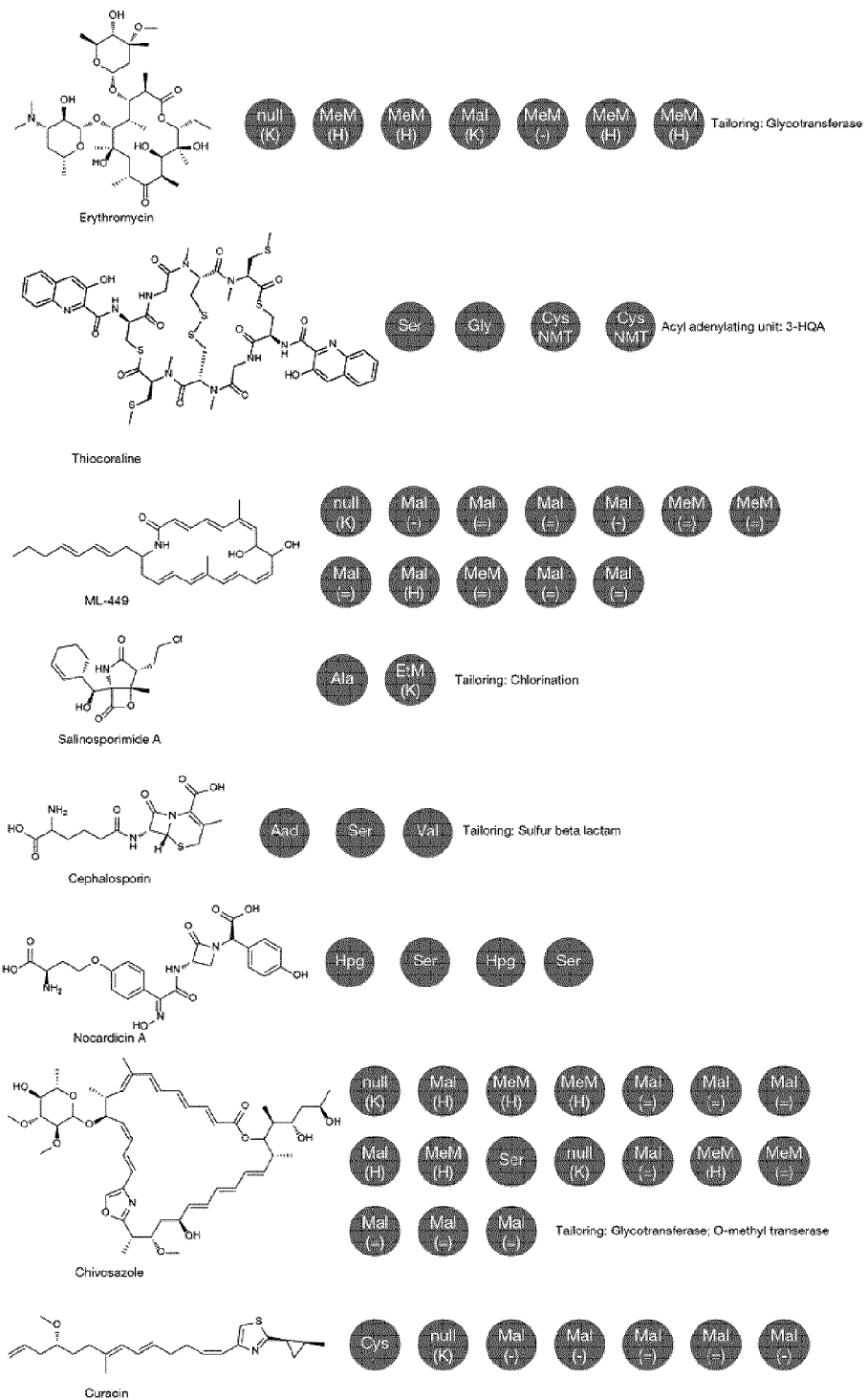
Figure 39A:
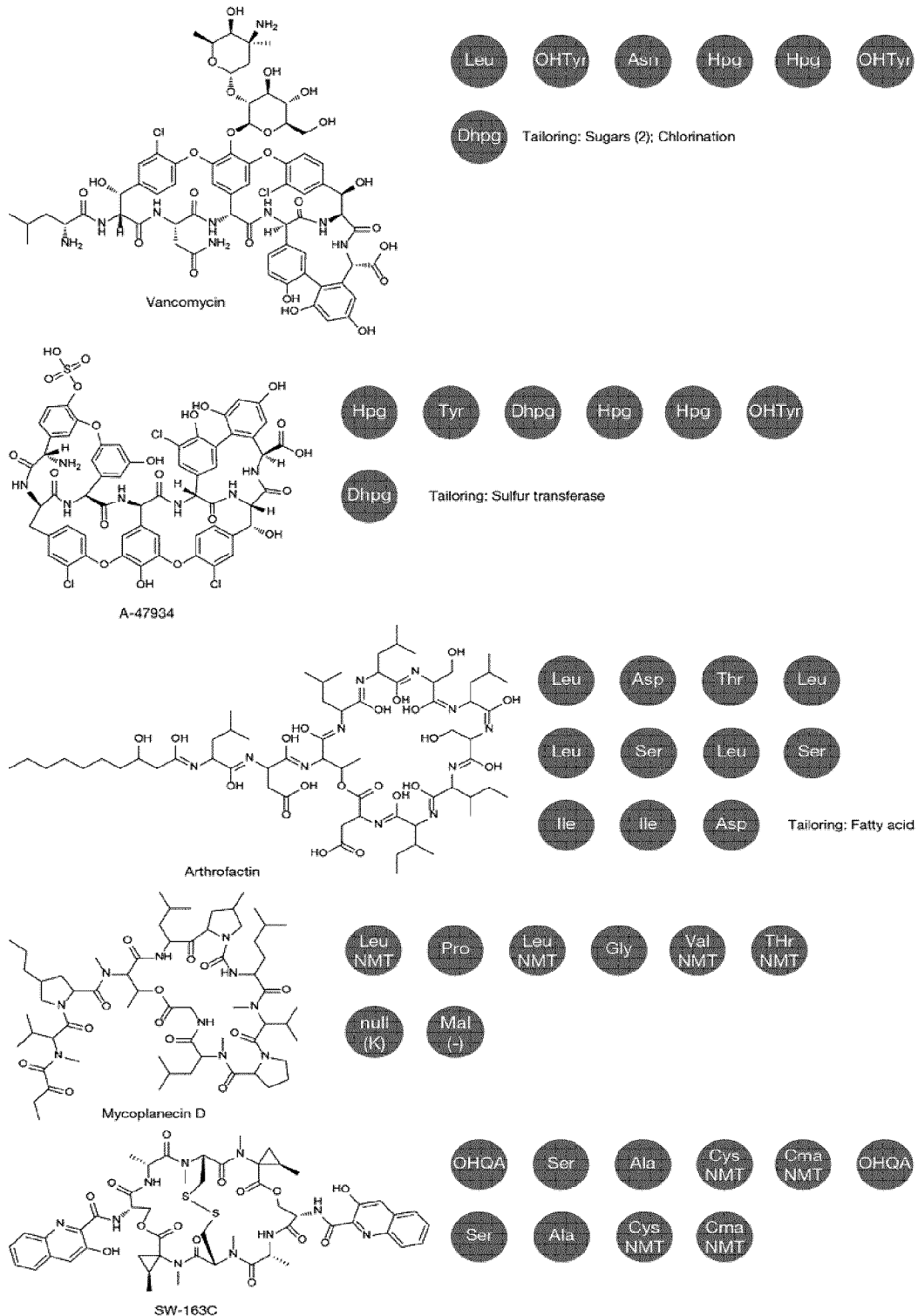
FIGS. 39A and 39B shows chemical structures corresponding to FIG. 44.
Figure 39B:
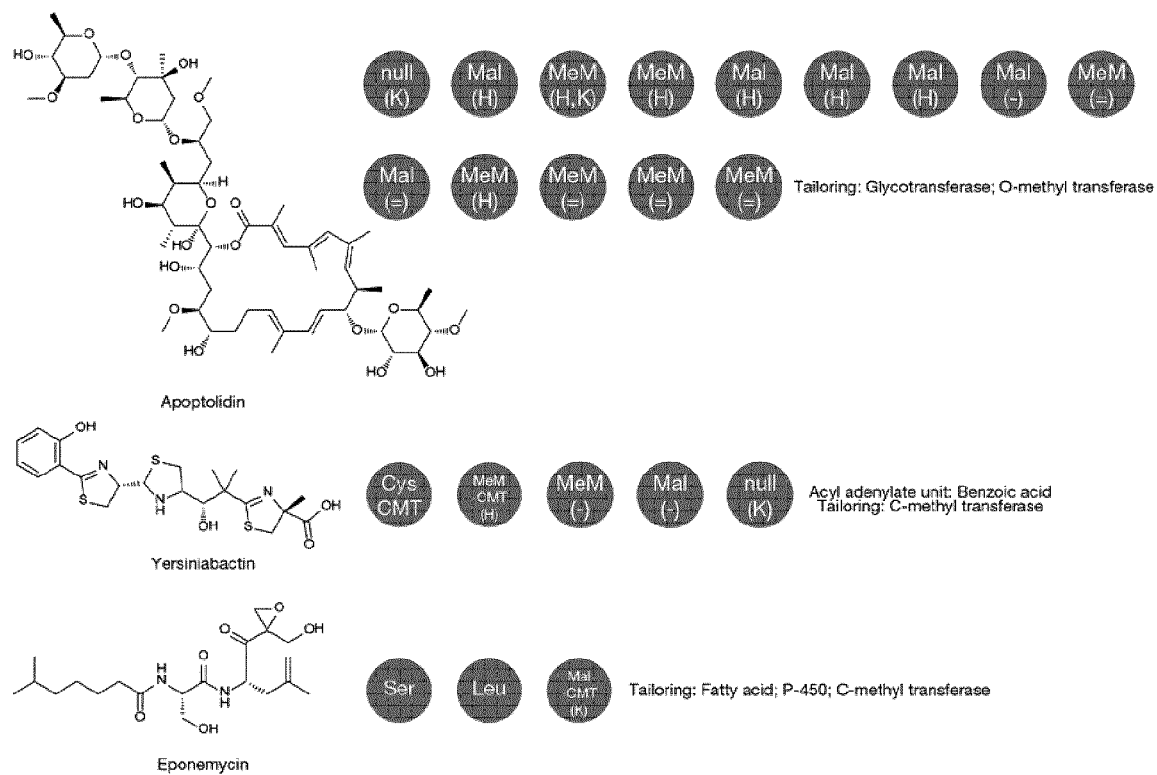

FIGS. 35, 36 and 37 show the Graph of FIG. 33 in which are shown in bold Regulator-to-Cluster-Type Relations, Regulator-to-Substrate Relations and overall relationships, including those bolded in FIG. 34 and described above, used for linking gene clusters and natural products, in accordance with one embodiment.

Figure 40:
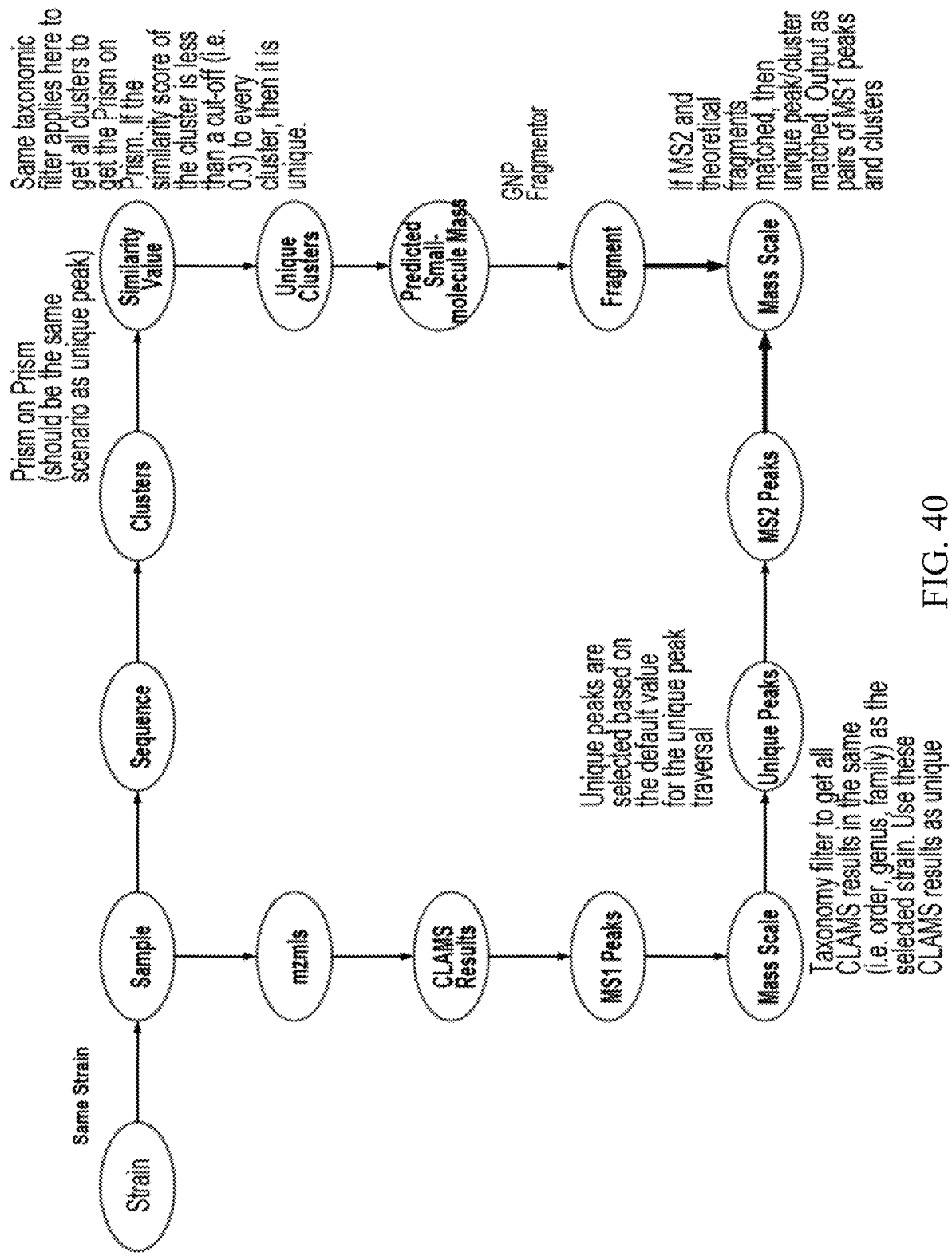
FIGS. 40 to 42 show exemplary logical flows through the system of FIG. 33, in accordance with one embodiment.

With reference now to FIG. 40, an exemplary logical flow through the system of FIG. 33 will now be described in which unique clusters and peaks can be positively linked in the identification of new natural products of interest derived from a same sample strain. In this example, a sequence associated with the sample strain is processed (i.e. via PRISM) to identify a set of constituent clusters, as well as a respective set of chemical monomers (i.e. encoded amino acids) and a respective chemical structure that is predictably encoded by each cluster. Each constitutent gene cluster can then be aligned with all previously stored or accessible clusters via the similarity scale (e.g. GARLIC) and attributed a corresponding similarity score.

Where a particular cluster scores a similarity score below a preset similarity threshold (e.g. 0.3) as compared to all other clusters, this low-similarity cluster is retained as a unique constituent cluster of the strain. Again using the similarity scale, each unique cluster may also be predictably aligned with a predicted natural product composition containing the same or similar monomers and provide a likely match based on achieving a designated similarity score threshold.

Likewise, the predicted chemical structure encoded by each unique gene cluster can be associated with a spectral mass signature (peaks/fragments) comparable to other natural product mass spectral signatures via the mass scale.

Concurrently, metabolomic data derived from the same strain can be deconstructed and processed (e.g. through CLAMS) to output a deconstructed mass spectral signature having a set of characteristic peaks. These peaks can themselves be compared with all known peaks (e.g. via the mass scale for all stored or accessible peaks known for a same order, genus, family of the strain) so to identify relatively unique peaks. Associated fragmentation peaks may also be invoked for further downstream comparative purposes.

Once both unique cluster and unique peak data sets have been filtered down, as described above, the mass scale can be invoked to first identify matches, when used, between MS2 peaks and predicted fragments, and then match unique peaks and clusters (i.e. predicted peaks of unique clusters) for output. In doing so, the process will ultimately serve to identify and associate unique clusters and peaks as target pairs for identifying new natural products that may, given their previously demonstrated uniqueness, exhibit desirable properties, characteristics and/or bioactivities.

Figure 41:
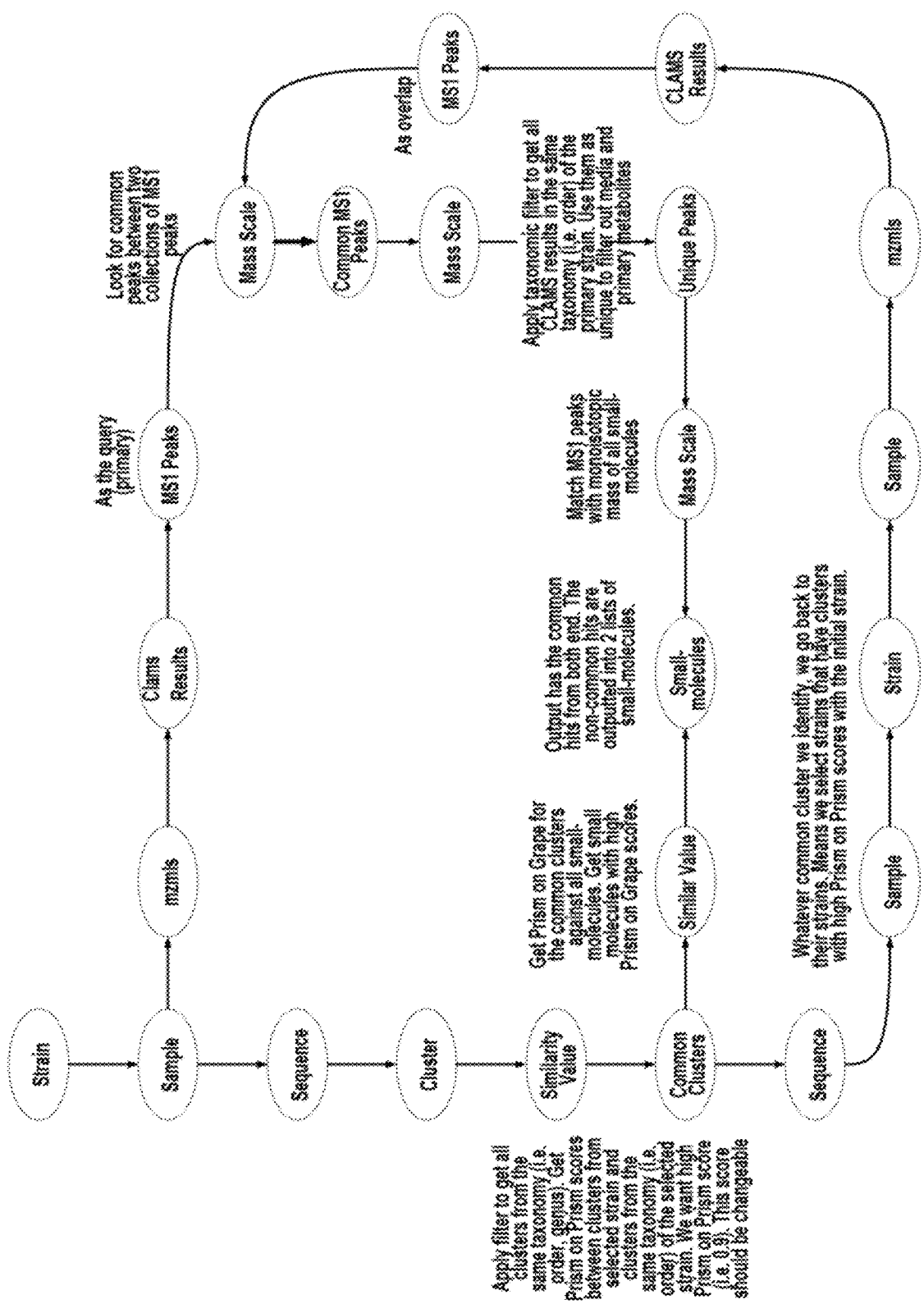

With reference to FIG. 41, another exemplary flow is illustrated. In this example, different collections of ms1_peaks as selected for comparison. The system first considers query peaks, which are the peaks from a strain/sample of interest. Then the system collects peaks from other samples/strains that it determines to not have the same cluster of interest as the query, and removes the common peaks (peaks that match on the mass and time scales, as well as by having a sufficient number of ms2_ions shared). The system then does the same, but opposite, function: it collects peaks from other samples/strains that it determines to have the same clusters via GARLIC prism/prism similarity and removes peaks that are not common between the two samples. In the end the system is reduced to a much smaller collection of 'peaks of interest' for a particular cluster. The system can then match those peaks via the mass scale to small molecules and determine if any of those small molecules have a sufficiently high GARLIC score to that cluster of interest. If so, it is retained as a very good small molecule candidate. Extending from this, the system can also use the ms2_ion information for peaks to see how similar peaks are to each other to find related peaks that make variant small molecules, leading to finding new small molecules that are variants of knows, or a new small molecule family.

Figure 42:
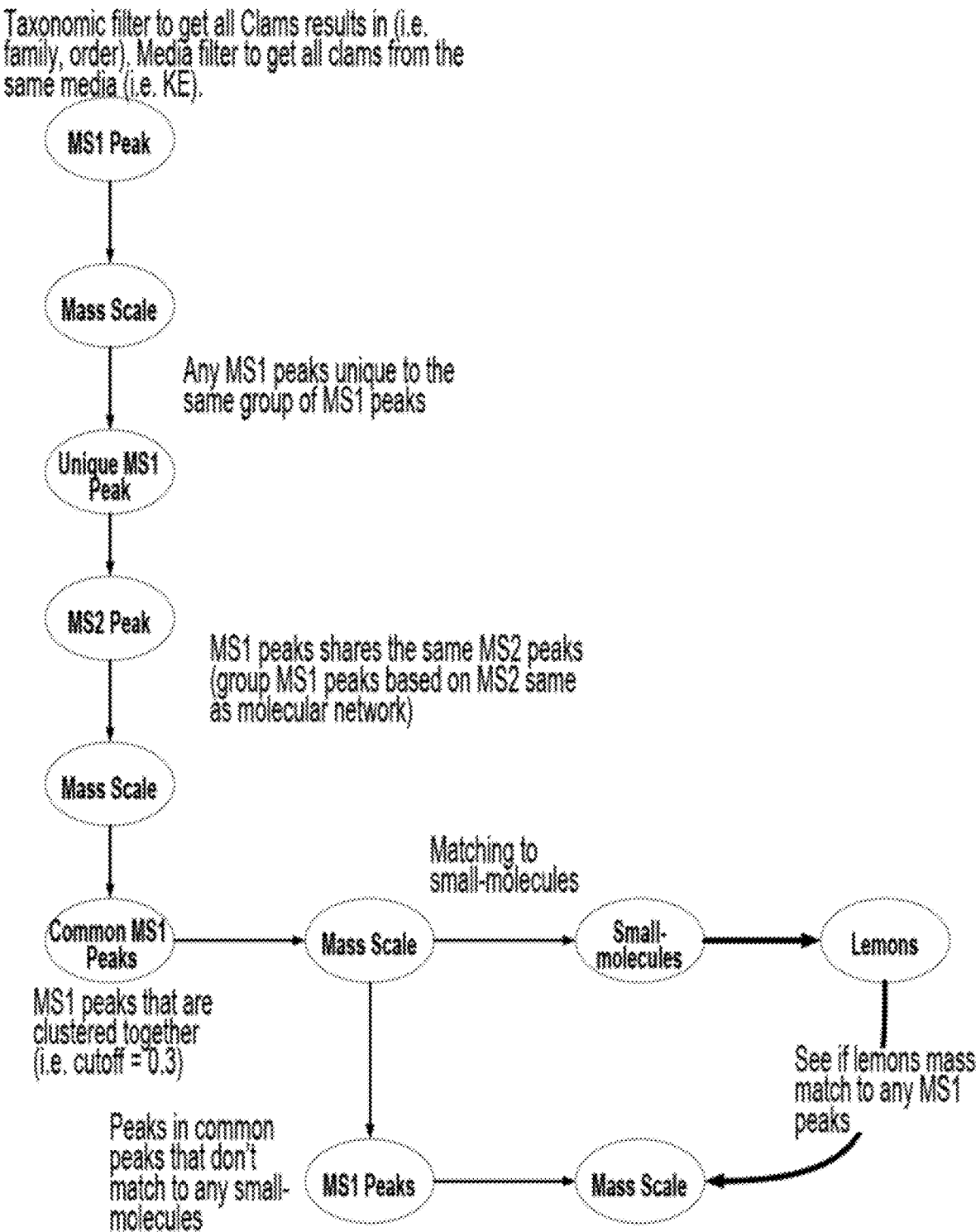

FIG. 42 provides yet another exemplary process flow application for isolating common and unique peaks and small molecules related to a given family, order, etc.

As will be appreciated by the skilled artisan, given the system architecture illustrated and described herein, different data processing paths and scales can be invoked to manipulate disparate data types from different sources in order to isolate products and clusters of interest for further investigation.

EXAMPLES

The following example illustrates various aspects of the scope of the invention. Specific elements of the example are for descriptive purposes only and are not intended to limit the scope of the invention. Those skilled in the art could develop equivalent methods and utilize comparable materials that are within the scope of the invention.

Example A

Predicting Ribosomally Synthesized and Post-Translationally Modified Peptide Natural Products from Gene Sequences The instant example illustrates exemplary experimental information for validating the prediction of natural products from gene sequences.

Validating the Accuracy of PRISM Structure Predictions for Known RiPPs

Having developed a comprehensive algorithm for RiPP structure prediction from genome sequence data, we sought to validate its performance on known RiPPs. We first investigated the accuracy of precursor peptide identification and cleavage. A reference dataset of 161 RiPPs with both known biosynthetic gene clusters and experimentally elucidated structures was assembled from the MiBIG repository. PRISM predicted cleavage sites for 157 of 161 RiPPs (97.5%). Among the four RiPPs without predicted cleavage sites, three were lasso peptides from clusters with multiple precursors. The xanthomonin A2 precursor was identified, but precursor cleavage was not predicted, while the caulosegnin III and sphingonodin I precursors were not identified. In all three clusters, at least one other precursor peptide was identified and correctly cleaved. The final RiPP without a predicted cleavage site was the class II lantipeptide lactocin S, whose unique precursor peptide peptide was identified but not cleaved. PRISM therefore generated predicted structures for 136 of 137 RiPP clusters (99.3%).

Figure 7:
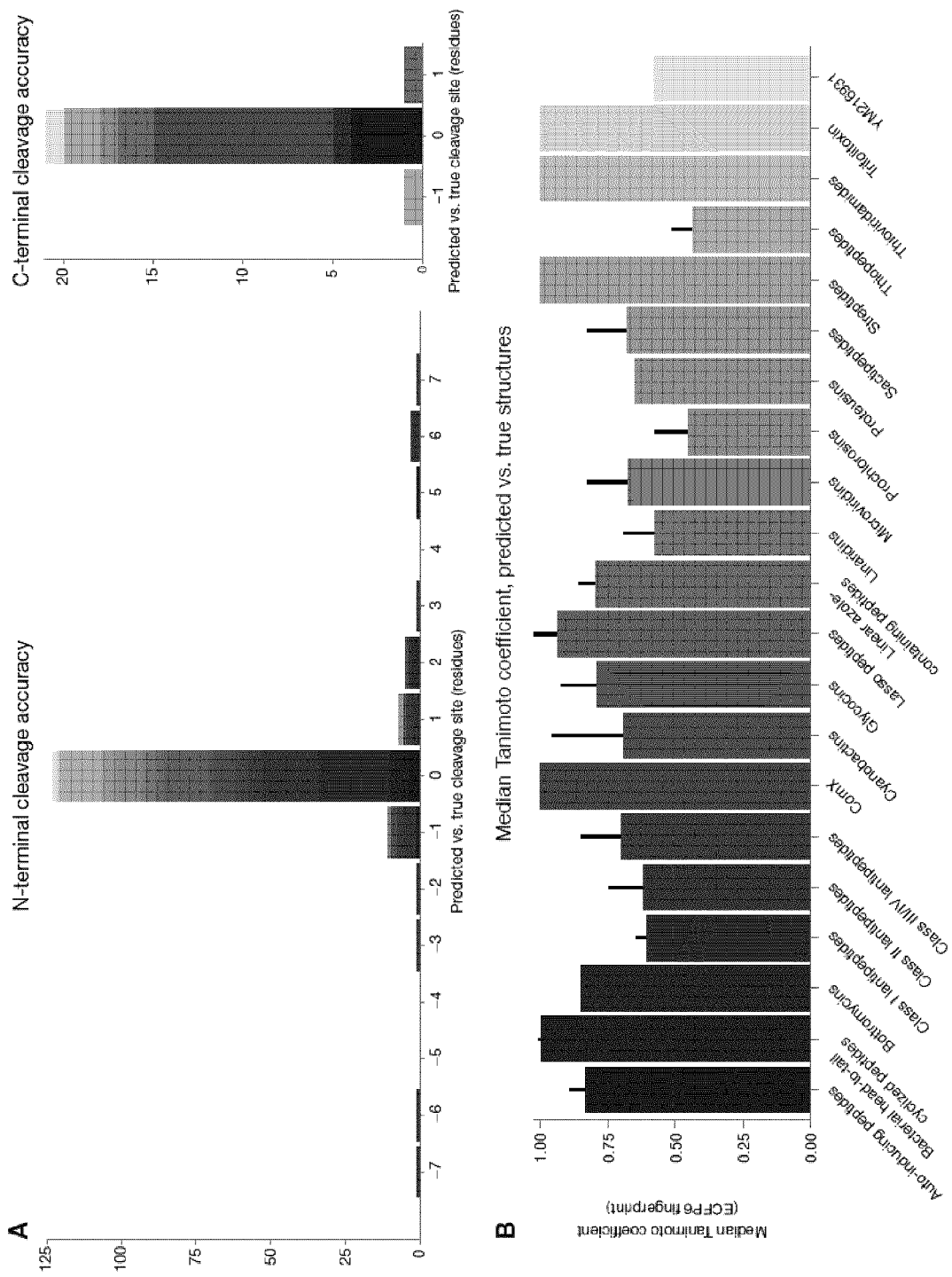
FIG. 7A is a plot of the distributions of the differences between true and predicted N- and C-terminal precursor peptide cleavage.
FIG. 7B is a plot of medium Tanimoto coefficient of predicted versus true structures.

Among precursor peptides with predicted N-terminal leader peptide cleavage, 124 of 157 (79.0%) were correctly predicted. A further 18, or 142 of 157 (90.4%), had predicted leader peptide cleavage sites within a single amino acid of the true cleavage site. Only 7 of 157 precursor peptides (4.5%) had predicted N-terminal leader peptide cleavage that differed by five or more amino acids from the true site. Among precursor peptides with C-terminal follower peptide cleavage, 22 of 24 were predicted correctly (91.7%), while predicted sites for the remaining two precursor peptides were within a single amino acid of the true site. The distributions of the differences between true and predicted N- and C-terminal precursor peptide cleavage are plotted in FIG. 7A.

Having determined that PRISM enables highly accurate precursor peptide identification and cleavage, we next examined the accuracy of its structure predictions, which leverage combinatorial library generation to elaborate post-translational modifications to the cleaved precursor peptide. We generated libraries of hypothetical structures for all 136 RiPP clusters, and compared true and predicted structures with the Tanimoto coefficient. We calculated the median Tanimoto coefficient from each hypothetical structure library (FIG. 7B), and observed an average median Tanimoto coefficient of 0.69±0.21, with a range of 0.43 to 1.0 for each RiPP family. Thiopeptides were the RiPP family with the lowest median Tanimoto coefficient, likely because of the extremely large combinatorial search space, as thiopeptide biosynthesis includes dehydration, heterocyclization and heterocycle oxidation, and pyridine formation at a minimum, and may additionally include heterocycle methylation, pyridine hydroxylation, esterification, and glycosylation, among other post-translational modifications. In fact, predicting thiopeptide structures within a reasonable computational time required extensive optimization of PRISM to permit random sampling from a biosynthetically plausible combinatorial search space. However, it is notable that the sparse ECFP6 chemical fingerprint generally produces low scores for any comparison of two structures which are not perfectly identical. Comparing the median Tanimoto coefficients for RiPP structure predictions to the median Tanimoto coefficients generated by PRISM for thiotemplated structures, which at approximately 0.25 currently represent the most accurate genomic structure predictions of NRPS and PKS products, provides a more subjective confirmation of the predictive accuracy of PRISM for genetically encoded RiPPs.

Figure 8:
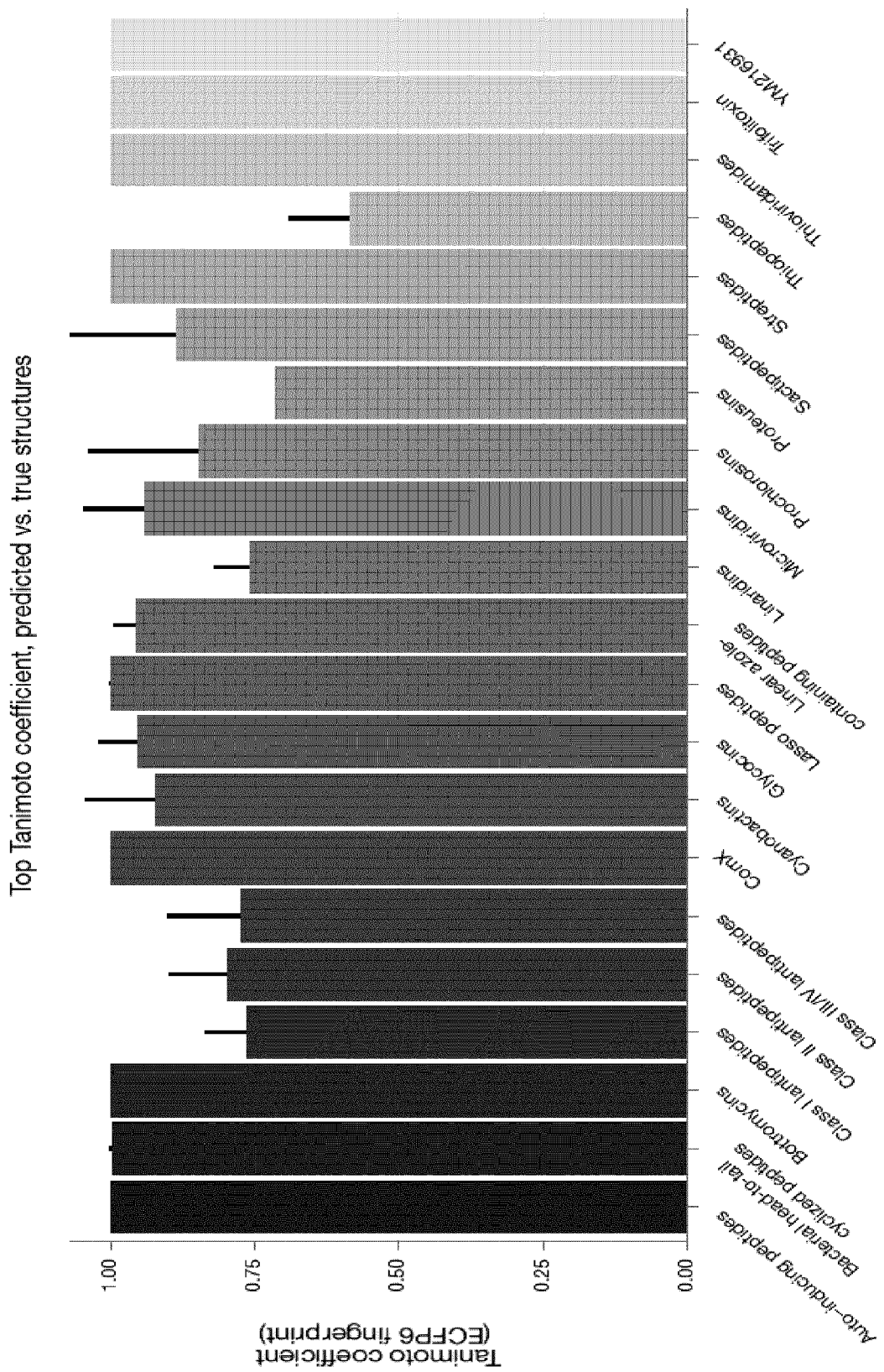
FIG. 8 is a plot of the top Tanimoto coefficients of predicted versus true structures.

We also calculated the single best Tanimoto coefficient from each hypothetical structure library, and observed a significant increase in the average Tanimoto coefficient for each class (p<0.02, Kolmogorov-Smirnov test; FIG. 8). The average best Tanimoto coefficient was 0.84±0.16, and ranged according to RiPP family from 0.58 to 1.0. These data suggest that, even in clusters where structure prediction based on the identified biosynthetic information involves a large combinatorial search space, PRISM is typically able to predict at least one structure with a high degree of chemical similarity to the true structure.

Global Analysis of Genetically Encoded RiPP Chemical Space

Having validated PRISM as a highly accurate method for genomic RiPP structure prediction, we used PRISM to chart the chemical space of genetically encoded RiPPs by analyzing the 65,421 microbial genomes listed on NCBI. PRISM identified 30,261 biosynthetic gene clusters encoding RiPPs (FIG. 9A). Among all microbial genomes, 19,113 (20.0%) contained at least one cluster, corresponding to 2,118 of 12,439 unique species. The genome of the average RiPP-producing organism contained 1.58±0.92 RiPP clusters, but significant variability was observed in biosynthetic potential. A small number of organisms were highly prolific, with 312 microbes (1.6%) producing five or more RiPPs. Three actinomycetes (*Streptomyces mobaraensis*, *Nonomuraea candida*, and *Streptacidiphilus albus*) produced eleven RiPPs, the maximum number of RiPP clusters observed in any single genome.

Figure 10:
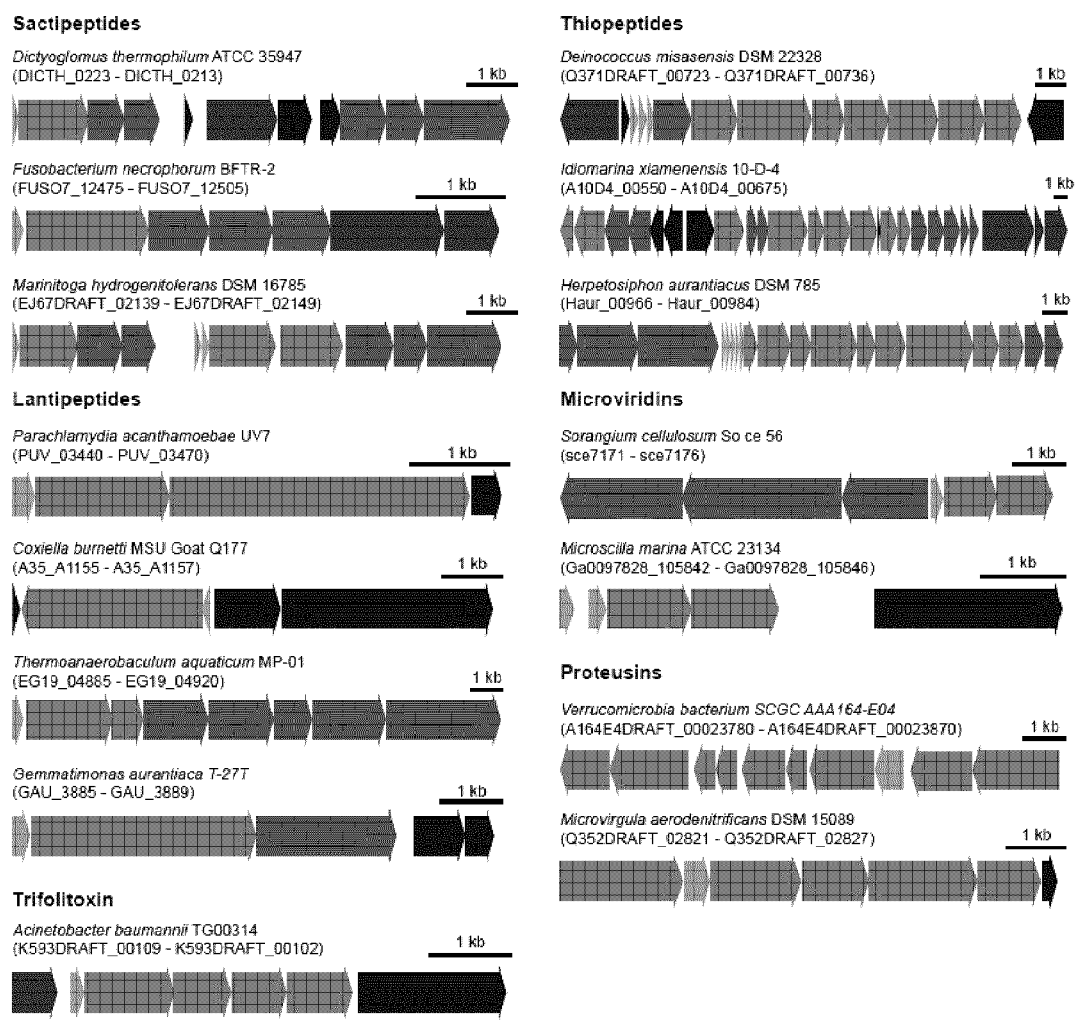
FIG. 10 is a visual representation of RiPP gene clusters.

Although Firmicutes and Actinobacteria were the most biosynthetically privileged phyla (containing 24,319 and 3,933 clusters, respectively) our results demonstrated that RiPPs are likely produced by nearly all bacterial phyla, including many that have never been known to produce natural products. We identified RiPP clusters in 17 of 33 non-candidate bacterial phyla with sequenced genomes, and failed to identify clusters only in sparsely sequenced phyla (i.e., with fewer than 50 genomes) and in the Tenericutes. Lantipeptides were the most widely distributed RiPPs, with clusters observed in 16 bacterial phyla and in Archaea. Moreover, while there exists to date only one example of a lantipeptide from a non-cyanobacterial Gram-negative organism (pinensin), we identified class I, II, and III/IV lantipeptide clusters throughout Gram-negative phyla, including Proteobacteria, Acidobacteria, and Gemmatimonadetes. We also identified lantipeptide clusters in unusual producers, such as the obligate intracellular pathogen *Coxiella burnetti*. Proteusins were previously known to be produced only by Cyanobacteria and species of the proposed Tectomicrobia phylum, but clusters were observed in Proteobacteria and in two sequenced isolates from the poorly described Verrucomicrobia phylum. Prochlorosins were surprisingly observed in a number of non-cyanobacterial families, including Alpha- and Deltaproteobacteria, as well as in Verrucomicrobia. Microviridins, another cyanobacterial family of RiPPs, were also found to be more widely distributed than previously appreciated, with clusters in a number of Proteobacteria and Bacteroidetes families. Sactipeptides, which were known to be produced only by Firmicutes, were distributed across Archaea and Bacteria, appearing in six phyla, including several not previously associated with natural product biosynthesis, such as Thermotogae, Fusobacteria, and Dictyoglomi. Chlamydiae had likewise never been appreciated as natural product producers, but several species were observed to possess clusters for class I and II lantipeptides. Trifolitoxin, a narrow spectrum antibacterial agent with activity against *Rhizobium* spp., was detected in multiple *Acinetobacter* isolates, indicating a potential ecological role for this human pathogen. Thiopeptides are promising antibacterial drug candidates which were previously only associated with Firmicutes and Actinobacteria. However, we observed thiopeptide clusters in a number of species from Proteobacteria, Chloroflexi, Bacteroidetes, and even Deinococcus-Thermus, a phylum previously considered devoid of natural product biosynthetic gene clusters. These results cumulatively demonstrate the surprisingly universal distribution of RiPP biosynthesis throughout the prokaryotic tree of life. We provide graphical representations of the clusters discussed in this section in FIG. 10.

Analysis of RiPP clusters revealed that the rarest RiPPs were YM-216391-family peptides (n=2), thioviridamide-family RiPPs (n=9), proteusins (n=9), and bottromycins (n=9) (FIG. 9A). Meanwhile, the most widespread families of RiPPs were auto-inducing peptides (n=8,741), lantipeptides (n=4,420, 4,373, and 6,074 for classes I, II, and III/IV, respectively), bacterial head-to-tail cyclized peptides (n=2,927), and lasso peptides (n=1,466) (FIG. 9A). However, many RiPPs are ubiquitous signalling molecules, such as the autoinducing peptides, and consequently it is likely that many of the identified clusters produce identical products. We therefore used PRISM structure predictions to identify clusters which produced unique RiPPs. Each of the 24,756 clusters for which PRISM predicted at least one structure were compared to one another to generate over 612 million Tanimoto coefficient matrices, representing about 13 TB of information. A master similarity matrix was constructed by assigning the value of the median Tanimoto coefficient between two libraries of predicted structures to each cluster-cluster comparison, except when the clusters contained at least one identical predicted structure, in which case a value of 1.0 was assigned to the comparison. In this method, highly similar RiPPs, such as the structural isomers epidermin and gallidermin, would be considered unique cluster products, while two clusters which encode the same RiPP with low sequence homology or a different enzyme ordering would not.

Tanimoto coefficient analysis of predicted structure libraries revealed 2,231 clusters producing unique RiPPs among the 24,756 clusters with at least one predicted structure (FIG. 9B). Strikingly, comparing the most abundant unique cluster products to the most abundant clusters revealed a significant reordering of RiPP families: lasso peptides, not autoinducing peptides, are the most abundant when clusters producing the same product are dereplicated. Unique thiopeptides, microviridins, prochlorosins, and cyanobactins are considerably more abundant than the distribution of their clusters had suggested. In contrast, autoinducing peptides, bacterial head-to-tail cyclized peptides, ComX, and streptides are more homogeneous than the distribution of their clusters would suggest. One likely explanation for this discrepancy is the frequent and repetitive sequencing of the producers of these molecules, which are often pathogenic or otherwise human-associated Firmicutes, including *Bacillus, Clostridium, Staphylococcus, Streptococcus*, and *Enterococcus*. Indeed, RiPPs of these families are rarely, if ever, observed outside of the Firmicutes, with our analysis identifying only 25 cyclized bacteriocins and 1 ComX molecule in non-Firmicutes producers; streptides and autoinducing peptides do not appear outside of this phylum. Similarly, linear azol(in)e-containing peptides are an example of a family of RiPPs with a broad taxonomic distribution, with producers in six bacterial phyla, but relatively few unique structures. The streptolysin and clostridiolysin toxins are broadly conserved throughout common pathogens and unrelated organisms, such as Chlamydiae. Of the 30 most common clusters producing the same product, observed between 110 and 3,697 times, all were from commonly sequenced human pathogens or laboratory strains, with 28 of 30 produced by Firmicutes.

Figure 11:
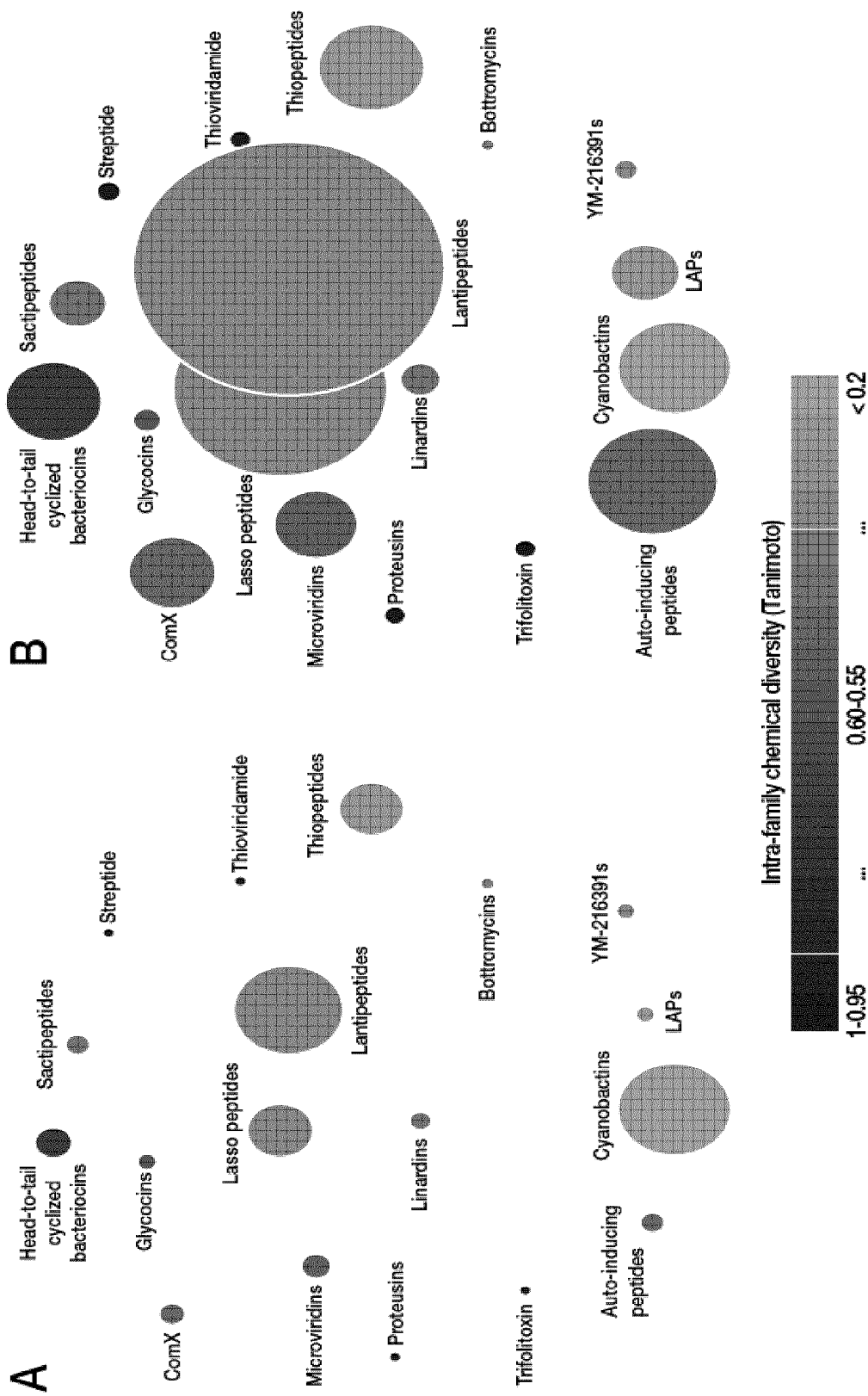
FIG. 11A is a plot of the chemical space of known RiPPs, with the size of each node corresponding to the number of known RiPPs of each family, and its colour corresponding to the within-family chemical diversity as measured by the average median Tanimoto coefficient.
FIG. 11B a plot of the chemical space of genetically encoded RiPPs.

We next used PRISM structure predictions to chart the chemical space of genetically encoded RiPPs, and compared it to the chemical space occupied by known RiPPs. A thorough review of the literature and both public and in-house databases revealed a set of 509 known RiPPs, which was used to generate a Tanimoto coefficient similarity matrix for known RiPPs. We then used principal component analysis to plot the chemical space of known RiPPs (Methods), with the size of each node corresponding to the number of known RiPPs of each family, and its colour corresponding to the within-family chemical diversity as measured by the average median Tanimoto coefficient (FIG. 11A). We subsequently used the Tanimoto coefficient matrix of structure predictions for 24,756 clusters to plot the chemical space of genetically encoded RiPPs (FIG. 11B).

Comparing the two reveals disparities between the number of known and genetically encoded natural products for many classes: in particular, the genetically encoded lantipeptides and lasso peptides vastly outnumber known products from these families. This analysis also highlights genetically encoded RiPP families with a low level of chemical diversity, such as bacterial head-to-tail cyclized peptides, trifolitoxins, thioviridamides, and streptides: these families of genetically encoded natural products are less likely to represent attractive pharmaceutical or industrial targets. Conversely, cyanobactins and thiopeptides demonstrated the highest within-family chemical diversity. This observation, combined with their broad distribution in organisms not previously known to produce these RiPPs, suggest these families are viable targets for discovery efforts.

These results also provide some insight into the number of RiPPs which remain undiscovered. Thorough investigation of the literature and both public and in-house databases revealed a set of 510 known RiPPs, but Tanimoto coefficient analysis revealed 2,231 unique cluster products. Removing congeners produced by the same cluster reduced the size of the set of known RiPPs to 398. Our analysis therefore suggests that at least 1,833 of 2,231, or 82% of genetically encoded RiPPs remain unknown if all known molecules are currently present in sequenced genomes. However, many known RiPPs were obtained from environmental isolates and other organisms without sequenced genomes, and therefore would not have been detected in this analysis. Thus, the figure 82% is more likely to represent a conservative lower bounds for the percentage of undiscovered RiPPs than a truly accurate estimate, emphasizing our finding that the vast majority of genetically encoded RiPPs remain unknown.

Leveraging Accurate Structure Prediction for Genome-Guided RiPP Discovery

We finally sought to demonstrate the potential of the highly accurate structure predictions generated by PRISM to facilitate the targeted, genome-guided discovery of novel RiPPs. Bioinformatic analysis revealed that natural products of the YM-216391 family were among the rarest RiPPs, with only two biosynthetic gene clusters identified in a sample of 65,421 genomes. Tanimoto coefficient matrix analysis suggested that neither cluster product was identical to any of the three known members of this family, which include urukthapelstatin and mechercharstatin in addition to YM-216391, the sole representative with a sequenced cluster. All three products are characterized by nanomolar cytotoxicity and a conserved, azole-rich macrocyclic structure. Putative YM-216931 family clusters were identified in the genomes of *Streptomyces aurantiacus* JA 4570 and *Streptomyces curacoi* DSM 40107. Because *S. aurantiacus* JA 4570 has been the subject of intense investigation over the past two decades, and is known to produce at least three distinct classes of natural products with diverse activities, we reasoned that it would be a useful target to demonstrate the utility of our approach.

Figure 12:
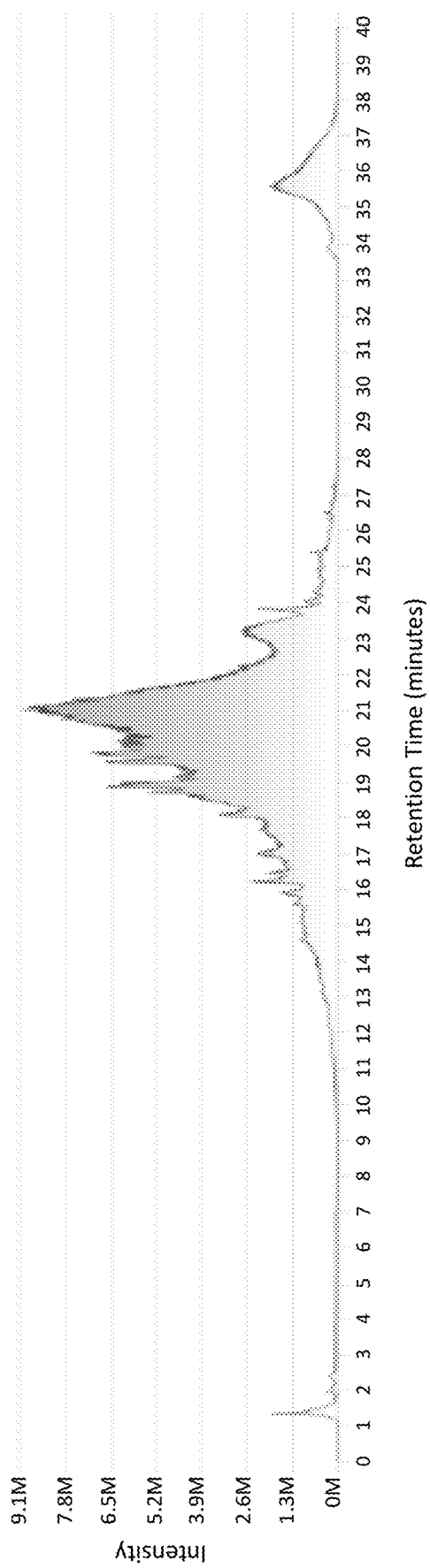
FIG. 12 is a plot of Computational Library for the Analysis of Mass Spectra (CLAMS) results.

We leveraged PRISM structure predictions to identify natural products within bacterial extracts by developing CLAMS (Computational Library for the Analysis of Mass Spectra), a tool for LC-MS chromatogram analysis. Using the CLAMS web interface, LC-MS chromatograms are searched with a library of PRISM predicted structures to identify corresponding high-resolution masses (FIG. 12). *S. aurantiacus* was cultured in a panel of 20 media for three days before cell pellets were collected and extracted with organic solvent, which was then processed using high resolution liquid chromatography-coupled mass spectrometry (HR-LC/MS). Chromatograms from each of the media conditions were analyzed using CLAMS, loading the library of 15 predicted structures for the putative *S. aurantiacus* YM-216391 family cluster. A predicted structure was only identified in one media condition and at an extremely low concentration, with a mass consistent with the fully oxidized azole ring system of predicted scaffold #13, which was named aurantizolicin. MS/MS fragmentation displayed the predicted tandem isoleucines, and incorporation of deuterium-labelled phenylalanine ($d_8$-Phe) demonstrated incorporation of five deuterium atoms (with the other three being lost during hydroxylation, heterocyclization, and aromatization). Culture conditions were serially optimized for production, culminating in a large culture effort to isolate sufficient quantities of aurantizolicin to confirm the predicted structure with NMR spectroscopy. As expected, aurantizolicin possesses a number of conserved and highly predictable features unique to this small class of RiPPs, and is closely related to YM-216391, with nearly identical NMR chemical shifts. Like other RiPPs of this family, aurantizolicin is produced in extremely small quantities, and consequently was not discovered despite previous bioactivity-guided studies. However, its identification by PRISM and CLAMS indicates our platform can be leveraged towards the targeted discovery of novel, genetically encoded RiPPs.

Discussion of the Results of Example A Presented Above

Microbial natural products are an evolved resource of bioactive metabolites that are essential to the treatment of many diseases. In recent years, analysis of the growing resource of microbial genome sequence data has revealed that the majority of natural products remain undiscovered, and consequently, a number of tools have been developed to facilitate the targeted discovery of novel natural products from genomic data. However, the structural and biosynthetic diversity of RiPPs has to date precluded the development of a comprehensive platform for the analysis of genetically encoded RiPPs. In this work, we present the first such platform, and leverage it to conduct a systematic investigation of RiPP biosynthesis in over 60,000 genomes. Our analysis demonstrates the nearly universal distribution of RiPPs throughout the prokaryotic tree of life, failing to identify RiPP clusters only in non-candidate bacterial phyla with fewer than 50 sequenced genomes and the Tenericutes. We also observed the surprisingly widespread taxonomic distribution of many RiPP families thought to be produced by only one or two phyla, including prochlorosins, microviridins, and cyanobactins, and identified RiPP clusters in several phyla that had not previously been known to produce natural products. We leveraged accurate structure predictions to chart the chemical space of genetically encoded RiPPs, dereplicating clusters which produce the same products and ranking RiPP families according to their chemical diversity. Our analysis indicates that the vast majority of RiPPs remain undiscovered, and provides a lower bounds for an estimate of the number of unknown RiPPs. Finally, we use the highly accurate structure predictions of our bio- and cheminformatic platform to identify and isolate a novel member of the smallest family of RiPPs, those related to the cytotoxic peptide YM-216391.

Several tools or methods have previously been developed to facilitate genome-guided discovery of novel RiPPs, but existing methods suffer from three primary limitations: they have often been limited to a single family of RiPPs; they are incapable of structure prediction; and they generally require a high degree of manual annotation. For instance, Maksimov et al. used a combination of heuristic precursor identification and motif-guided identification of biosynthetic enzymes to mine 3,000 genomes for lasso peptides, and identified a novel lasso peptide astexin-1, but their approach was limited to this family of RiPPs. Similarly, Marsh et al. searched for homologs of the NisB and NisC proteins to identify 49 class I lantipeptide clusters, but their procedure required manual inspection for precursors, manual identification of known clusters, and manual removal of false positives. Efforts capable of genome mining for RiPPs of multiple classes have often been limited by the high degree of manual annotation required to identify clusters. For instance, Letzel et al. used a set of three bioinformatics tools and BLAST searches to mine the genomes of 211 anaerobic bacteria for six families of RiPPs, but could not generate predicted structures or match clusters to unique products except by manual annotation. Likewise, Cox et al. used YcaO proteins to identify thiazole/oxazole-modified macrocycles (TOMMs), a superfamily encompassing members of linear azol(in)e-containing peptides, cyanobactins, thiopeptides, and bottromycins, and identified nearly 1,500 clusters; however, their method required extensive manual annotation.

Several automated platforms for RiPP genome mining exist, increasing the throughput of RiPP genome mining, but these, too, are often limited to a single family of RiPPs. The widely used antiSMASH platform, for instance, is capable of identifying putative lantipeptide clusters and predicting their cleavage sites, but not of generating predicted structures nor of identifying other classes of RiPPs. Cimermancic et al. developed a machine-learning algorithm, Cluster-Finder, to identify clusters of both known and unknown classes based on Pfam domain content. Their method identified several hundred RiPP clusters in a sample of 1,154 genomes, but was not capable of predicting the structures of their corresponding products. Moreover, manual annotation was required to identify the family of RiPPs that each cluster belonged to. BAGEL3, is a web-server for automated identification of genes encoding bacteriocins and (non)-bacteriocidal post-translationally modified peptides using updated bacteriocin and context protein databases where the input is single or multiple FASTA formatted files (on the internet at: bagel.molgenrug.nl/index.php/bagel3), is capable of identifying 12 families of RiPPs and therefore represents the most comprehensive platform for RiPP genome mining currently available. However, this platform cannot predict precursor cleavage or generate predicted structures. In contrast, PRISM uses a library of 154 hidden Markov models to identify 21 families of RiPPs, an ensemble of hidden Markov models and heuristics to identify putative precursors, a set of 54 motifs to predict precursor cleavage, and a library of 94 virtual tailoring reactions to generate highly accurate predicted structures, making it a uniquely comprehensive resource for RiPP genome mining. The scale of the genome mining effort presented here, with the identification of over 30,000 clusters in over 60,000 prokaryotic genomes, as well as the ability of PRISM to dereplicate clusters which produce the same natural product both attest to its advantages as a platform for RiPP discovery.

The approach presented here relies fundamentally on homology to known clusters and experimentally elucidated biosynthetic transformations to identify RiPP clusters from sequence data and predict the structures of their products. Although this approach enables a comprehensive characterization of the biosynthetic and structural landscape of genetically encoded RiPPs with known chemotypes, it has at least two significant limitations with respect to RiPP discovery. In particular, our approach cannot identify novel families of RiPPs, and it cannot predict the presence or mechanisms of novel enzymatic tailoring reactions. Therefore, it is nearly certain that this analysis will have failed to identify RiPP clusters corresponding to novel chemotypes, and likewise will have failed to predict the action of enzymatic tailoring reactions with little or no homology to known enzymes in RiPP biosynthesis. However, these failings are not unique to the platform described here: to date, no computational strategy is capable of predicting the action of novel tailoring enzymes in natural product biosynthesis except by homology to known enzymes, and while some machine learning strategies are capable of identifying clusters from previously unknown families, they are not capable of predicting the structures of the genetically encoded products. Moreover, we emphasize that although our validation demonstrated PRISM is capable of highly accurate structure predictions, perfect accuracy is not necessary to dereplicate clusters which produce the same product, since PRISM will always generate the same predicted structures from the same set of identified biosynthetic information.

Figure 13:
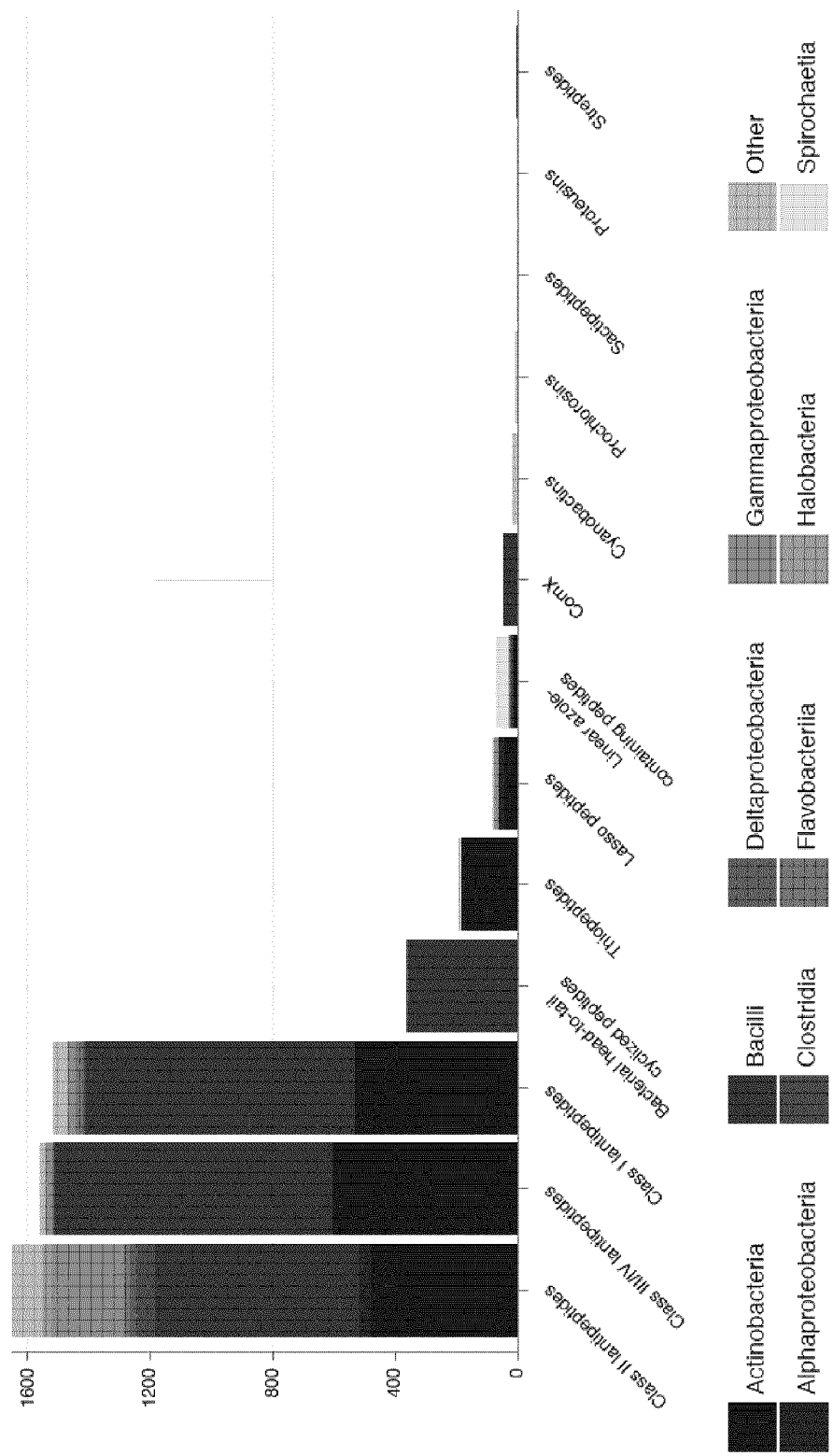
FIG. 13 is a plot of 5,505 clusters by RiPP family and producing organism taxonomy.

Although we identified 30,261 RiPP clusters in a sample of 65,421 prokaryotic genomes, PRISM generated predicted structures for only 24,756 (81.8%). This figure is considerably lower than the fraction of clusters for which at least one predicted structure was generated during validation on known products (99.3%). We plotted the remaining 5,505 clusters by RiPP family and producing organism taxonomy in FIG. 13. Class I, II, and III/IV lantipeptides cumulatively accounted for over 86% of clusters without a structure predicted. This can likely be attributed to the tremendous diversity of lantipeptide precursors, which likely precluded precursor identification or cleavage for lantipeptides with little homology to known precursors. The only other families of RiPPs with more than 100 clusters detected but without predicted structures were bacterial head-to-tail cyclized peptides and thiopeptides; these failures can presumably be attributed to the same factors as lantipeptides, as well as the absence of a heuristic for bacterial head-to-tail cyclized peptide precursor identification. Manual inspection of thiopeptide clusters without predicted structures revealed a large number (>50) from the frequently sequenced genus Salinispora, where a large transposon insertion had occurred between the precursor and biosynthetic genes, placing it outside of the cluster size range considered by PRISM: it is possible that transposon insertion produced similarly incomplete results for other clusters.

Ribosomally synthesized and post-translationally modified natural products have great therapeutic promise, but their biosynthetic and chemical diversity has precluded the development of bio- and cheminformatic strategies to predict their structures from genome sequence data. In this work, we have introduced the first comprehensive platform for identifying RiPP gene clusters and predicting their chemical structures with a high degree of accuracy. We have leveraged this platform to conduct a global analysis of genetically encoded RiPPs, which revealed that though these molecules are nearly universally distributed throughout prokaryotic phyla, the vast majority of remain unknown. Finally, by creating highly accurate structure predictions, PRISM can facilitate the targeted detection of new molecules from LC-MS data based on genome sequence data, leading in this work to the discovery of a new natural product from a rare family of RiPPs. Our results highlight the advantages of this uniquely comprehensive platform for the genome-guided discovery of novel RiPPs.

Methods Used in Accordance with Example A

General Computational Methods

Hidden Markov models were constructed by manual compilation of experimentally annotated sequences, which were supplemented with homologs identified by querying the IMG and NCBI BLAST databases. Sequences were aligned with MUSCLE (Multiple Sequence Comparison by Log-Expectation) (version 3.8.31) and trimmed using trimAI (version 1.2rev59) to remove gaps. Hidden Markov models were compiled from the trimmed alignments using hmmbuild (version 3.1b1) and bitscore cutoffs were determined by manual analysis of the results of searches of the UniProtKB and UniProt reference proteome databases. Motif discovery was performed using the MEME web server, allowing any number of motif occurrences with a minimum motif length of 6 amino acids and a maximum length of 25 amino acids. The Chemistry Development Kit (version 1.5.10) implementation of the ECFP6 chemical fingerprint was used to calculate Tanimoto coefficients.

Development of an Algorithm for Genome-Guided Chemical Structure Prediction of RiPPs We developed a novel algorithm to identify biosynthetic gene clusters and predict chemical structures for 21 families of RiPPs by extending the open-source PRISM framework. PRISM is a Java 8 web application built for the Apache Tomcat 7 web server, which implements BLAST (version 2.2.25+), HMMER (version 3.1b1), BioJava (version 3.0.7), BioPerl (version 1.006924), RDKit (version 2014.03.1), the Chemistry Development Kit (version 1.4.19), Prodigal (version 2.6.2) and FIMO (version 4.11.0). PRISM queries a user-input sequence with a library of several hundred hidden Markov models and curated BLAST databases in order to identify nonribosomal peptide, type I and II polyketide, deoxysugar, and resistance domains. The results of this search are used to identify natural product biosynthetic gene clusters. Linear scaffolds are generated and elaborated in a combinatorial manner based on predicted tailoring reactions, deoxysugar moieties, and cyclizations to generate a combinatorial library of predicted structures.

We extended PRISM by developing 53 motifs, 150 new hidden Markov models, and 94 new virtual tailoring reactions for specific to RiPP biosynthesis, and developed rules for the identification of biosynthetic gene clusters for 21 families of RiPPs. Precursor peptides are identified with a combination of hidden Markov models and heuristic strategies, and are cleaved at their N-terminus and/or C-terminus based on conserved motifs. Tailoring reaction domains are identified, and all potential reaction sites are determined. Virtual reactions are then executed combinatorially in order to produce a library of hypothetical structures corresponding to the identified biosynthetic gene cluster. A detailed description of precursor peptide cleavage and tailoring reaction execution is presented in the Supplementary Methods. We note that although tailoring reactions are described in the Supplementary Methods according to biosynthetic family, each tailoring reaction can occur within any class of RiPPs: thus, for example, the identification of a putative domain with homology to cyanobactin prenyltransferases within a lantipeptide cluster would result in the generation of O- or N-prenylated hypothetical lantipeptide structures.

All rules for RiPP cluster detection are presented in FIG. 45.

Validation of Predictive Accuracy

PRISM was run on 136 known RiPP clusters with the following settings: tailoring, deoxy sugar, and RiPP domain HMM searches enabled; both Prodigal and all potential coding sequences used to identify open reading frames; and cluster scaffold library limit of 100. Predicted and true structures were compared with the Tanimoto coefficient.

Global Analysis of Genetically Encoded RiPP Chemical Space 65,426 prokaryotic genomes were retrieved from NCBI Genome in March 2016. PRISM was run on each genome with the following settings: tailoring, deoxy sugar, and RiPP domain HMM searches enabled; Prodigal used to identify open reading frames; cluster window of 5,000 base pairs; and a cluster scaffold library limit of 100. 65,421 of 65,426 genomes were successfully run through PRISM. Taxonomic information for each genome was retrieved with the ETE module in Python. JSON output from PRISM was parsed to retrieve all predicted structures for each cluster and the RiPP family or families of the cluster. All predicted structures from each of the 24,756 clusters for which predicted structures were generated were compared to one another to generate Tanimoto coefficient matrices ranging in size from 1×1 to 100×100. The median value of all Tanimoto coefficients within the matrix was assigned to the cluster-cluster comparison unless the matrix contained one or more instances of 1.0, in which case the clusters were understood to produce the same product and a value of 1.0 was assigned to the cluster-cluster comparison.

Plotting RiPP Chemical Space

A Tanimoto coefficient similarity matrix was generated for a comprehensive collection of 509 known ribosomal natural products, including molecules from 18 distinct families. ECFP6 chemical fingerprints were used to calculate Tanimoto coefficients. Molecules with the highest median within-family Tanimoto coefficients were taken as representative structures, and the resulting 18-member Tanimoto similarity matrix was plotting with multidimensional scaling (MDS) using XLSTAT 2016. MDS was performed with default settings, presenting final results in two dimensions using an absolute model, measuring correspondence between the matrix input and final distances via Kruskal stress formula 1. Minimization was completed after maximum convergence (0.00001) was reached. Points for representative structures in the resulting plot were enlarged such that their area corresponded to the number of members of their associated RiPP class, with colour corresponding to the median within-family Tanimoto coefficient. Lantipeptides of classes I, II, III, and IV were here classed as a single family, as this plot includes all known compounds, including structures whose biosynthetic origins are undetermined. To plot genetically encoded RiPP chemical space, the number of unique products was used to determine the size of each node, and the average median within-family Tanimoto coefficient was used to colour nodes according to within-family chemical diversity.

General Experimental Procedures Used in Accordance with Example A 1D ($^1$H and $^{13}$C) and 2D ($^1$H-$^{13}$C HMBC, HSQC, $^1$H-$^1$H NOESY, TOCSY, and COSY) NMR spectra for aurantizolicin was recorded on a Bruker AVIII 700 MHz NMR spectrometer in $d_6$-DMSO (Sigma-Aldrich). High-resolution LCMS spectra were collected on a SciEX 5600+ TripleTOF mass spectrometer (ABSciEX) with an electrospray ionization source (ESI) and using CID with helium for fragmentation, coupled with an Agilent 1100 series HPLC system using a Ascentis Express C8 column (150 mm×2.1 mm, 2.7 mm; Sigma-Aldrich) for analytical separations, running acetonitrile with 0.1% formic acid and $ddH_2O$ with 0.1% formic acid as the mobile phase. Preparative HPLC was performed using a Dionex UltiMate 3000 HPLC system, using a Luna C8 column (250 mm×10 mm, Phenomenex), running acetonitrile with 0.1% formic acid and $ddH_2O$ with 0.1% formic acid as the mobile phase.

Microbial Strains and Culturing

*Streptomyces aurantiacus* JA 4570 was obtained from the Hans-Knöll-Institute (IMET 43917). It was maintained on Bennett's agar at 28° C. Bennett's agar contains 15 g/L agar, 1 g/L beef extract, 1 g/L yeast extract, 2 g/L NZ-amine, and 10 g/L glucose, with pH adjusted to 7.3. KE media contains 1 g/L glucose, 10 g/L potato dextrin, 5 g/L yeast extract, 5 g/L NZ-amine, 3 g/L beef extract, 0.5 g/L calcium carbonate, and 0.05 g/L magnesium sulfate heptahydrate. After autoclaving, 2 mL/L sterile phosphate buffer (91 g/L potassium phosphate monobasic and 95 g/L potassium phosphate dibasic, pH 7) was added. Aurantizolicin was initially detected in a media containing 20 g/L sodium chloride, 10 g/L soluble starch, 0.3 g/L casein, 2 g/L potassium nitrate, 2 g/L potassium phosphate dibasic, 0.05 g/L magnesium sulfate heptahydrate, 0.02 g/L calcium carbonate, and 0.01 g/L iron (II) sulfate heptahydrate. Aurantizolicin production media contains 20 g/L sodium chloride, 10 g/L soluble starch, 3 g/L casein, 2 g/L potassium nitrate, 2 g/L potassium phosphate dibasic, 0.05 g/L magnesium sulfate heptahydrate, 0.02 g/L calcium carbonate, 0.01 g/L iron (II) sulfate heptahydrate, and 30 g/L washed HP-20 resin (Diaion).

Production and Isolation of Aurantizolicin

*Streptomyces aurantiacus* was grown on Bennett's agar for two weeks at 28° C. Colonies were added to 250 mL Erlenmeyer flasks containing 50 mL of KE media and grown for 48 hours at 28° C. and 225 rpm. From these, 10 mL of culture was added to a 2.8 L Fernbach flask containing 1 L of aurantizolicin production media, which was incubated at 28° C. and 225 rpm for 72 hours. Mycelial mass and resins were collected via Buchner funnel vacuum filtration using non-gauze milk filters (KenAG). The resultant cell pellet and resin cake was extracted multiple times with excess acetone that was evaporated to dryness using a rotary evaporator. The dried extract was resuspended and partitioned in 1:1 butanol-water, collecting the butanol phase and evaporating it to dryness. Dried extract was resuspended in methanol and loaded on a large open column containing LH20 resin (Sephadex) with methanol as the mobile phase. Fractions containing aurantizolicin were pooled, dried down, and resuspended in a small volume of DMSO. Aurantizolicin was purified by semi-preparative scale HPLC, using a Luna C8 column (250×10 mm) with ddH$_2$O and acetonitrile containing 0.1% formic acid as the mobile phase, pumping at 8 mL/min. Acetonitrile was 5% for the first 3 min, ramping to 50% by 10 min, then to 80% by 23 min, then proceeding to 100% at 24 min. Aurantizolicin eluted at 20.2 min. 60 L of optimized production culture provided <1 mg of aurantizolicin. HPLC fractions containing aurantizolicin were dried down and resuspended in d$_6$-DMSO for NMR.

Incorporation of d$_8$-Phenylalanine into Aurantizolicin

Streptomyces aurantiacus was grown on Bennett's agar for two weeks at 28° C. Colonies were added to 250 mL Erlenmeyer flasks containing 50 mL of KE media and grown for 48 hours at 28° C. and 225 rpm. From these, 1 mL of culture was added to a 250 mL Erlenmeyer flask containing 50 L of aurantizolicin production media without HP20 resin, which was incubated at 28° C. and 225 rpm for 72 hours. After 24 hours, d$_8$-phenylalanine was added via sterile syringe filtration to a final concentration of 4 mM. Cultures were extracted and analyzed by LCMS.

High Resolution Mass Spectrometry of Aurantizolicin

| Compound | Formula | Calc. | Obs. | Δppm |
|---|---|---|---|---|
| Aurantizolicin | C$_{35}$H$_{35}$N$_8$O$_6$S$_2$ [M + H] | 727.21155 | 727.21119 | 0.495 |

Structure Confirmation of Aurantizolicin

The structure of aurantizolicin that was predicted by PRISM and identified in LCMS chromatograms was highly similar to the known structures urukthapelstatin and YM-216391, whose NMR assignments had been made previously in d$_6$-DMSO. Chemical shifts of aurantizolicin detected from the NMR sample were extremely similar to reported shifts for urukthapelstatin and YM-216391.

$^1$H proton and $^1$H-$^{13}$C HSQC experiments confirmed the presence of four well conserved azole protons that were nearly identical to those from urukthapelstatin, which possesses the same azole ring system (avg. $^1$H Δppm of 0.01, avg. $^{13}$C Δppm of 0.47). $^1$H-$^{13}$C HMBC experiments from these protons revealed correlations to aromatic carbons that again closely matched those from the identical urukthapelstatin ring system, as well as from the glycine carbonyl-derived carbon of the first oxazole of YM-216391 (avg. $^{13}$C Δppm of 0.09).

Chemical shifts for the phenyloxazole which had been indicated in the structure prediction and isotope incorporation data were most highly similar to those observed in urukthapelstatin. $^1$H proton signal integration and coupling constants, $^1$H-$^1$H COSY and TOCSY experiments, and $^1$H-$^{13}$C HSQC experiments confirmed the presence of the aromatic phenyl ring, with signals nearly identical to those reported for urukthapelstatin (avg. $^1$H Δppm of 0.01, avg. $^{13}$C Δppm of 0.19). $^1$H-$^{13}$C HMBC experiments confirmed HSQC correlations and provided correlations to aromatic carbon 1 and to the β-carbon found in the oxazole.

$^1$H-$^1$H 2D-TOCSY, COSY, and NOESY experiments revealed three systems related to the predicted amino acids. Glycine was identified via an NH doublet signal at 8.80 ppm, which was found to possess correlations to a pair of CH$_2$ protons at 5.02 ppm and 4.17 ppm. These protons shared a carbon signal at 34.85 ppm and possessed a $^1$H-$^{13}$C HMBC correlation to the adjacent aromatic oxazole carbon. Chemical shifts for this glycine were nearly identical to those reported in the YM-216391 structure (avg. $^1$H Δppm of 0.06, $^{13}$C Δppm of 0.35). The isoleucine adjacent to the phenyloxazole was identified via an NH doublet signal at 8.13 ppm which possessed a correlation to a doublet-of-doublets at 4.82 ppm. This putative alpha-proton signal had correlations to another proton at 1.98 ppm, which was then connected to a fourth proton at 0.91 ppm. $^1$H-$^1$H 1D TOCSY experiments irradiating either the distinct amide NH at 8.13 ppm or the alpha proton at 4.82 ppm were used to reveal the entire isoleucine spin system, including CH$_2$ protons at 1.62 ppm and 1.06 ppm, as well as the terminal CH$_3$ at 0.87 ppm. $^1$H-$^{13}$C HSQC experiments were used to reveal associated carbon chemical shifts, although CH$_3$ signals could not be definitively assigned due to extensive overlap. Chemical shifts for this isoleucine were nearly identical to those reported in the YM-216391 structure (avg. $^1$H Δppm of 0.05, $^{13}$C Δppm of 0.46). The unique aurantizolicin isoleucine (replacing the valine observed in YM-216391 and alanine observed in urukthapelstatin) was identified via an NH doublet signal at 8.60 ppm that possessed a correlation to a triplet at 4.39 ppm. This alpha proton possessed a correlation to a CH proton at 1.88 ppm, which was then connected to a CH$_3$ at 0.90 ppm. A $^1$H-$^1$H NOESY experiment revealed CH$_2$ protons at 1.51 ppm and 1.25 ppm, and confirmed the order of the observed amino acids. $^1$A $^1$H-$^1$H 1D TOCSY experiment irradiating the distinct amide NH at 8.60 ppm was used to reveal the entire isoleucine spin system, including the terminal CH$_3$ at 0.87 ppm. $^1$H-$^{13}$C HSQC experiments were used to reveal associated carbon chemical shifts, although carbon signals corresponding to the CH$_3$ groups could not be definitively assigned due to extensive overlap.

Supplementary Methods Used in Accordance with Example A

Autoinducing peptides (AIPs) are quorum-sensing peptides produced by firmicutes, and are distinguished from linear regulatory peptides by the presence of a cyclic ester or thioester. Their biosynthesis is encoded in the accessory gene regulator (agr) locus. Conserved features of this locus include the AgrD and AgrB genes, which encode the precursor peptide and the enzyme responsible for leader peptide cleavage and macrocyclization, respectively. Putative AIP clusters are identified in PRISM if they contain homologs of both AgrD and AgrB. Analysis of AgrD sequences revealed a single conserved motif with C-terminal leader peptide cleavage four residues from the end of the motif. However, the relationship between the beginning of the motif and N-terminal cleavage was less clear, with cleavage known to occur at a distance of three, four, or five amino acids before the start of the motif. Consequently, all three possibilities are considered within PRISM. AgrB is assumed to catalyze ester or thioester formation between the C terminus of the cleaved leader peptide and the side chain of a conserved serine or cysteine residues four amino acids from the C terminus.

Bacterial head-to-tail cyclized peptides are relatively large bacterial peptides which contain a peptide bond between the C and N termini. They are distinguished from other cyclic RiPPs both by their size and by the mechanism of macrocyclization. A conserved DUF95-family enzyme is present in all known clusters, and may be associated with transport or macrolactam formation. Putative clusters are identified if they contain a precursor peptide and a DUF95-family enzyme. Three conserved motifs were identified within a dataset of 21 known and putative precursor peptides. Cleavage generally occurred five amino acids before the start of the first motif, or three amino acids before the start of the second motif (six when the third motif was also present). The DUF95 enzyme is assumed to catalyze macrolactam formation between the C and N termini.

The bottromycin family of natural products includes several closely related compounds with unique structural features, including a decarboxylated C-terminal thiazole, a macrocyclic amidine, and multiple C-methylated amino acids. The precursor peptide is notable for conserved C-terminal leader cleavage. Putative clusters are identified if they contain the bottromycin precursor and a homolog of BotC, an enzyme with weak homology to the YcaO family of proteins which has been speculated to catalyze macrocyclodehydration. A conserved motif was identified at the C-terminal 'follower' sequence, analogous to the N-terminal leader sequence in lantipeptides. Cleavage occurs a single amino acid before the start of this motif in all known bottromycins. Seven virtual tailoring reactions were developed for bottromycin-family RiPPs. BotC is assumed to catalyze macrocyclodehydration and amidine formation between the N-terminal residue and the 5th residue, while the related YcaO family protein BotCD is assumed to catalyze cyclodehydration of the C-terminal cysteine residue to form a thiazole. Although no known bottromycin precursor sequences contain serine or threonine residues, these are also considered potential substrates of BotCD in the event that oxazole or 5-methyloxazole-containing bottromycins are discovered in the future. Homologs of the bottromycin O-methyltransferase BotOMT are assumed to catalyze aspartate side chain O-methylation, while removal of the N-terminal methionine is assumed to be catalyzed by the homologs of the leucyl aminopeptidase BotP. Finally, BotRMT3 catalyzes proline β-C-methylation, BotRMT1 catalyzes phenylalanine β-C-methylation, and BotRMT2 catalyzes β-C-methylation of any subset of valine residues.

ComX is a quorum-sensing peptide produced by bacilli, which is characterized by a unique isoprenylation and cyclization reaction at a conserved tryptophan residue. Putative clusters are identified if they contain homologs of both the ComX precursor peptide and the isoprenyltransferase ComQ. Cleavage is assumed to occur at 11, 9, or 6 residues after the end of the conserved motif; the largest which produces a peptide with at least five amino acids, although the limited number of annotated precursor peptide sequences and variable length of the precursor peptides limits the accuracy of cleavage prediction. ComQ is assumed to catalyze formation of the unique geranyl-derived tricyclic ring structure of ComX at any tryptophan.

Cyanobactins are a large family of RiPPs produced by cyanobacteria, with common modifications including N-to-C macrocyclization, cyclodehydration to form thiazolines and oxazolines, heterocycle oxidation to form thiazoles and oxazoles, and prenylation. Macrocyclization was until recently thought to be a defining feature of this family of RiPPs, but linear cyanobactins have also been reported. Biosynthesis involves both N- and C-terminal cleavage of the PatE precursor peptide; several precursor peptides encode multiple core peptides, which are each flanked by conserved N- and C-terminal recognition sequences. The PatA protease catalyzes N-terminal recognition sequence cleavage, while the PatG protease catalyzes C-terminal recognition sequence cleavage and macrocyclization. Several PatG homologs also contain an oxidative domain responsible for azoline oxidation. Other conserved biosynthetic machinery includes the prenyltransferase PatF, which may or may not be active, the cyclodehydratase PatD, and two proteins of unknown function (PatB and PatC).

Putative cyanobactin clusters are identified within PRISM if they contain a cyanobactin precursor and homologs of both the PatA and PatG proteases; the PatG protease may or may not have an oxidative domain. A single propeptide is assumed to be produced from the cyanobactin precursor. Two general patterns of precursor cleavage were observed. One large group of cyanobactins had a single occurrence of a distinct C-terminal motif, with one or two N-terminal motifs. Cleavage occurred at the end of the second N-terminal motif, if present, or twelve residues after the end of the first, with C-terminal cleavage seven residues before the start of the C-terminal motif. The second large group of cyanobactins also had two N-terminal motifs and one of two repeating motifs. N-terminal cleavage occurred four residues after the second N-terminal motif, with C-terminal cleavage four residues before the end of the repeating motif.

Four tailoring reactions were developed for cyanobactin post-translational modifications, including macrocyclization, cyclodehydration, azoline oxidation, and prenylation. PatD homologs are assumed to catalyze cyclodehydration of any subset of serine, threonine, and cysteine residues without bis-azoline formation. Distinct hidden Markov models were constructed for PatG sequences with and without oxidation domains. PatG homologs are assumed to catalyze N-to-C macrocyclization, and those with an oxidative domain are additionally assumed to catalyze azoline oxidation. Finally, PatF domains are assumed to each catalyze prenylation of either one or two residues, with possible sites of prenylation including the N-terminus, side chain hydroxyls of threonines, serines, and tyrosines, and arginine guanidino groups. A hidden Markov model was also constructed with inactive PatF sequences to predict the presence of inactive prenylating domains. A hidden Markov model was also constructed specific to the unique aeruginosamide putative bifunctional methyltransferase/prenyltransferase AgeF1, which is assumed to catalyze C-terminal methylation and N-terminal prenylation.

Glycocins are a small family of RiPPs with only two characterized members (sublancin 168 and glycocin F). Their biosynthesis is characterized by the formation of two alpha helices by the introduction of two disulfide bonds, with O- or S-glycosylation of a serine or cysteine residue. Putative clusters are detected if they contain both a glycocin precursor and a glycosyltransferase. The paucity of known glycocin sequences complicates accurate cleavage prediction. However, within PRISM, cleavage is assumed to occur either zero or two residues after the lone identified motif. Although the sublancin 168 cluster contains two thiol-disulfide oxidoreductases, the mechanism of disulfide bond formation is not clear, and therefore is associated with the precursor itself within PRISM. Only combinations of disulfide bonds which result in the characteristic 'hairpin' secondary structure of glycocins are considered. Homologs of the SunS enzyme are assumed to catalyze glycosylation of cysteine and serine residues. If the tail is glycosylated, as in glycocin F, the hairpin is also assumed to be glycosylated.

Lantipeptides are a large class of RiPPs characterized by the presence of the amino acids lanthionine and methyllanthionine. They are divided into four classes based on the enzymatic mechanism by which these groups are installed.

In class I lantipeptides, a dehydratase catalyzes the dehydration of serine and threonine residues, and a cyclase subsequently catalyzes cyclization of cysteine residues on the dehydro amino acids. Putative class I lantipeptides are identified by the presence of a dehydratase (LanB) and cyclase (LanC). LanB is assumed to catalyze dehydration of any subset of serine and threonine residues, with a minimum size of two when there are two or more serine and threonine residues. N-terminal dehydroalanine and dehydrobutyric acid residues are tautomerized to pyruvate and 2-oxobutyrate, respectively. LanC is assumed to catalyze cyclization between all possible permutations of cysteines and dehydrated serine or threonine residues.

Hidden Markov models were also developed for several tailoring enzymes specific to individual families of class I lantipeptides. LanD enzymes catalyze oxidative decarboxylation of C-terminal residues to form aminovinylcysteine, and are assumed to react at any combination of a C-terminal cysteine and a dehydroalanine residue. LanJ enzymes, such as that found in the biosynthetic gene cluster of the class I lantipeptide lacticin 3147, catalyze the reduction of dehydroalanine to D-alanine, and are assumed to react at any dehydroalanine residue. Homologs of the epilancin short-chain dehydrogenase ElxO are assumed to reduce an N-terminal pyruvate residue to lactate. Homologs of the microbisporicin halogenase MibH are assumed to catalyze C-5 chlorination of a tryptophan residue, while homologs of the cytochrome P450 MibO are assumed to catalyze 3,4-dihydroxylation of a proline residue. Homologs of the paenibacillin acetyltransferase PaeN are assumed to catalyze N-terminal acetylation.

In class II lantipeptides, a fused cyclase/dehydratase (LanM) catalyzes both steps of lanthionine formation. Putative class II lantipeptide clusters are identified within PRISM based on the presence of a LanM enzyme. Since class II lantipeptides may also contain uncyclized dehydroalanine or dehydrobutyric acid residues, LanM is assumed within PRISM to catalyze both cyclization between all possible permutations of cysteines and serine or threonine residues, and dehydration of any subset of remaining serine or threonine residues. Hidden Markov models were also constructed for tailoring enzymes specific to individual families of class II lantipeptides, including homologs of the cinnamycin biosynthesis proteins cinorf7, which is assumed to catalyze cross-linking of a lysine residue and a dehydroalanine residue, and CinX, an α-ketoglutarate/iron(II)-dependent hydroxylase assumed to catalyze β-hydroxylation of an aspartate residue. A hidden Markov model was also constructed for homologs of the actagardine luciferase-like monooxygenase GarO, which is assumed to catalyze oxidation of a lanthionine to form a sulfoxide group.

In class III and IV lantipeptides, a peptide with lyase, kinase, and cyclase domains catalyzes a range of reactions, including dehydration of serine and threonine residues, lanthionine and methyl-lanthionine formation, as well as the formation of the modified amino acid labionin. Putative class III/IV lantipeptide clusters are identified within PRISM based on the presence of a LanKC/LanL enzyme. Within PRISM, labionin formation occurs between any ordered triad of two serine residues and a cysteine residue such that the size of the first ring is three amino acids, and the size of the second ring is between three and six amino acids. All potential labionins are formed, where the number of possible labionins is defined as the smaller of the number of cysteine residues or half the number of serine residues. For each permutation of labionins, all combinations of dehydroalanines, dehydrobutyrates, and lanthionines are additionally considered.

Prochlorosins represent a distinct group of class II lantipeptides, whose biosynthesis is characterized by the action of a single, highly promiscuous LanM-type enzyme on a diverse series of precursor peptides with a conserved leader peptide, but little core peptide sequence identity. A distinct model was constructed for prochlorosin precursors, generically termed ProcA. Because the genomes of many prochlorosin producers contain only a single LanM-type enzyme, but encode precursor peptides at multiple different loci, the presence of a ProcA precursor alone defines a prochlorosin cluster. The LanM annotator and reaction classes from class II lantipeptides are reused for prochlorosins, but with the assumption that this reaction occurs regardless of the presence of a LanM-type enzyme within the same cluster.

With the exception of prochlorosins, precursor identification within PRISM is independent of lantipeptide class. Thirteen hidden Markov models were developed for lantipeptide precursors. Three TIGRFAM models are also included to detect unusual precursors related to the enzymes nitrile hydratase and Nif11, for either lantipeptides or linear azol(in)e-containing peptides (see below). In lantipeptide clusters which still lack a precursor, a heuristic strategy is applied to identify putative precursors: open reading frames between 30 and 80 amino acids containing two cysteines are considered as potential lantipeptide precursors.

Highly conserved motifs were identified for three large clades of lantipeptides. The common GG/GA motif is used preferentially to cleave the precursor peptide, with cleavage at the end of the motif, even if other motifs are present. Two conserved motifs were also identified within two other large clades of lantipeptides, with cleavage seven residues after the start of the first motif, and four residues after the end of the second. A smaller clade of two-component lantipeptides, including cytolysin, cerecidin, and lichenicidin, also had a conserved motif with cleavage four residues after the end. However, more specific motifs were also identified for specific families of lantipeptides, including SapB/AmfS-type lantipeptides (cleavage four residues before the end of the motif), pep5/epilancin-type lantipeptides (cleavage nine residues after the end of the motif), actagardine/michiganin-type lantipeptides (cleavage eight residues after the start of the motif), type IV lantipeptides (cleavage four residues after the end of the motif), labyrinthopeptins (cleavage nine residues before the end of the motif), pinensins (cleavage two residues after the end of the motif), SmbA/BhtA2-type precursors (seven residues before the end of the motif) and SmbB/BhtA1-type precursors (18 residues after the end of the motif), and staphylococcin 055-type lantipeptides (three residues before the end of the motif).

Lasso peptides are a family of RiPPs characterized by their unique secondary structure, with an isopeptide bond between the N-terminus and a side chain carboxylic acid forming a loop through which the tail of the peptide is threaded. Identification of putative lasso peptide clusters requires the presence of two conserved lasso peptide biosynthesis proteins with homology to transglutaminases and asparagine synthases. Putative lasso peptide precursors are identified with a hidden Markov model or, in lasso peptide clusters where no precursor can be identified, by adapting a previously published heuristic for lasso peptide precursor discovery. We relaxed this heuristic to consider all open reading frames less than 80 amino acids in length, with a Tx(G/C)x6-8(D/E) motif at a distance of 0-50 amino acids from the start and more than 5 amino acids from the end. For lasso peptide precursors identified with an HMM, cleavage is predicted to occur three residues before the end of the leader peptide motif. However, for heuristically identified precursors, cleavage is predicted to occur two residues after the start of the motif. Asparagine synthase homologs are assumed to catalyze formation of the lasso fold by condensing the N-terminal amine with the side chain of a glutamate or aspartate residue between positions 7 and 10. Finally, when one or more disulfide bonds are possible, all possible permutations of one, two, or three disulfide bonds are considered.

Linaridins are a small, linear family of natural products characterized by the presence of dehydrated amino acids with aminovinylcysteine moieties installed by a biosynthetic route which diverges from that of lantipeptides. Putative linaridin clusters require a precursor peptide and homologs of the unique CypH and CypL proteins. Separate hidden Markov models were constructed for cypemycin and grisemycin-type precursors and for legonaridin-type precursors, which represent a distinct subfamily of linaridins. Distinct motifs were likewise identified for cypemycin and grisemycin-type precursors and for legonaridin-type precursors, with leader cleavage occurring three residues before the end of each. The cypemycin genes CypL and CypH encode proteins with no functional homologs required for cypemycin production, which are proposed to catalyze dehydration of threonine residues. Although no dehydroalanine-containing legonaridins are known, these proteins are also considered within PRISM to potentially catalyze dehydration of serine residues, in the event that dehydroalanine-containing legonaridins are isolated in the future. The CypH and CypL enzymes are arbitrarily assigned to threonine and serine dehydration respectively within PRISM, although these enzymes are not found separately[19]. A separate hidden Markov model was developed for the distinct legonaridin protein LegH. Homologs of the lantipeptide aminovinylcysteine biosynthesis flavoprotein in linaridin clusters are assumed to react at a C-terminal cysteine residue and any other cysteine. Homologs of the cypemycin methyltransferase CypM are assumed to catalyze N,N-dimethylation of the N-terminal residue.

Linear azol(in)e-containing peptides (LAPs) are a family of RiPPs defined by the presence of thiazole and (methyl)oxazole heterocycles in an otherwise linear core peptide. Identification of putative LAP clusters requires the presence of either the dehydrogenase McbB and one of the potentially fused cyclodehydratases McbC or McbD, or the goadsporin enzyme GodG. Separate hidden Markov models were developed for goadporin, microchip B17, streptolysin, and plantazolicin-type precursor sequences. When no precursor is identified, a heuristic strategy is adapted for precursor identification. Open reading frames between 30-70 amino acids which contain a sequence of 7 amino acids of which all 7 are serine, threonine, or cysteine, or a sequence of 8 amino acids of which at least 7 are serine, threonine, or cysteine, are considered potential LAP precursors. Due to the low homology of known LAP precursors, we identified four separate leader peptide motifs for each, with predicted cleavage occurring three residues after the end of the goadsporin-type motif, five residues after the end of the microcin B17-type motif, one residue after the end of the streptolysin-type motif, and five residues before the end of the plantazolicin-type motif. Dehydratases (McbB) and cyclodehydratases (McbC and McbD) are assumed to react at identical substrates to analogous enzymes in lantipeptides, with the exception that a maximum of four serine or threonine residues are left uncyclized in LAPs. All cysteine residues are assumed to undergo heterocyclization. In homologs of the goadsporin cluster, both GodF and GodG are required for dehydroalanine formation, while GodD and GodF are arbitrarily associated with cyclodehydration and oxidation, respectively, in azole formation. Finally, homologs of the GodH acetyltransferase catalyze N-terminal acetylation, while homologs of the plantazolicin methyltransferase PznL catalyze N,N-dimethylation of the N-terminus.

Microviridins are a family of N-acetylated cyanobacterial peptides containing intramolecular amide and ester bonds, which are installed by the ATP-grasp enzymes MdnB and MdnC, respectively. Putative microviridin clusters are identified if they contain both a precursor peptide and at least one ATP-grasp enzyme. A conserved motif was identified within the core peptide, with N-terminal cleavage predicted to occur three residues before its start. If the C-terminus of the peptide is more than one residue from the end of the open reading frame, C-terminal cleavage is also predicted to occur. The ATP-grasp enzyme MdnB is assumed to catalyze amide bond formation between lysine residues and aspartate or glutamate side-chain carboxylic acids, while MdnC is assumed to catalyze ester bond formation between any subset of two serine and threonine residues and the side chain carboxylic acids of any subset of two aspartate and glutamate residues. Finally, the acetyltransferase MdnD is assumed to catalyze acetylation of the N-terminus.

Polytheonamides are the lone member of the proteusin family of RiPPs, a family of large D-amino acid-containing peptides which form unimolecular membrane channels with femtomolar affinity. Their biosynthesis is notable for the installation of 48 post-translational modifications by six enzymes. Putative proteusin clusters are identified by the presence of a precursor and the PoyD epimerase. A conserved motif was identified within the leader peptide of putative proteusins, with cleavage predicted to occur immediately after this motif. Polytheonamide biosynthesis involves a set of iterative enzymes with a high degree of substrate specificity. However, the absence of other members of the proteusin class limits the specificity with which the activities of homologs of these enzymes can be predicted within PRISM. Thus, for instance, the SAM-dependent methyltransferase PoyE is assumed to catalyze side chain N-methylation of 6 to 9 asparagine residues, while either of the closely related radical SAM proteins PoyB and PoyC is assumed to catalyze β-methylation of 10 to 15 isoleucine, valine, threonine, glutamine, or methionine carbons. The Fe(II)/α-ketoglutarate oxidoreductase PoyI is assumed to catalyze β-hydroxylation of 3 to 5 asparagine and valine residues. PoyF, which has homology to the dehydratase domain of LanM lantibiotic synthetases, is assumed to catalyze dehydration of the polytheonamide N-terminal threonine, with subsequent leader peptide cleavage causing tautomerization and α-ketone formation. It is assumed to react at a N-terminal serine or threonine residue. The activity of the proteusin epimerase PoyD is not predicted because PRISM does not generate chiral structure predictions.

Sactipeptides are a family of peptides defined by the presence of one or more bonds between a cysteine sulfur and the α-carbon of another residue. Identification of putative sactipeptide clusters requires the presence of a sactipeptide precursor and a homolog of the subtilosin radical SAM enzyme AlbA. We identified five conserved motifs. Precursors with an SkfA-type motif in the leader peptide have predicted cleavage one residue before the end of the motif. Precursors with an SboA-type motif spanning the leader and core peptide have predicted cleavage five residues after the start of the motif. Precursors with a thuricin-type motif have predicted cleavage two residues before the end of the leader peptide motif. Precursors with a thurincin-type motif have predicted cleavage nine residues after the start of a leader and core peptide motif. Finally, cleavage for a clade of putative sactipeptide precursors with high homology to known precursors is predicted to occur seven residues before the end of the leader peptide motif. Predicting the reaction sites of the radical SAM protein AlbA represented a computational challenge, as its specificity is poorly understood. A recursive algorithm was implemented within PRISM to identify all potential sites of sulfhydryl to α-carbon bond formation such that the final molecule has the characteristic hairpin secondary structure of sactipeptides, at least two residues separate each cysteine-alpha carbon bond, and the final cysteine-alpha carbon bond is at least two residues from the end. When the cluster contains a homolog of the sporulation killing factor thioredoxin SkfH, only combinations with a single cysteine are considered, and the remaining two cysteines are linked by a disulfide bond. Otherwise, all combinations of three cysteines are identified. If present, homologs of either the sporulation killing factor membrane-bound protease SkfC or the split zinc-dependent protease AlbE/AlbF[26] are assumed to catalyze head-to-tail macrocyclization.

Streptide is the founding member of a unique class of macrocyclic peptides characterized by the covalent linkage of inactivated carbons from the side chains of lysine and tryptophan residues. Identification of putative streptide clusters requires the presence of the streptide precursor (StrA), a SPASM-domain-containing radical SAM protein (StrB), and the streptide transporter (StrC). Conserved N- and C-terminal motifs were identified based on a published alignment of streptide precursors. When only the N-terminal motif is identified, cleavage is predicted to occur 13 residues after its start. When the C-terminal motif is also identified, and cleavage one residue after its start produces a peptide of at least five amino acids, C-terminal cleavage is also predicted to occur. The SPASM-domain-containing radical SAM protein StrB catalyzes cross-linking between the β-carbon of a lysine residue and the C7 position of a tryptophan residue.

Thiopeptides are a large and complex family of RiPPs characterized by the presence of multiple thiazoles and a central six-membered nitrogenous ring (pyridine, dehydropiperidine, piperidine). Thiopeptides of the nosiheptide and thiostrepton families are further derivatized by the addition of an indolic acid or quinaldic acid moiety to form a second macrocycle. Putative thiopeptide clusters are identified by the presence of a dehydratase and a cycloaddition enzyme. Precursors are identified by a hidden Markov model, or by a heuristic strategy when a thiopeptide cluster is identified without any hits to the precursor hidden Markov model. This heuristic considers open reading frames of length 30-90 amino acids as potential thiopeptide precursors when they contain a sequence of 12 to 20 amino acids composed of at least 40% serines, threonines, and cysteines, and containing at least two serines.

Five conserved motifs were identified to predict leader peptide cleavage. Two conserved motifs corresponded to large clades of thiopeptides, with predicted cleavage three residues before the end of the first and four residues after the start of the second. More specific motifs were identified for thiostrepton and siomycin-type thiopeptides, with cleavage 32 residues after the start of the motif, and for nosiheptide and nocathiacin-type thiopeptides, with cleavage 33 residues after the start of the motif. For thiopeptides with C-terminal cleavage, such as thiomuracin and GE2270, N-terminal cleavage is predicted to occur 29 residues after the start of the motif, with C-terminal cleavage three residues after the end of the motif.

The biosynthesis of thiopeptide core scaffolds is characterized by a diverse set of conserved post-translational modifications, including dehydration of serine and threonine residues, heterocyclization and oxidation of serine, threonine, and cysteine residues, and cycloaddition of two dehydroalanine residues to form a six-membered nitrogenous ring. Using nomenclature from the simplest cluster, lactazole[28], we developed Hidden Markov models for core thiopeptide biosynthesis enzymes LazB, LazC, LazE, and LazF. As with the lantipeptide dehydratase LanB, homologs of the thiopeptide dehydratase LazB are assumed to catalyze the dehydration of any subset of serine and threonine residues to dehydroalanine and dehydrobutyric acid, respectively, with tautomerization of N-terminal dehydrated residues to pyruvate and 2-oxobutyrate. When at least two serine or threonine residues are present in the cleaved precursor peptide, a minimum of two dehydrations are assumed to occur. LazC is assumed to catalyze pyridine formation between an N-terminal dehydroalanine and any other dehydroalanine residue resulting in formation of a macrocycle of size 8 to β amino acids. Substituents at positions 1 and 2 are assumed to be fully heterocyclized and oxidized (i.e., to form thiazoles, oxazoles, or methyloxazoles) when possible. A separate hidden Markov model was developed for the distinct thiostrepton-type LazC enzyme, which is assumed to catalyze dehydropiperidine formation[29] between any pair of dehydroalanine residues resulting in 8 to 13 amino acid macrocycle formation. The cyclodehydratase LazE is assumed to catalyze heterocyclization of any subset of serine, threonine, and cysteine residues, and the oxidase LazF is assumed to catalyze azole formation at any overlapping subset of azolines.

A number of hidden Markov models were also constructed for tailoring enzymes specific to individual families of thiopeptides. Homologs of the berninamycin cytochrome P450 BerH catalyze β-hydroxylation of a valine residue. Homologs of the cyclothiazomycin protein CM catalyze tertiary thioether formation between a cysteine residue and a dehydroalanine residue. Homologs of the GE37468 cytochrome P450 GetJ catalyze the conversion of an isoleucine residue to β-methyl-δ-hydroxyproline. NocQ is a putative SAM-dependent methyltransferase from the nocathiacin cluster proposed to catalyze the methylation of a hydroxylated dehydrothreonine residue; since the enzyme responsible for dehydrothreonine hydroxylation is not known, homologs of this unique enzyme are assumed to catalyze both reactions. The nosiheptide protein NosA is a cofactor-independent enzyme whose homologs catalyze C-terminal amine formation by dealkylation of a terminal dehydroalanine residue[34]. Homologs of the nosiheptide cytochrome P450s NosB and NosC catalyze γ-hydroxylation of a glutamate residue and C-5 hydroxylation of a pyridine moiety, respectively. Hidden Markov models were constructed for four enzymes proposed to be involved in the biosynthesis of the (NosI, NosK, NosL, and NosN). However, because the exact function of each enzyme is unclear, the presence of the NosI acyl-CoA ligase alone is assumed to catalyze the esterification of the modified indolic acid observed in the nosiheptide structure. The carboxylic acid is assumed to react with a free cysteine or serine residue, while the hydroxyl group is assumed to react with the side chain carboxylic acid of a glutamate or aspartate residue. Homologs of the thiocillin nonheme iron-dependent hydroxylase TcID catalyze β-hydroxylation of a valine residue, while homologs of the SAM-dependent methyltransferase TcIO catalyze O-methylation of a threonine residue. Homologs of the 4-hydroxybutyrate dehydrogenase TpaJ, from the TP-1161 cluster, are assumed to catalyze conversion of a C-terminal threonine residue to an amino acetone group. TpdJ1 and TpdJ2 are cytochrome P450 monooxygenases from the thiomuracin cluster, which contains two cryptic oxidations (phenylalanine β-hydroxylation and isoleucine epoxidation). Since it is not known which cytochrome P450 catalyzes which oxidation, homologs of either of these two enzymes are assumed to catalyze either of the two possible reactions. Homologs of the GE2270 cytochrome P450 TpdQ catalyze β-hydroxylation of a phenylalanine residue. Homologs of the thiomuracin radical SAM protein TpdI and the GE2270 radical SAM protein TpdL catalyze thiazole 5-methylation, while the GE2270 radical SAM protein TpdM is assumed to hydroxymethylation of a methylthiazole moiety. Homologs of the GE2270 N-methyltransferase TpdT catalyze side chain N-methylation of an asparagine residue. Homologs of the thiostrepton amidotransferase protein TsrC catalyze the conversion of a C-terminal carboxylic acid to an amide, while homologs of the cytochrome P450 TsrR catalyze the oxidation of an isoleucine residue to form β- and γ-hydroxyl groups. As in the nosiheptide cluster, hidden Markov models were constructed for seven proteins implicated in the biosynthesis of the modified quinaldic acid moiety found in thiostrepton (TsrA, TsrB, TsrD, TsrE, TsrI, TsrT, and TsrU), but the presence of the TsrI esterase alone is assumed within PRISM to catalyze esterification of the quinaldate carboxylic acid at a free serine and the attachment of C-7 to the precursor peptide N-terminal amine.

Thioviridamide is a ribosomally synthesized natural product notable for its distinct repertoire of post-translational modifications, including the installation of five thioamide bonds and a unique serine-derived N-terminal acyl group. Identification of putative thioviridamide clusters requires the presence of the thioviridamide precursor and the putative thioamide-forming enzyme TvaH. Leader cleavage is predicted to occur immediately after the conserved N-terminal motif. Within PRISM, homologs of the TvaF decarboxylase catalyze aminovinylcysteine formation between a C-terminal cysteine and a serine or threonine residue; homologs of the TvaJ oxygenase catalyze histidine β-hydroxylation; and homologs of the TvaG methyltransferase catalyze histidine N1, N3-dimethylation. The candidate thioamide-forming enzyme TvaH is assumed to catalyze thioamide between the second and sixth residue. One of TvaC, TvaD, or TvaE is proposed to accomplish the transformation of the N-terminal serine residue to the unique acyl unit found in the structure of thioviridamide, with the presence of all three required to execute the virtual reaction.

Trifolitoxin is a unique RiPP with a UV-absorbing chromophore and potent antibiotic activity. The presence of the trifolitoxin biosynthesis enzymes TfxB and TfxC is sufficient to define the presence of a cluster, and to catalyze the conversion of a xQGC tetrapeptide within the cleaved precursor (TfxA) to the putative trifolitoxin chromophore. Cleavage is predicted to occur five residues before the start of the conserved motif in the core peptide.

YM-216931 is a cyclic RiPP characterized by a polyoxazole-thiazole moiety. Its biosynthesis is notable for a unique mechanism of heterocyclization. Putative YM-216391 family clusters are identified if they contain a precursor peptide and the distinct YmF macrocyclase. The identification of both N- and C-terminal conserved motifs is required to execute leader peptide cleavage, which is predicted to occur immediately after the end of the N-terminal leader peptide motif and eight residues before the start of the C-terminal motif. Within PRISM, cyclodehydration and oxidation of serine, threonine, and cysteine residues to form azolines and azoles is assumed to be catalyzed by the N- and C-terminal domains of YmBC, respectively. All possible cyclodehydrations are assumed to occur, but any subset of heterocycle oxidations is permitted. Homologs of the putative protease YmF catalyze head-to-tail macrocyclization. Homologs of the cytochrome P450 YmE catalyze β-hydroxylation of a phenylalanine residue. Finally, homologs of the YmB1 and YmC1 heterocyclase and oxidase catalyze formation of the unique phenyloxazole moiety from β-hydroxyphenylalanine.

Example B

Predicting Polyketide and Nonribosomal Peptide Natural Products Gene Clusters

The instant example illustrates exemplary experimental information for developing a system to predict natural product building blocks.

Developing a System to Predict Natural Product Building Blocks

Molecular studies have provided insight into the biosynthetic transformations and catalysts that promote PK and NRP biosynthesis. Advanced bioinformatic algorithms have likewise increased our capacity to identify biosynthetic clusters. As discussed above, we defined a new bio- and chemo-informatic platform—PRISM—which utilized a catalog of hidden Markov models (HMMs) in an attempt to better catalog PK and NRP biosynthetic reactions. Predictive capacity of PRISM for PK and NRP building blocks across 171 test clusters is provided here to define its accuracy for proteinogenic amino acids (93% accurate across 393 test cases), non-proteinogenic amino acids (94% accurate across 115 test cases), and PK acyltransferase (AT) domain substrates (74% based on 383 randomly selected AT domains). PRISM also identifies 257 building blocks added to NRP and PK scaffolds, including sulfurs, hydroxyl functionalities, formyl and methyl groups, halogens (100% accuracy across 30 clusters), fatty acyl units (100% for 20 clusters tested), and sugar molecules (64% accuracy of the correct sugar over 30 clusters)[56]. In the cases of deoxysugars, PRISM infers the numbers of sugars placed on a given PK/NRP scaffold from the number of associated glycosyltransferases (GTs), and determines their identities using annotated sugar genes, which facilitates monomer prediction. PRISM detects 5 dicarboxylic acid substrates, 132 fatty acids, 15 hydroxy acid substrates, 47 amino acids and several unique non-assembly line features, including 12 tailoring domains that are likewise detected via GRAPE.

Retrobiosynthetic Analysis of NRP Cores and PK/NRP Core Tailorings

Systematic retrobiosynthesis of microbial PKs and NRPs requires a strategy to reverse the various ring patterns, heterocycles, and other backbone elaborations (FIG. 2 and FIG. 3). To this end, we developed a Generalized Retrobiosynthetic Assembly Prediction Engine (GRAPE) within a Java framework (FIG. 2). GRAPE uses SMILES structures as inputs, and uses protocols from the chemistry development toolkit (CDK) to identify valences and bonds in order to deconstruct PK and NRP structures. GRAPE-based deconstruction logic and retrobiosynthetic processes were designed to handle the exceptional complexity of PK and NRP molecules, including well-known structures such as vancomycin, penicillin, and erythromycin (FIG. 2), along with many others (see FIGS. 43 and 44). By identifying predictable moieties and functional groups in PK and NRP chemical structures, GRAPE can leverage our knowledge of biosynthesis to reverse each reaction and reach the core components generated by an assembly-line enzyme.

In addition to backbone elaborations, amides of peptidic natural products are often modified during assembly line synthesis. GRAPE reverses such core alterations including N-, O- and C-methylations, imines, thioesters, esters and heterocycles (oxazoles, thiazoles, thiazolines, thiazolidines). When GRAPE reverses these modifications it also annotates the subsequent fragment with the reversed tailoring (see FIG. 44). Other prospective tailorings occur post scaffold biosynthetic assembly, such as p-lactam ring formation, prenylation, halogenation, sulfation, epoxidations, hydroxylations, bi-aryl and disulfide creation, which are also documented by GRAPE (see FIGS. 43 and 44). Maximum common substructure (MCS) matching is used to identify liberated fragments and monomers by comparison with an annotated library of PK and NRP monomer and tailoring units, including amino acids (297), singlet and doublet PK fragments (7), acyl adenylating units (67), fatty acids (132), uncategorized monomers (69) and sugars (71), (FIG. 3 and FIG. 4). GRAPE also identifies O, N, and C-linked hexose and deoxysugars, which are subsequently removed and logged for MCS search. All remaining unknown fragments are then scanned with a fatty acid-determining algorithm that has two filters. First is to check if the fragment has a carboxylic acid and no other elements, other than carbon or hydrogen for the remainder of the molecule, unless it is an oxygen on the γ-carbon. The second filter checks for the presence of a linear, nonbranching, saturated chain of at least four carbons. If both filters pass, the fragment is deemed a fatty acid.

Retrobiosynthetic Analysis of Complex PK and PK-NRP Hybrids

After MCS analysis is complete on all of the fragments, GRAPE identified amino acids, acyl adenylating units, fatty acids, sugars and biosynthetically uncategorised monomers. Remaining are three general groups of fragments, all of which may or may not be polyketide related fragments: ketide-extended hybrids, fatty acyl chains, and standard polyketides. Remaining fragments that contain amine and carboxylic acid groups, are potentially ketide unit extended hybrids. To analyze these, GRAPE identifies the longest carbon only chain from the α-carbon of the amine to carboxylate carbon of the furthest carboxylic acid (see FIG. 4). If the carbon chain has an odd number of carbons, the ketide-extended amino acid is identified as β-amino acid. The bond between β-carbon and γ-carbon is then broken and a carboxylic acid is added to the β-carbon to create the β-amino acid. If the carbon chain has an even number of carbons, the keto-extended amino acid is identified as a α-amino acid. The bond between the corresponding α-carbon and β-carbon is then broken, and a carboxylic acid is added to the α-carbon to create the α-amino acid. The amino acid fragment is reanalyzed by MCS to determine the exact amino acid, and the remaining polyketide fragment is then analyzed for its monomers.

In order to determine PK monomers, GRAPE reveals the longest carbon-only chain, starting from a carboxylate carbon, and predicts this to be the PK backbone. If the chain contains an even number of carbons, the second furthest carbon from the carboxylate carbon is selected as the biosynthetic starting β-carbon. In the case of an odd number of carbons in the chain, the furthest carbon from the carboxylate carbon is selected as the biosynthetic starting β-carbon. An iterative analysis of two carbon atoms from the backbone are processed at a time, marked as β and α, until the entire backbone is analyzed. The α-carbon chemical environments are used by GRAPE to derive the biosynthetic dicarboxylic acid that would have been selected by the PKS AT domain in biosynthesis. For instance, if the α-carbon has a hydrogen, this infers malonate (Mal), CH3— methylmalonate (MeMal), OCH3— methoxymalonate, and CH2CH3 for ethylmalonate (see FIG. 5). Similarly, β-carbon chemical environments define the oxidative status of β-ketone. Salient features to discern a PK chain from fatty acyl chain are also considered after the polyketide prediction is complete. If a majority of the β-carbons are fully saturated, the fragment is ambiguously labelled as a fatty acid or a polyketide since its biosynthetic loading modules cannot be definitively determined based on structure.

Type I PKs can include a number of complex post-assembly line cyclizations, which can occasionally remove the generalized predictability of a carboxylate (end carbon) or the start carbon, so predicting the PK scaffold is not possible without reverting these post-assembly modifications. Building on established biosynthetic paradigms, GRAPE includes a series of retrobiosynthetic operations to process these challenging structures (see FIG. 43). A number of other, more esoteric chemistries are also processed and recorded (see FIGS. 43 and 44). For instance, ether-containing rings, including polyethers, such as monensin, are opened and attached to the appropriate atoms depending on which of the carbons is a β-carbon, in the case of even-numbered carbon rings. With an odd number of carbons, it is impossible to tell which carbon had the hydroxyl group and which had the ketone, so both are inserted as potential states at that site (see FIG. 43 ).

Having constructed breakage rules that cover a wide spectrum of chemistries found within the PK and NRP family, we next focused our attention to test GRAPE on example molecules. Outputs of the molecules erythromycin, thiocoraline, ML-449, salinosporamide, cephalosporin, penicillin, nocardicin, chivosazole A, curacin, bleomycin, kendomycin, avermectin, piercidin, anthramycin, eponemycin, monensin, mupirocin, arthrofactin, mycoplanecin, SW163 C, vancomycin, A-47934, apoptolidin and yersiniabactin are shown in the FIGS. 43 and 44. In addition to the chemistries above, created from multi-modular assembly lines, GRAPE also includes a strategy for type II and enediyne polyketides. In these instances, GRAPE first removes tailorings and, because they are generated iteratively, it uses the entire core scaffold for matching. The GRAPE-derived skeletons are then compared with a repository of scaffolds for each type that has been compiled, and a substructure search is done on the query compound before it is broken down by other parts of GRAPE. If the scaffold is found to be in the query compound, it is then labelled as that type of molecule. Analogous to the sugar example above, a collection of genes is ascribed to each type II aromatic and enediyne scaffold type and these gene sets are outputted for comparison with PRISM.

Generation of a Scoring Algorithm to Connect Natural Products to Orphaned Natural Product Gene Clusters In order to link biosynthetic clusters and their products, we created GARLIC to align monomers from cluster predictions and small molecule breakdowns. Alignment algorithms are used for matching other biomolecules, such as nucleic acids and proteins, often with query searches through a database of subjects, and generally are DNA on DNA or protein on protein. For natural PK and NRP biomolecules, this requires an added dimension of comparing gene clusters (DNA) to final products (small molecules), and with it, are several unique challenges that hinder algorithm development. These range from degeneracy of the code (from protein to small molecule), inconsistent collinearity (from gene to small molecule) and the wider spectrum of comparable traits/monomer blocks (fatty acyl units, sugars, amino acids and carboxylic acids). In nucleic acid- and protein-based alignment, the numbers of monomers are relatively small, being 4 and 20 residues, respectively. According to our GRAPE analysis, within the PK and NRP realm are 20 PK monomers (5 substrates, each with 4 possible oxidation states), 47 amino acids and a collection of tailoring blocks (e.g. sugars) and fatty acids, to name a few. Moreover, code degeneracy and collinearity for PK and NRP systems leads to many error possibilities (differential substrates incorporated and ordering of incorporation), which is different from the genetic code degeneracy (e.g. multiple tRNA for the same amino acid) and defined collinearity from DNA-RNA-protein. PKS and NRPS small molecule machineries are well noted for their skipping, stuttering, code degeneracy, leading to errors and numerous nuances in collinearity. To better communicate the complexity of PKS and NRPS collinearity and the considerations necessary to relate them to PK and NRP small molecules, the following scenario is provided. For a gene cluster whose final product contains blocks 'ABCDE', there are a number of derivations. In one instance, ABC may be encoded by one gene, and the others on different ORFs. Written differently, this would represent ABC-D-E (dashes indicate different genes), order of ABC monomers may be fixed in this case as they are encoded on the same ORF. Order of the others, D and E, cannot be assumed, as a series of combinations are plausible: D-E-ABC, E-D-ABC, E-ABC-D, etc.). Obviously, the number of permutations increase the more dissociated the modules are across ORFs, all of which would relate to the same compound containing A,B,C,D and E blocks. If there were eight monomers encoded by eight separate genes, the number of permutations is 8! or 40,320.

Since it is computationally prohibitive to align every possible permutation, a random sample of permutations is taken using the Fisher-Yates shuffle. Each permutation is scored and the top scoring subset is retained; each remaining permutation is used as a seed to create new permutations, by swapping the positions of two ORFs picked randomly, per permutation. This is done many times and the top scoring subset is again saved. This process is repeated several times, approaching the optimal alignment without searching the entire permutation space. The final score is then determined by the highest-scoring alignment from the permutations. For this analysis, when there were 6 (720 permutations) or fewer ORFs, all permutations were considered and aligned to GRAPE outputs; when there were greater than 6 ORFs, the heuristic refinement method stated previously was used.

Figure 6:
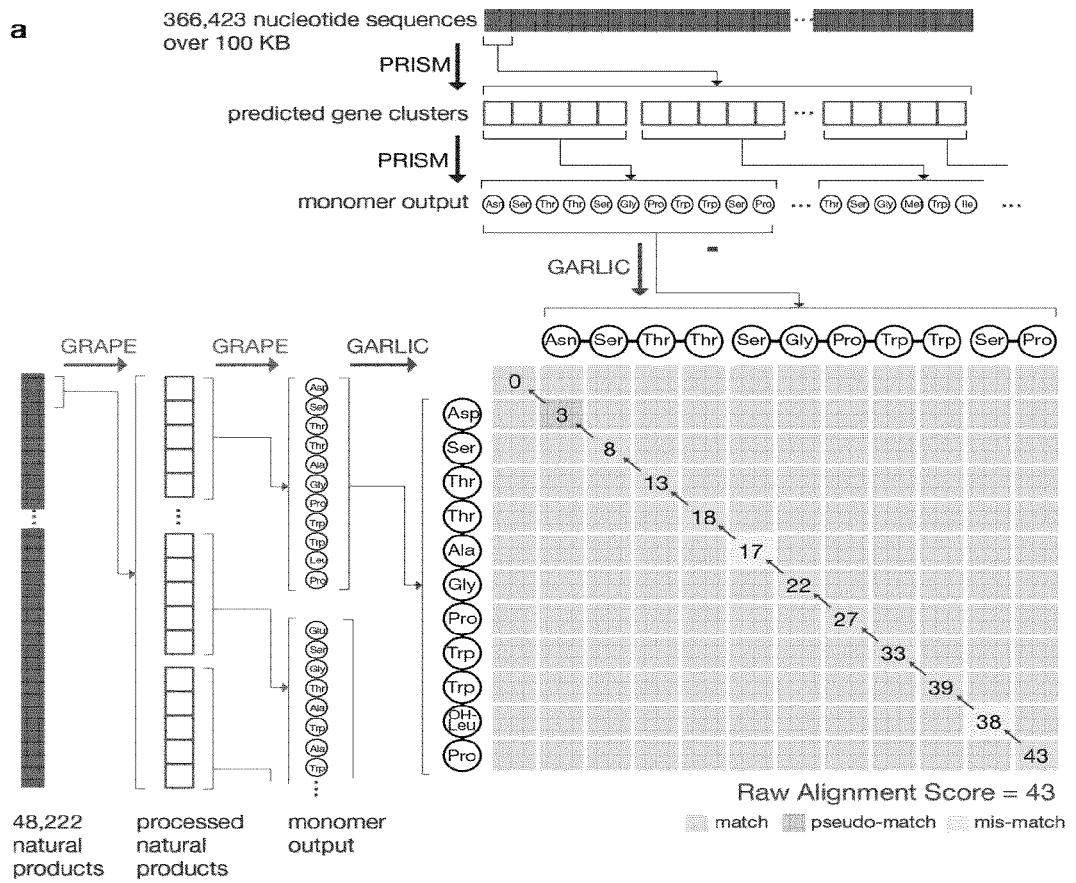
FIG. 6 demonstrates Matching algorithm of the Global Alignment of natuRaL product cheminformatICs (GARLIC) and examples of natural products matched. (a) Matching algorithm of GARLIC between PRISM and GRAPE outputs. The genetic information used in PRISM are nucleotide sequences that are over 100 kb from NCBI. Compounds used in GRAPE are microbial natural products from in-house database. (b) Examples of natural products (telomycin, arylomycin, fusaricidin and megalomicin) matched between PRISM and GRAPE.

Multiple parameters of the alignment algorithm demand consideration, given the diversity of monomers and assembly line alterations, as well as the difficulty translating from genes to small molecule blocks. In totally, we developed a series of 26 different parameters that could be considered and we integrated them into alignment schemes. Some of this included weighting based on the known distribution of monomers found in NRP and PK molecules. Surveying the known PK and NRP chemical space via GRAPE revealed non-proteinogenic amino acids to comprise 6.7% of all amino acids, and of the 62.4% that are proteinogenic, 30.9% are aromatic. In PKSs, malonate is the most widely used (70.8%), followed by methylmalonate (23.7%), leaving the more rare units at 5.5%. Other parameters for consideration include development of potential scoring based on the accuracy of PRISM predictions for the respective substrates, and tailorings. Examples of these include hydroxylases, chlorinases, sulfotransferases and the different sugar types. To match liberated sugar components from GRAPE, a sugar gene repository that contains a list of possible genes for each sugar from GRAPE was constructed to directly match to PRISM's predicted sugar genes. Following reversal of tailoring reactions, results of the liberated monomer matches were recorded and outputted in a format consistent with PRISM gene cluster prediction outputs, facilitating cross-platform comparisons that can correlate deconstructed molecules with their corresponding biosynthetic gene clusters (FIG. 6).

Two major forms of alignment algorithms are commonly used depending on the data domain and the purpose of the alignment: Smith Waterman (local) or Needleman Wunsch (global). Local alignments may consider only a subset of the original sequences to produce an optimal score, whereas global alignments are often deployed when one wishes to define the likeness between two sequences as a whole. Given the challenges of converting data from genome to small molecules, we created a test set with 171 diverse PKs and NRPs having annotated gene clusters. To conduct an unbiased analysis, we considered these structures and their respective GRAPE breakdowns of all of the other known NRP and PK structures from our database of 48,222 compounds. To assist in establishing cluster matches, we developed a relative scoring metric, where the final score was derived as a ratio between a score of a given GARLIC alignment and the maximum score of the cluster or compound in the alignment. This provided a comparative value that reflects how well a given match is for a specific cluster in relation to the maximum possible score for each subject and query, whichever is higher.

For each of the 171 biosynthetic gene clusters, we performed GARLIC scoring under various algorithm configurations against each of the compounds, including both compounds made by the gene clusters and all others from the database. In deriving the final algorithm, we developed a number of criteria and developed, through continuous empirical testing, a refined algorithm that has differential scoring for each of the given parameters. We performed this analysis on five algorithm configurations, including local and global alignment under basic scoring schemes, and global alignment based on a scoring scheme that factored in the above listed distribution of monomers in PK and NRP products, with heightened scores for rare or uncommon blocks. Though the global alignment outperformed the local alignment with basic scoring schemes, improvements were noted when the scoring was refined. Particularly important refinements were the sugar-gene matching score, as it was far too high in the basic scoring scheme, the introduction of partial matching for amino acids, and rare amino acid/polyketide substrate bonus scores. Our refinements to the scoring scheme based on biological knowledge gained from previously mentioned GRAPE monomer analysis and PRISM accuracy measurements led to slight improvements. Additional score refinements of information external to the biosynthetic assembly line, such as sugars and chlorinations, further increased the number of correct matches. 78% were successfully matched, 86% including family matches. There were 134 direct matches (dark blue), 13 family matches (blue) and 24 no matches (light blue), which comprised of 78%, 8% and 14% of the test clusters, respectively. Structures of 11 compounds (FK506, BE14106, jamaicamide, kendomycin, erythromycin, daptomycin, bleomycin, vancomycin, capreomycin, pyochelin and anthramycin) were provided as examples. Within the 134 matched clusters, 95% of the clusters have a final score that is higher than or equal to 0.33. We also determined the average final score for each compound class: 0.73 for PK, 0.69 for NRP and 0.59 for PK/NRP. Our program works on type II aromatic PK and enediynes as well.

Algorithmic Global Matching of Biosynthetic Clusters to Known Natural Products and Defining Clusters for the New Natural Products.

To build a comprehensive collection of bacterial NRP and PK biosynthetic gene clusters, we developed a script to extract and profile microbial genomes (both from NCBI and our internal library) using PRISM. Over 300,000 sequences with a length of >100 kb were analyzed, leading to the identification of 8,888 PKS and NRPS with at least three modules or full gene clusters with 20 kb on each side of the clusters (1,988 PK, 3,413 NRP and 3,487 hybrid PK/NRP gene clusters). To assess which gene clusters corresponded to known compounds, PRISM results were run through GARLIC, and final matching scores for known products were recorded. By picking the top ten compound matches for each cluster mentioned above, we identified 17,559 PK and NRP compounds (4,044 PK, 6,951 NRP and 6,564 hybrid PK/NRP) as the potential products of the 8,888 identified clusters. Included in these results were a series of dereplicated gene clusters that were previously related to natural products, including accurate matches for telomycin (27), acidobactin (9), thanamycin (9,28) and potensimicin (9), further extending the 134 listed above. More importantly, a number of other candidate gene clusters to compound matches were revealed that had not previously been made from this metagenomic dataset (FIG. 5). Using the final score averages to the true positive matches as a guide (see above), we focused in on compounds that were above these scores as representative candidates from each class: PK, PK/NRP and NRP. Moreover, we did not use strains that had been known to produce a given molecule in the literature. Strains were sourced, cultivated and processed to generate crude extracts. For all cases we properly identified the prospective candidate, and were able to assign *Streptomyces achromogenes* NRRL 3125 as a producer of the PK lucensomycin (final score: 0.79) (29), *Amycolatopsis* sp. NAM 50 as a producer of the PK/NRP octacosamicin (final score: 0.58) (30), *Brevibacillus laterosporus* DSM 25 as a producer of the NRP bogorol (final score: 0.78) (31) and taurinamide (32), respectively.

A central reasoning for developing the GARLIC platform and creating the retrobiosynthetic analysis was to define assembly lines that will code for new PK or NRP molecules. Our capacity to develop a scoring metric for the system enabled us to also define examples of assembly lines that have a high likelihood for encoding new molecules. Since 95% matched to known clusters in our test set with a final score of 0.33 or higher (see above), we can hypothesize that any full clusters with the top match score lower than 0.33 are likely to code for novel compounds. Among the 8,888 full clusters, 2,978 (33.5%) had scores <0.33, suggesting they code for novel products. As an initial demonstration of this, we selected a cluster from the potensimicin producer Nocardiopsis potens DSM 452349 that had a low match score (0.30) to all known compounds. Using metabolomic profiling through the Genome to Natural Products platform (GNP), we identified the orphan metabolite based in part on its prediction. The isolated product was structurally characterized and determined to be a new natural product, which we named potensibactin. Loading the potensibactin structure into the identified natural product database and re-running GARLIC validated this product as a match for the deorphaned cluster (final score of 0.56).

Discussion of the Results of Example B Presented Above

Since the dawn of the 'golden age of antibiotics', much effort has been taken to collect and solve the structures of microbial natural small molecules. Success in these efforts is illustrated by the vast caches of products isolated and the activities of numerous agents that have been determined and are currently used in medical and biotechnological applications. Genomics is a more recent addition to the natural product workflow, and is assisting with how we define microorganisms with biosynthetic potential and the overall distribution of PK and NRP clusters in microbial genomes. Reconciling the rapidly expanding amount of genomic data with natural products chemistry is now a requirement in order to define the next frontiers for pursuing natural small molecules. We also need to recognize that the sequenced genomes that we currently have are biased towards the "classical" producers of bacterial natural products (actinomycetes) and pathogenic bacteria (*Escherichia coli* and *Pseudomonas* spp.), which is not the true representation of the genomic spaces and its capacity to produce novel compounds. Therefore, the potential for novel cluster discovery would be much higher if we have more diversity in the sequenced genomes. Now merging such tools with other developments in comparative metabolomics should now make it achievable to construct targeted libraries of strictly new microbial natural products, bypassing the challenges of finding knowns in bioactivity-guided fractionation. Here we present the unified tools of gene cluster prediction (PRISM), known natural product retrobiosynthesis (GRAPE) and alignment processes (GARLIC) that work as a pipeline to define new clusters and those for known compounds. The GARLIC algorithm allows for the comparison of clusters to small molecules through the upload of PRISM results or through manual input of scaffold and tailoring information obtained from other sources. The new clusters and their encoded products may be the next step for medicine to develop effective new agents, particularly in this current era of antibiotic resistance.

Different embodiments of the invention have been shown by the above example. Those skilled in the art could develop alternatives to the methods mentioned above that are within the scope of the invention and defined claims.

Example C

Characterizing Anti-Bacterial Natural Products

The instant example illustrates exemplary experimental information for charting natural antibiotics in connection with the instant disclosed methods and systems.

Charting Natural Antibiotics

Figure 14:
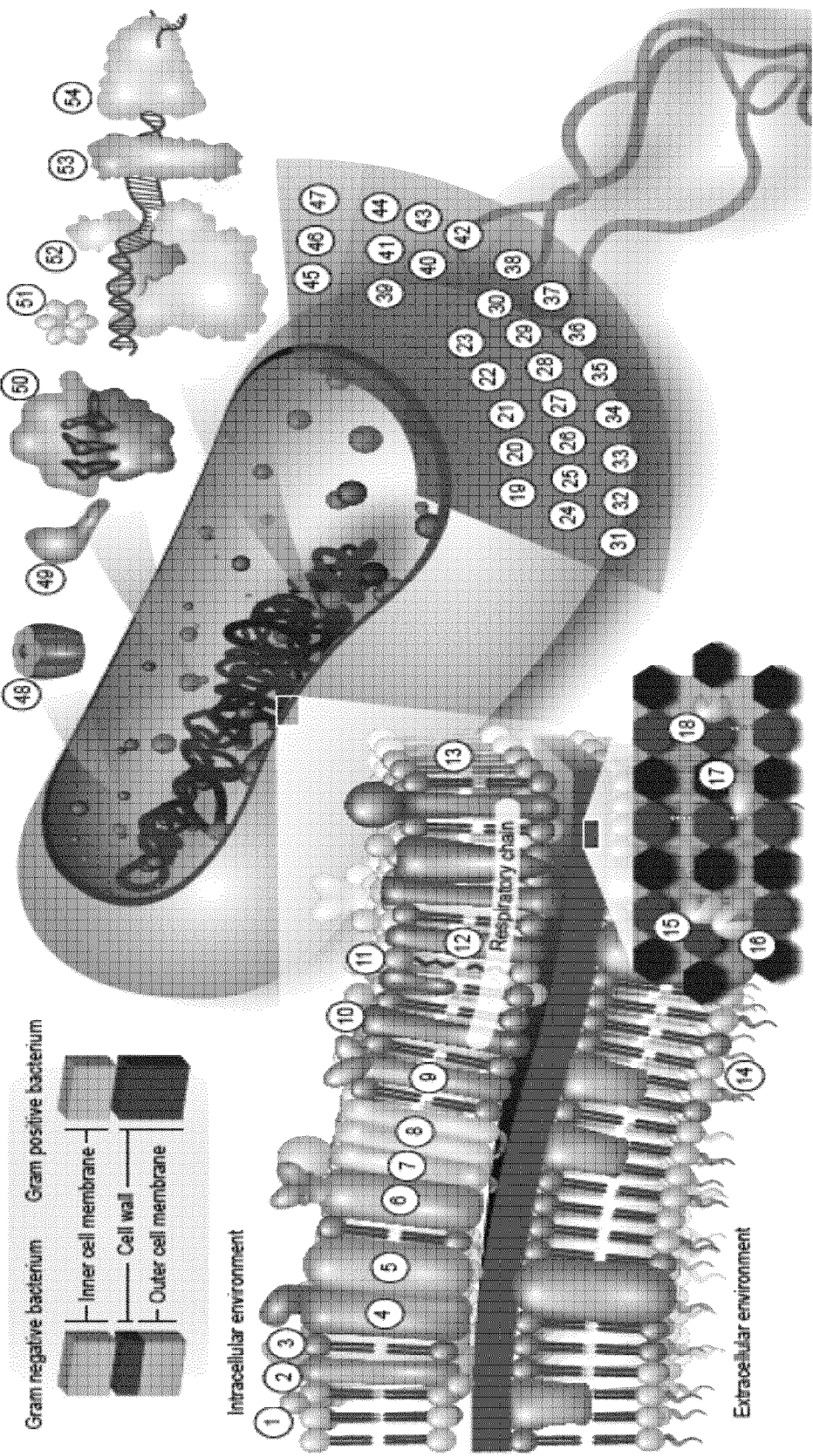
FIG. 14 pictorially represents 54 natural antibacterial targets identified through compound specificity analysis.
Figure 15:
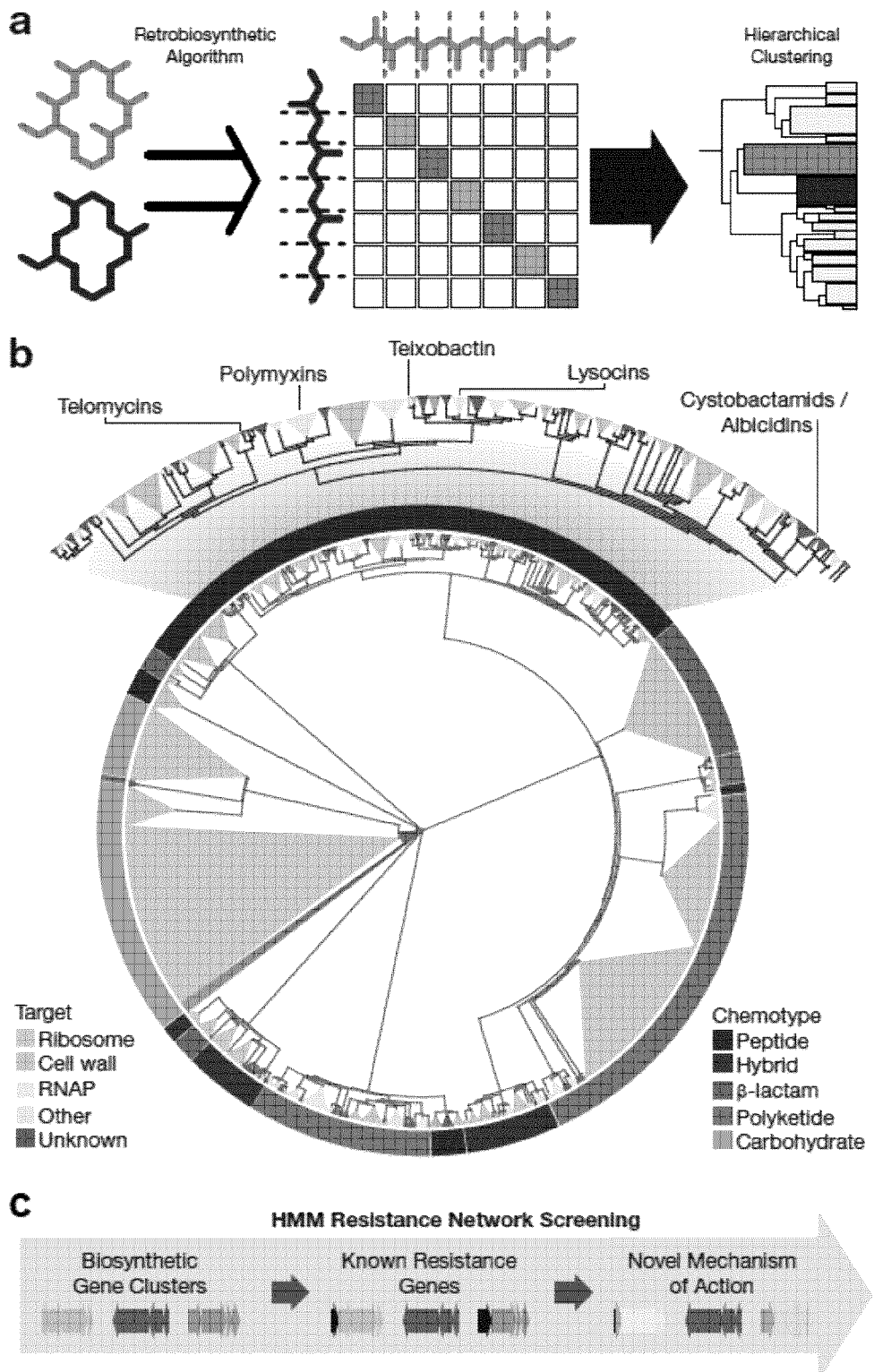
FIG. 15A pictorially demonstrates antibacterial fingerprint alignment.
FIG. 15B demonstrates a map of chemoinformatic relationships of all members of these classes and define groups of specific antibiotics with no known mode of action.
FIG. 15C demonstrates the steps of hidden Markov model (HMM) resistance network screening, underscoring the ability of this analysis to identify antibiotics with novel mechanisms of action.

In contrast to growing genetic databases detailing the biosynthetic origins of natural products, there has been little progress in the development of a comprehensive annotated chemical database of extant microbial antibiotic natural products. Our systematic analysis of antibacterial natural products was initiated by incorporating an up-to-date version of the Handbook of Antibiotics and extensive reviews of published literature and patents into a single database. Chemical structures for each known antibiotic were generated and rendered in SMILES format (10,343 compounds). Manual annotation of the specificity of each compound identified that 7,184 molecules demonstrated non-specific antibacterial activity while 3,159 displayed specific antibacterial activity. This specificity analysis involved a comprehensive review of primary literature for each natural product described, assessing bioactivity towards bacteria as well as fungi, plants, human cell lines, and animals. Non-specific antibacterials were found from fungi (35%) as well as bacteria (66%), while specific antibacterial agents were significantly enriched in bacterial producers (96%) as opposed to fungi (4%), where specific antibacterials were most often fusidic acids, mutilins, and penicillins. Meta-data related to the known or suspected mechanisms of action of these specific antibacterials was also incorporated into our analysis, revealing 54 described natural antibacterial targets (FIG. 14). Antibiotic classes that make use of modular biosynthetic pathways were segregated for analysis, including ribosomal and nonribosomal peptides, polyketides, β-lactams, and carbohydrate or aminoglycoside superfamilies. To generate high fidelity subgroupings of these molecules, we developed a retrobiosynthetic algorithm that could utilize biosynthetic and chemoinformatic logic to assign likeness, as opposed to classical chemoinformatic metrics such as Tanimoto similarity scoring. The limitations of chemoinformatic relationship scoring using Tanimoto have been reported previously, particularly with molecules that are as diverse as natural products. To facilitate high-fidelity clustering, our new algorithm was designed to integrate the distinct biosynthetic origins of the aforementioned modular natural product superfamilies, identifying substrates contained within these antibiotics, and the monomers used in their construction. We reasoned that this retrobiosynthetic algorithm could retrace the evolutionary histories of these selective antibacterial agents and provide a means of allocating them into defined sub-groups. This program selectively deconstructs molecules from modular natural product superfamilies using a series of custom tailored rules to provide a proto-scaffold consisting of the originating building blocks. Each series of individual components are used as a fingerprint for their respective antibiotic, facilitating antibacterial fingerprint alignment via a Needleman-Wunsch algorithm (FIG. 15). By processing this data through hierarchical clustering, we reasoned that we would have a protocol (see Methods) sufficient to reveal the chemoinformatic relationships of all members of these classes and define groups of specific antibiotics with no known mode of action. Results of this analysis were readily organized into sub-families comprising 1,908 distinct molecules, with an exceptionally low rate of incorrect localization during clustering (<0.5%; FIG. 15B).

Parsing the accumulated antibiotic data revealed the distribution of molecules with specific antibacterial activity originating from modular biosynthetic assemblies. Within these groups, 668 molecules were of peptidic origin, followed in abundance by polyketides (571), carbohydrates (354), β-lactams (196), and hybrid molecules (119). The majority of the molecules in our analysis belong to subfamilies with known mechanisms of action (88.3%), spanning 32 established antibacterial mechanisms (FIG. 14), while molecules without established molecular targets are rare (11.7%; FIG. 15B). The discrepancy between all known targets and the targets identified in our analyzed subset of antibacterials largely reflects small antimetabolites that interfere with amino acid metabolism, and which did not yield usable alignment data following deconstruction via our retrobiosynthetic algorithm. Nonribosomal peptides demonstrated the most variation in their modes of action, including 22 distinct molecular targets. Polyketides and hybrid assembly structures also demonstrated considerable diversity, with 10 and 7 antibacterial targets respectively. Collectively, these products were shown to affect 30 distinct targets. For the β-lactams (3), and carbohydrates (2) the list is much smaller, despite the fact that these groupings have a large number of individual members, the target diversity is relatively narrow. Inhibition of the ribosome was the most frequently observed antibacterial mechanism, including 45% (851 molecules) of the specific antibacterials from our modular antibacterial natural product sample, corresponding to 51% of those with known mechanisms (FIG. 15B). Inhibition of cell wall biosynthesis through various molecular targets was the second most frequently observed mechanism of the sampled antibacterials with known mechanisms (26%; 441 molecules) followed by inhibition of RNA polymerase (4.3%; 73 molecules). Analysis of higher order families (such as thiazolyl peptides, glycopeptides, or aminoglycosides) demonstrated the frequency of distinct, evolved scaffolds inhibiting a given target. The ribosome was again observed as the most frequent hit, and was the target of 19 distinct families from our sample of antibacterials with modular biosynthetic origins. RNA polymerase was also a frequent target with 9 distinct families of inhibitors, as well as DNA gyrase, which was the target of 5 distinct classes. Notably, of the 137 distinct families observed in our sample of 1,908 modular, specific antibacterials, 54 did not possess known mechanisms of action. This also indicates that the 83 molecular classes with known mechanisms in our sample covered 32 molecular targets, indicating a frequency for new scaffolds inhibiting new targets of nearly 40%. Closer inspection of well-established targets such as the ribosome or RNA polymerase shows that individual natural product scaffolds bind a wide variety of sites on these macromolecular assemblies[106-107], demonstrating that assembly line antibiotics will evolve to create chemical and biological diversity. Analysis regarding the specificity of these diverse natural antibiotics for their established targets is well characterized in primary literature and reviews.

This sampling of natural antibacterials demonstrates that certain structural classes are more effective at generating chemical and biological diversity than others. Peptide antibiotics were found to have the highest degree of chemical and mechanistic diversity, as well as the largest number of subfamilies without known mechanisms of action. Given the nature of their modular biosynthetic machinery and the degree to which monomers and scaffolds can be tailored, nonribosomal peptides offer the greatest number of combinations and permutations for natural selection. These peptides appear to be uniquely capable of interacting specifically with structural small molecules or membrane components, and can act as potent bactericidal agents.

Creating a Resistance Determinant Library

A salient feature in the hierarchical clustering data reached through our retrobiosynthetic analysis is that subfamilies share a chemical scaffold and a common mechanism of action. With this unique analytical capacity, we could rapidly define all subfamilies from our sampling of the natural antibacterial collective, on the basis of their chemical structures and shared biosynthetic components. To interrogate the genetic origins of promising subfamilies, we devised a bioinformatic web application for detecting and displaying biosynthetic gene clusters, PRISM. By utilizing a series of hidden Markov models (HMMs), BLAST databases, and chemoinformatic algorithms, PRISM detects known and unknown gene clusters, provides similarity scores with known biosynthetic clusters, produces high fidelity predictions of chemical scaffolds, and identifies all known self-resistance determinants (Methods). Several key works have underscored that resistance is often disseminated from antibiotic producing organisms and is associated with biosynthetic gene clusters for antibacterial agents[86,87,90]. Classically, this collection of known resistance determinants has been used to expedite the tracking and spread of antibacterial resistance in a clinical setting. Now, by associating self-resistance determinants with known antibacterial mechanisms, PRISM can scan biosynthetic gene clusters for resistance genes that can predict antibacterial targets. By combining known cluster scoring, chemical predictions, and resistance screens, this pipeline can assist in validating antibiotics and prioritizing those with unique mechanisms that lack cross-resistance (FIG. 15C).

To facilitate optimal detection of resistance genes, we collected self-resistance determinants from all known antibiotic pathways and derived 108 HMMs that span mechanisms involved in drug efflux, drug modification, target alteration, and decoy targets (FIG. 15C). This database was subsequently paired with previously collected HMMs from clinically observed resistance genes to provide a comprehensive means of detecting known resistance genes. To assess the use of our pipeline for profiling self-resistance determinants that indicate mechanism, we loaded a series of biosynthetic gene cluster DNA sequences into PRISM. Biosynthetic genes were automatically detected and depicted, and known molecule identity was determined. PRISM generated predictions of the natural product structure, assessed similarity to gene clusters with known products, and identified a diverse series of scaffold- and target-specific resistance genes. Using the integrated HMMs, PRISM detected resistance determinants in each analyzed cluster that were telling of the activity for the chemical class produced. As unique structures are necessary, but not sufficient for a unique mechanism of action, this pipeline provides a crucial second measure to ensure that targeted rare scaffolds possess similarly uncommon modes of action without cross-resistance.

Investigation of the Mode of Action of Telomycin

Figure 17:
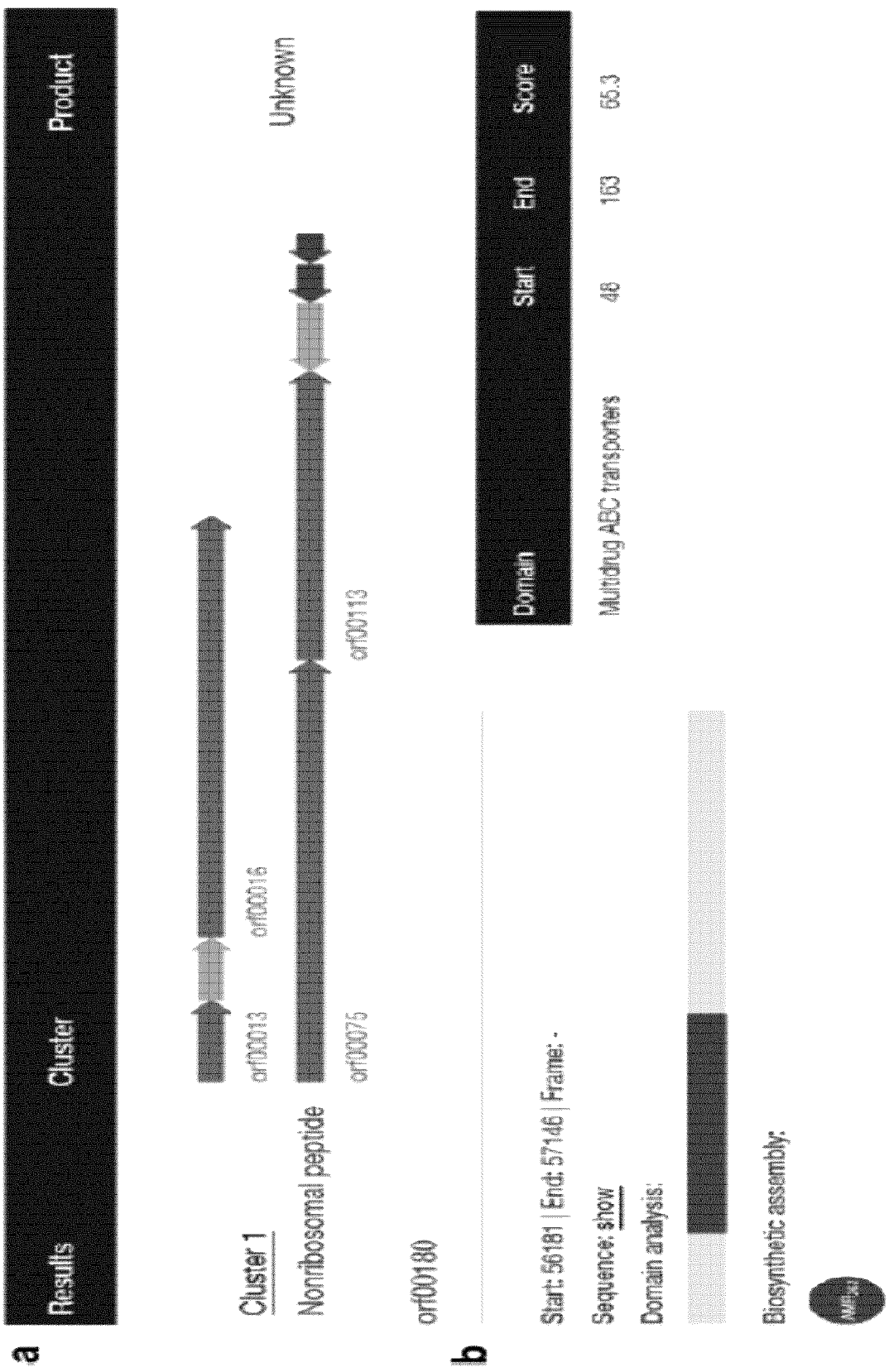
FIG. 17 demonstrates the analysis of the PRISM telomycin biosynthetic gene cluster as it is passed through a resistance screening pipeline FIG. 18 graphically demonstrates that telomycin does not cause hemolysis as lysis of red blood cells was studied in varying concentrations of telomycin.

Based on our defined retrobiosynthetic clustering of antibacterial natural products, we sought to investigate underrepresented chemical scaffolds with the potential to possess uncharacterized molecular targets. Given their structural and mechanistic diversity, we chose to investigate nonribosomal peptides in particular. From a series of promising candidates including, among others, the pyloricidinsand griselimycins, we chose to investigate the telomycins, which possess potent bactericidal activity against a wide range of Gram positive organisms. The telomycin-producer, *Streptomyces canus* ATCC 12647, was purchased from the ATCC and submitted for genomic sequencing. Using PRISM, we were able to quickly identify a candidate telomycin biosynthetic gene cluster from the assembled contigs (Telomycin structure, FIG. 16A). The telomycin gene cluster was found to encode three nonribosomal peptide synthetases and a series of accessory enzymes consistent with formation of the telomycin undecapeptide core, precursor supply and tailoring (FIG. 16A and FIG. 16B). When this biosynthetic gene cluster was passed through our resistance screening pipeline, no genes were identified with similarity to known specific self-resistance determinants (FIG. 17), consistent with a unique mechanism of action. These results are consistent with previous observations that the telomycin-related molecule LL-AO341β does not demonstrate cross-resistance with other antibacterial agents. This automated assessment of potential resistance profiles supported additional efforts to be directed toward describing the mechanism of action of telomycin.

Figure 18:
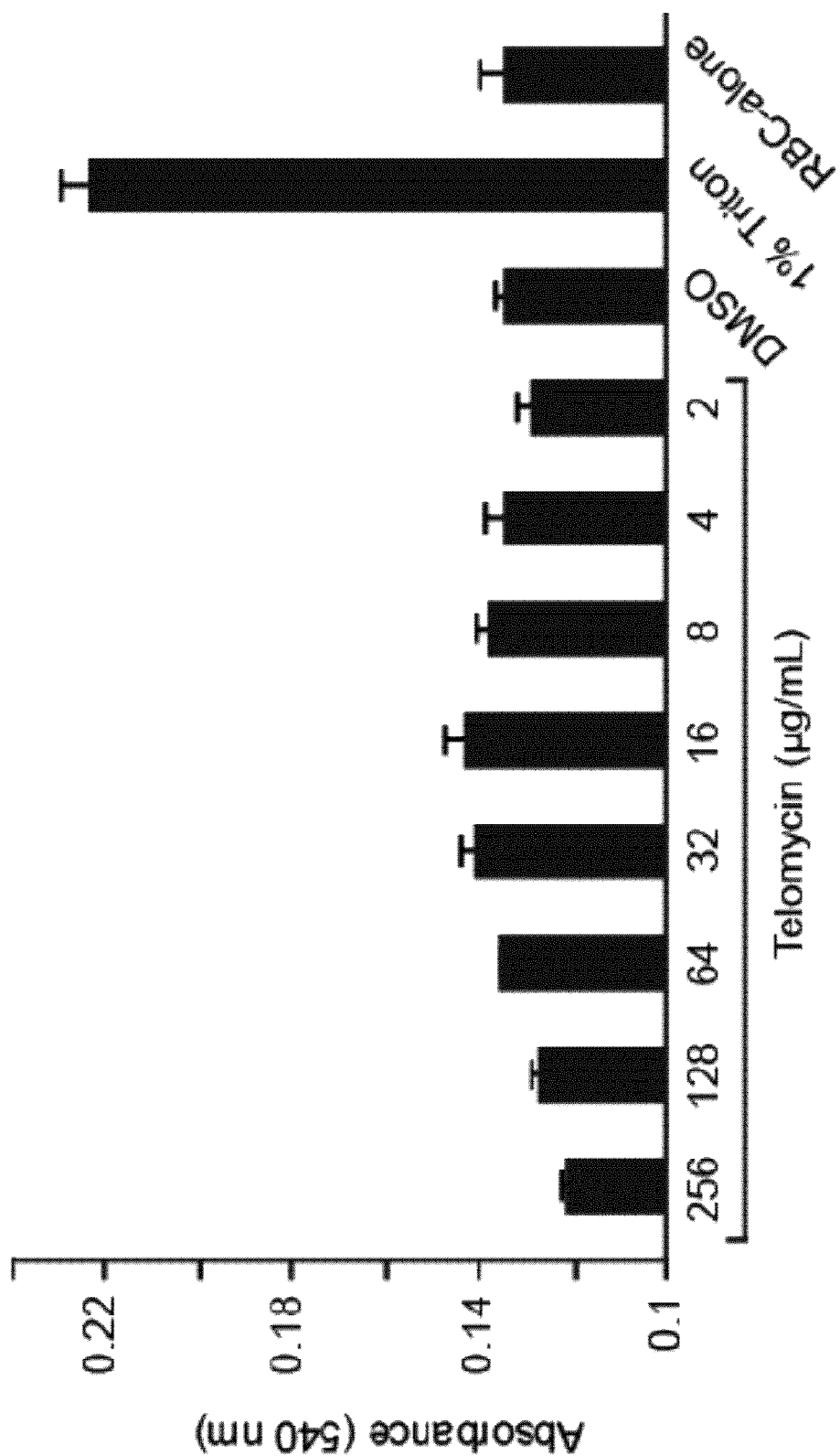
Figure 20:
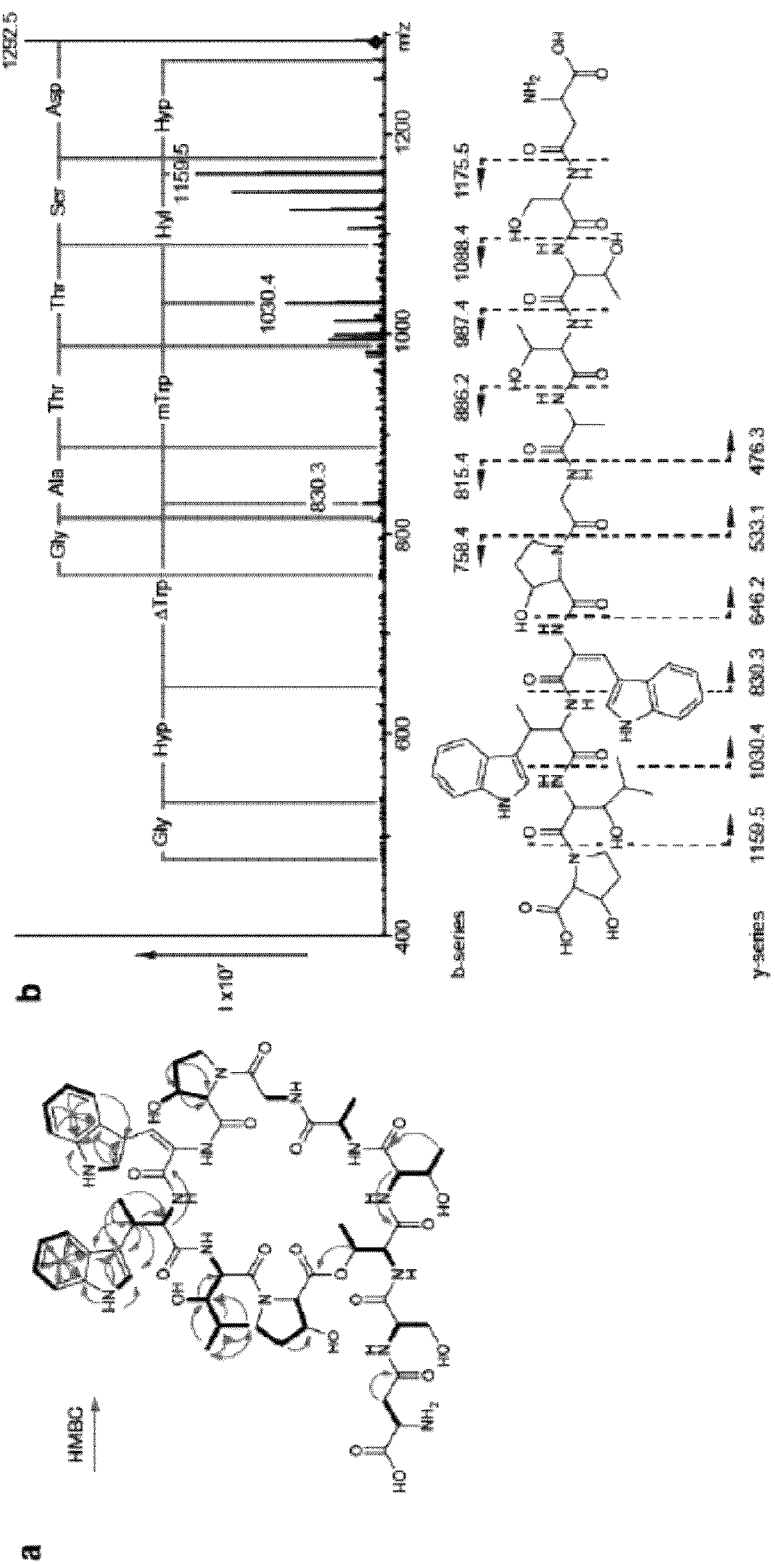
FIGS. 20 to 29 show the structure and characterization of 10 telomycin analogs (compounds 1-10).
Figure 21:
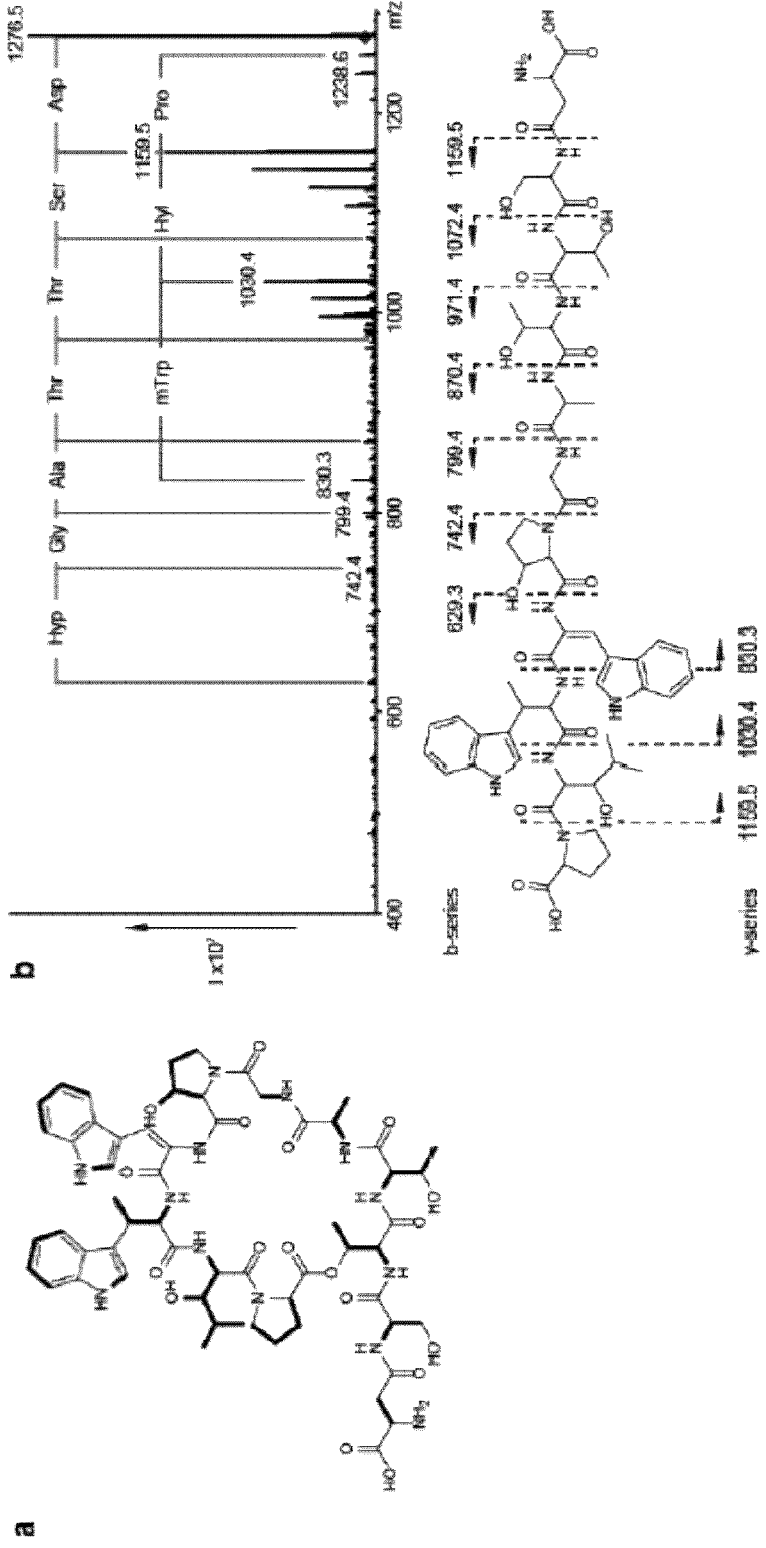
Figure 22:
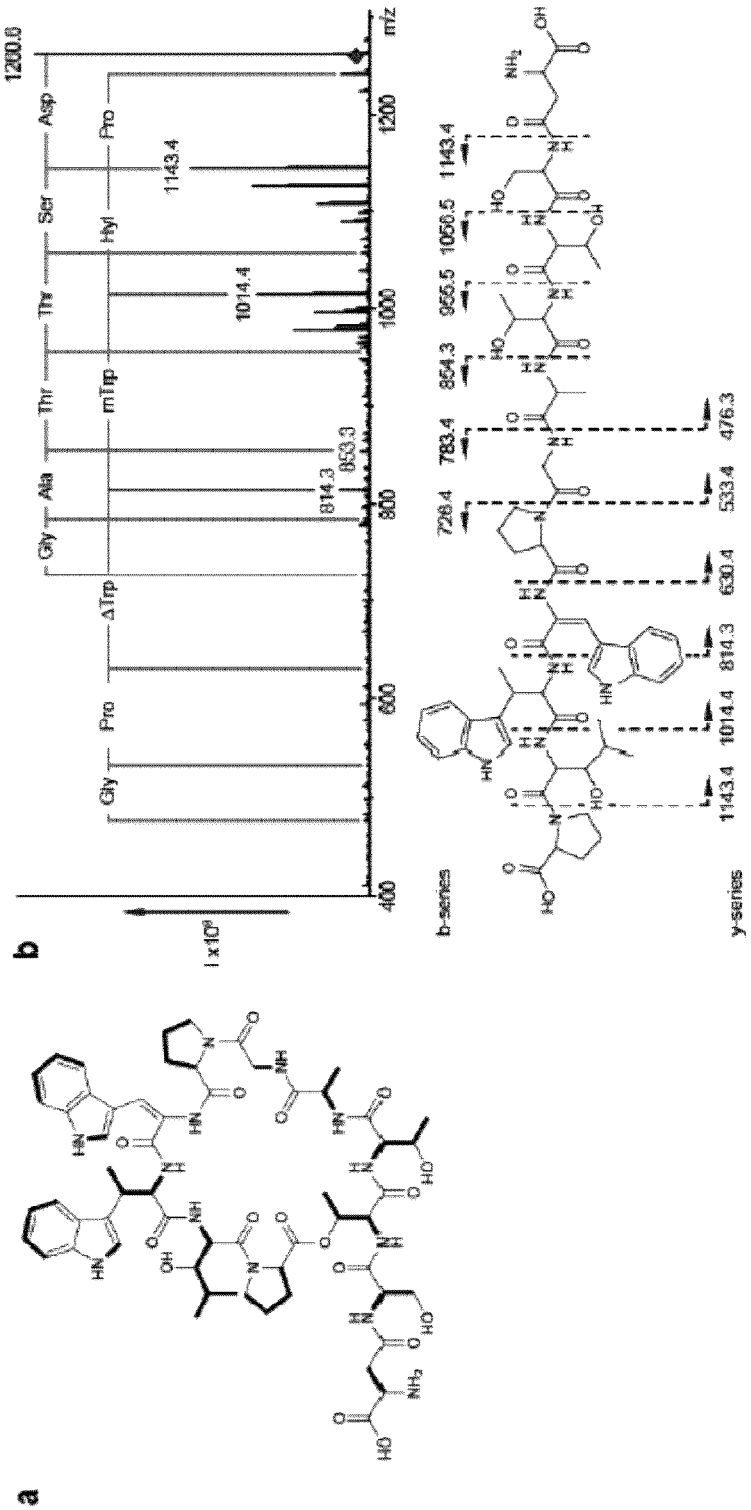
Figure 23:
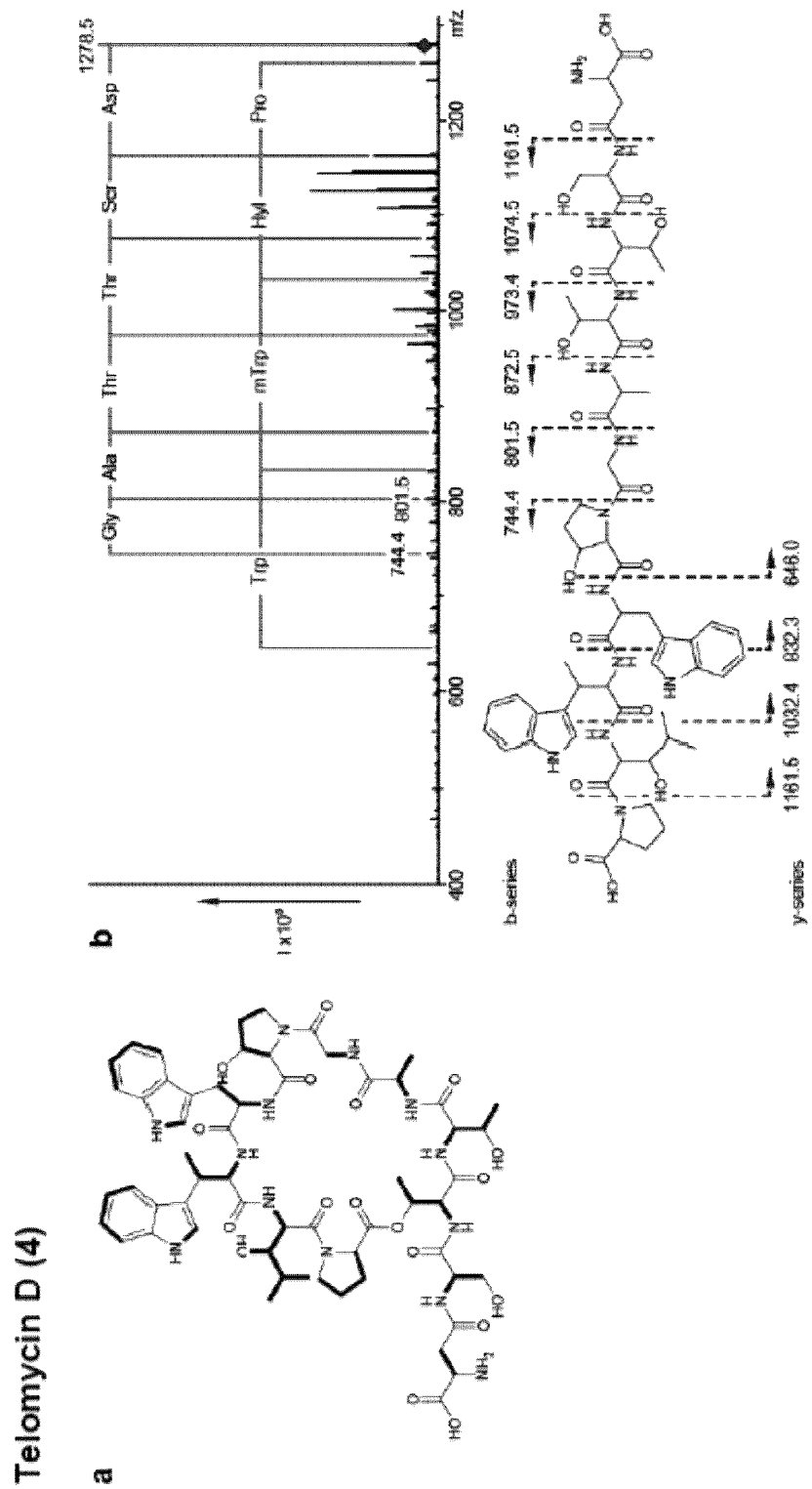
Figure 24:
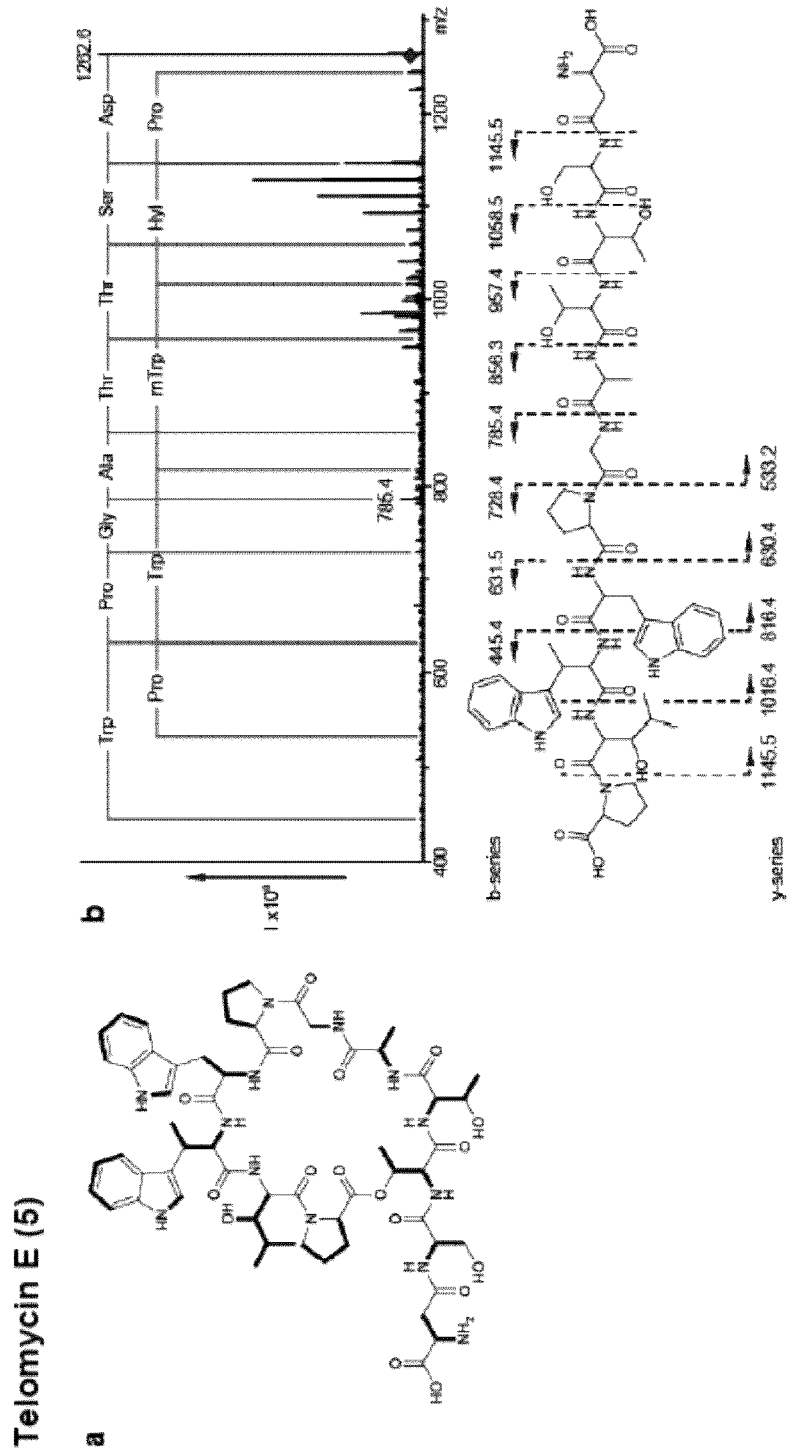
Figure 25:
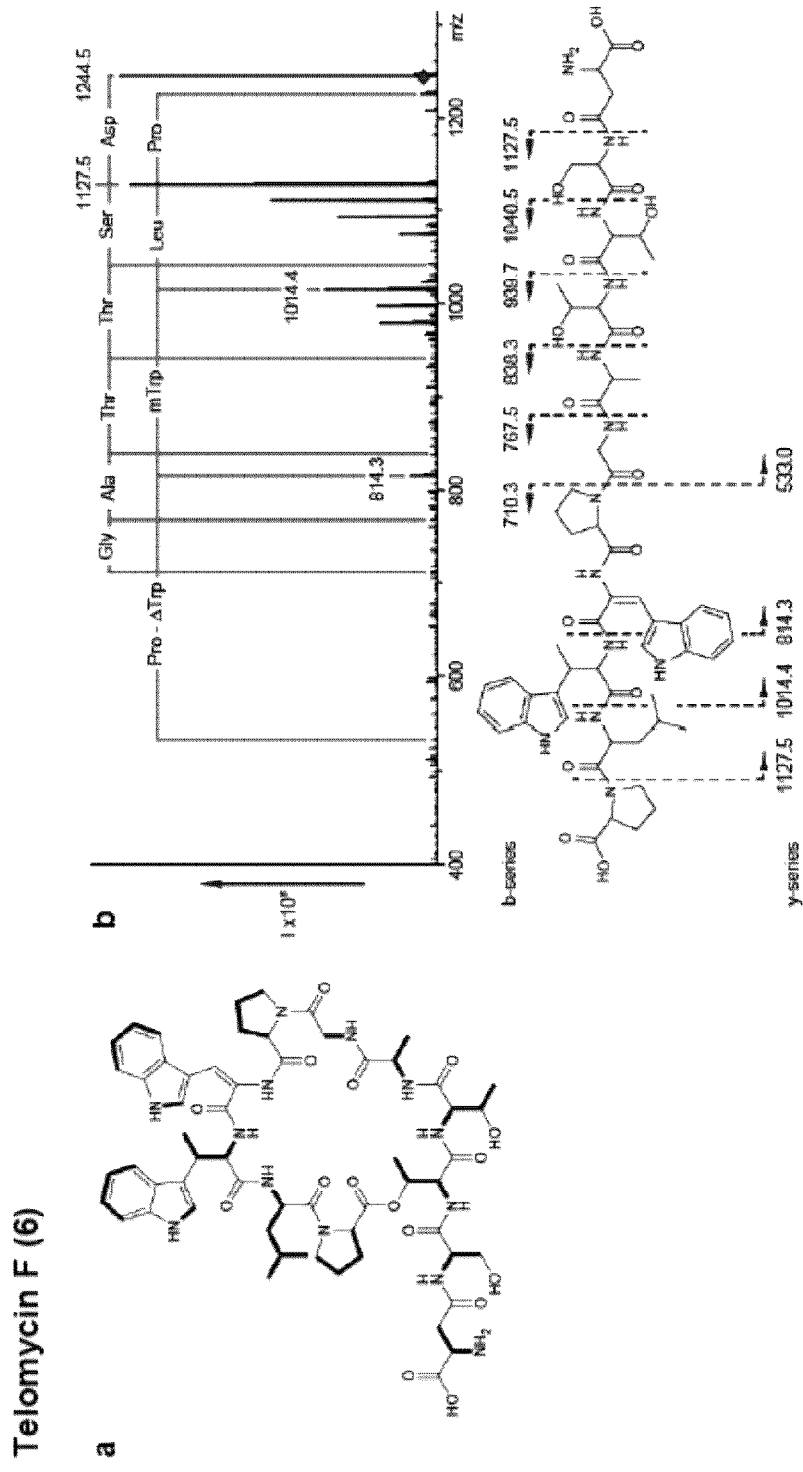
Figure 26:
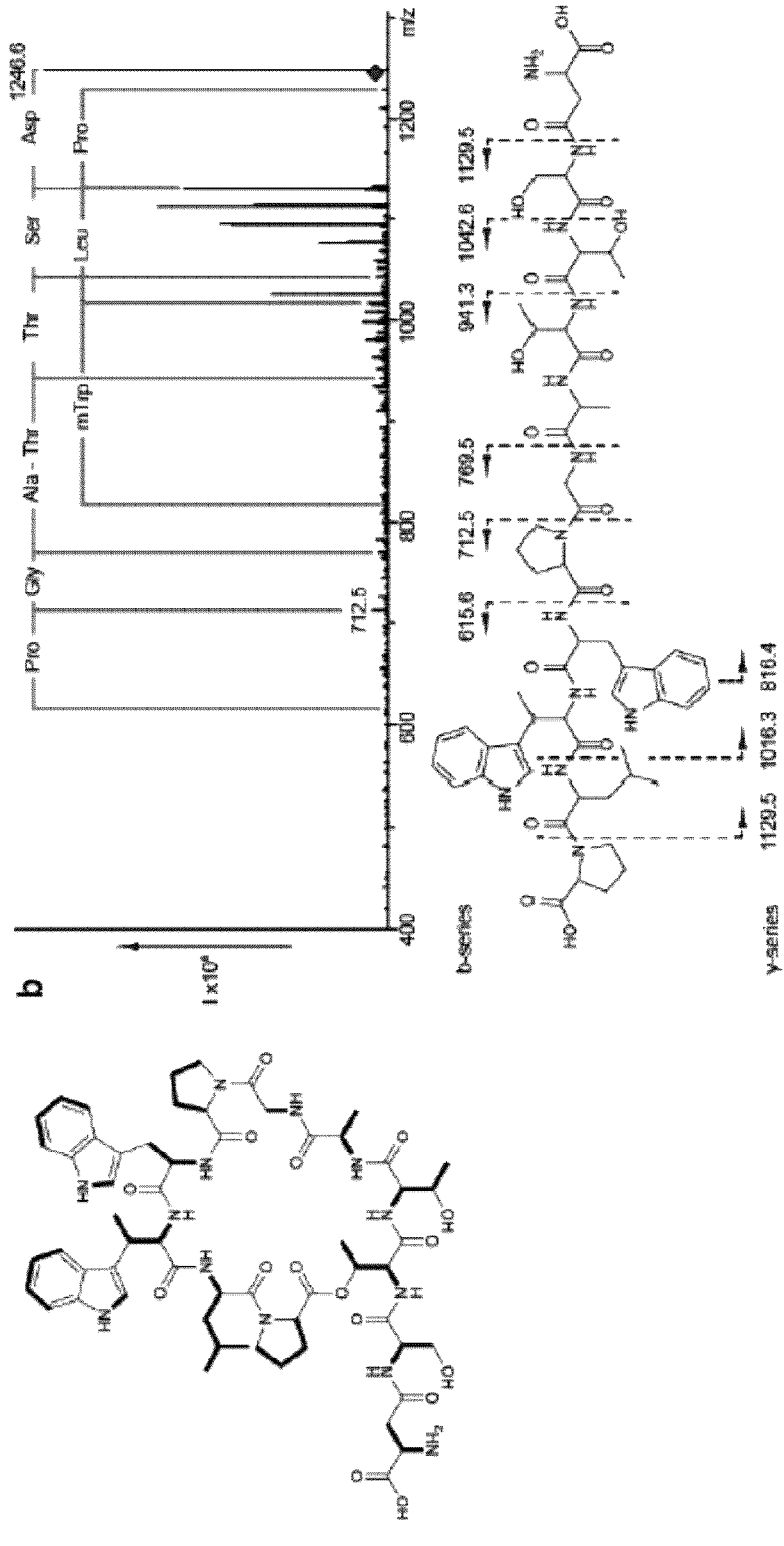
Figure 27:
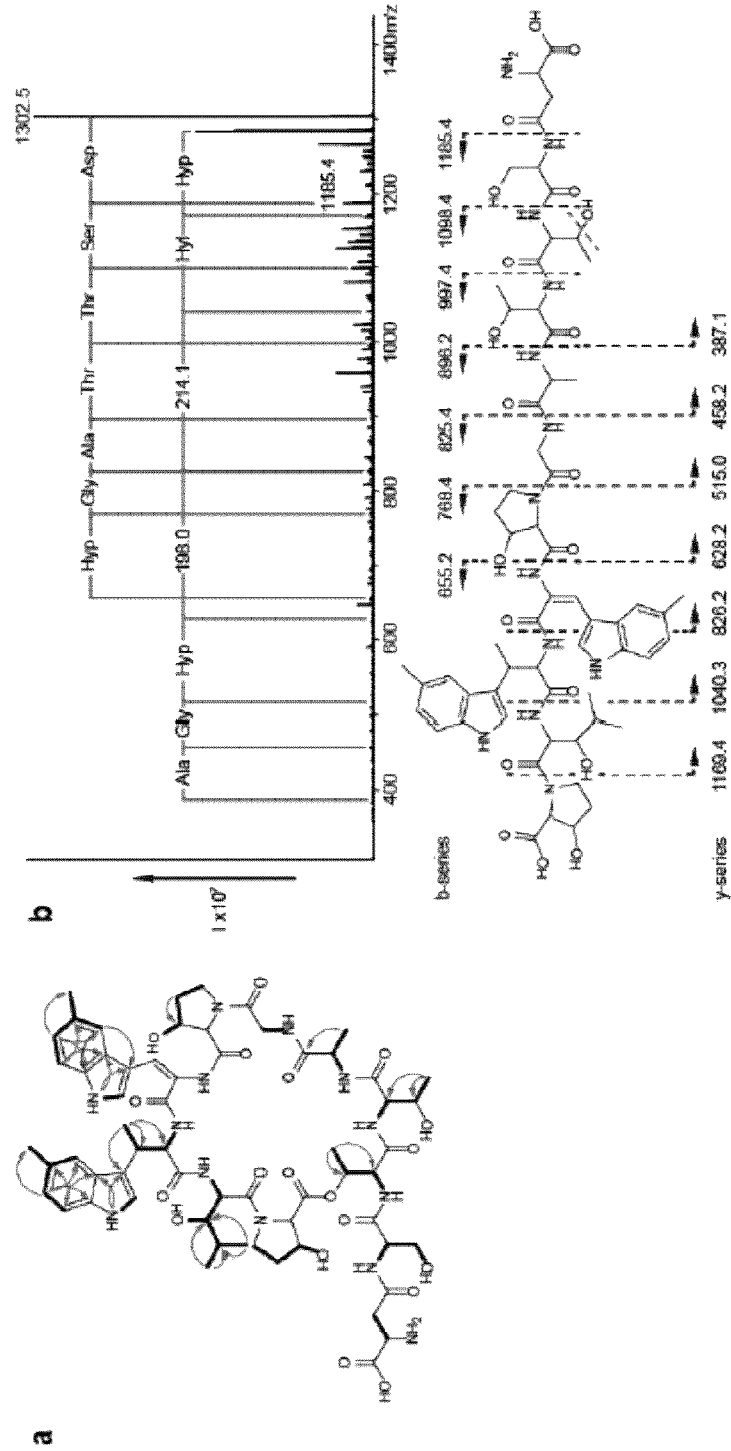
Figure 28:
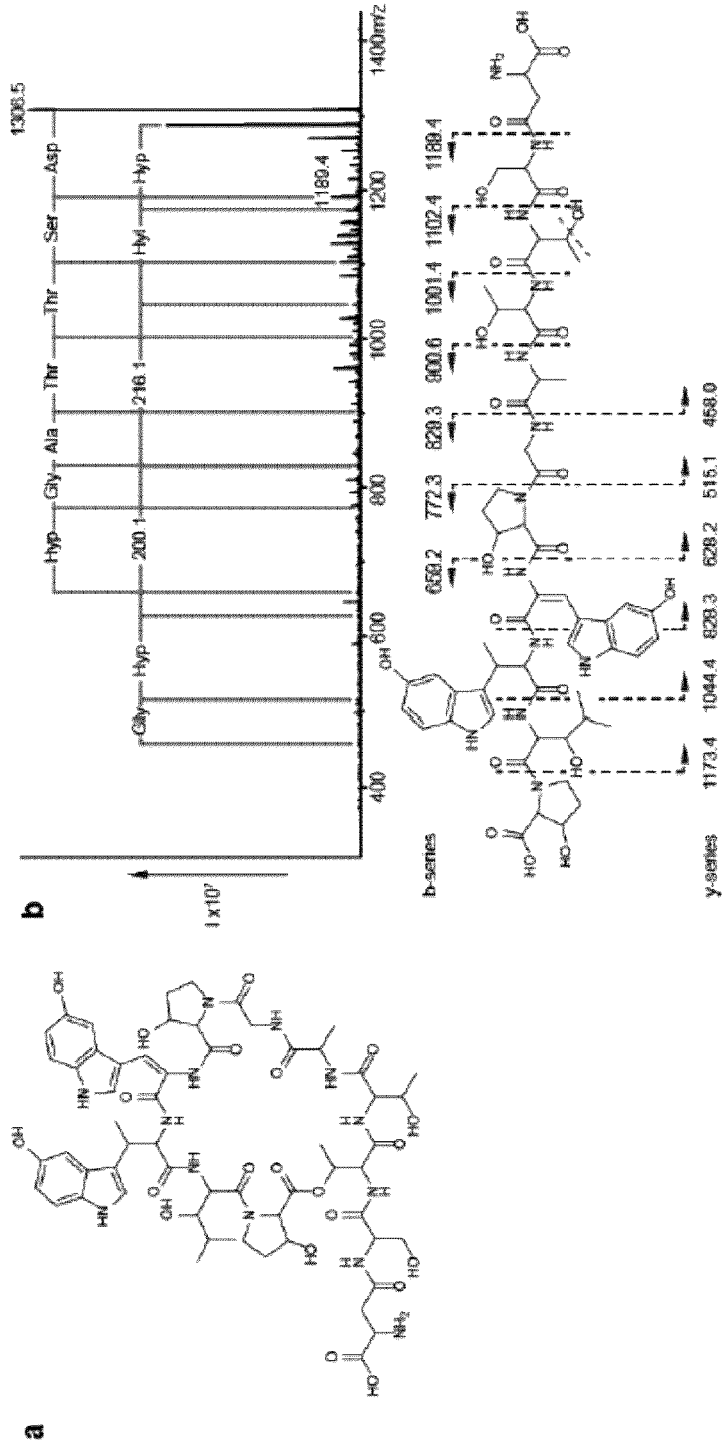
Figure 29:
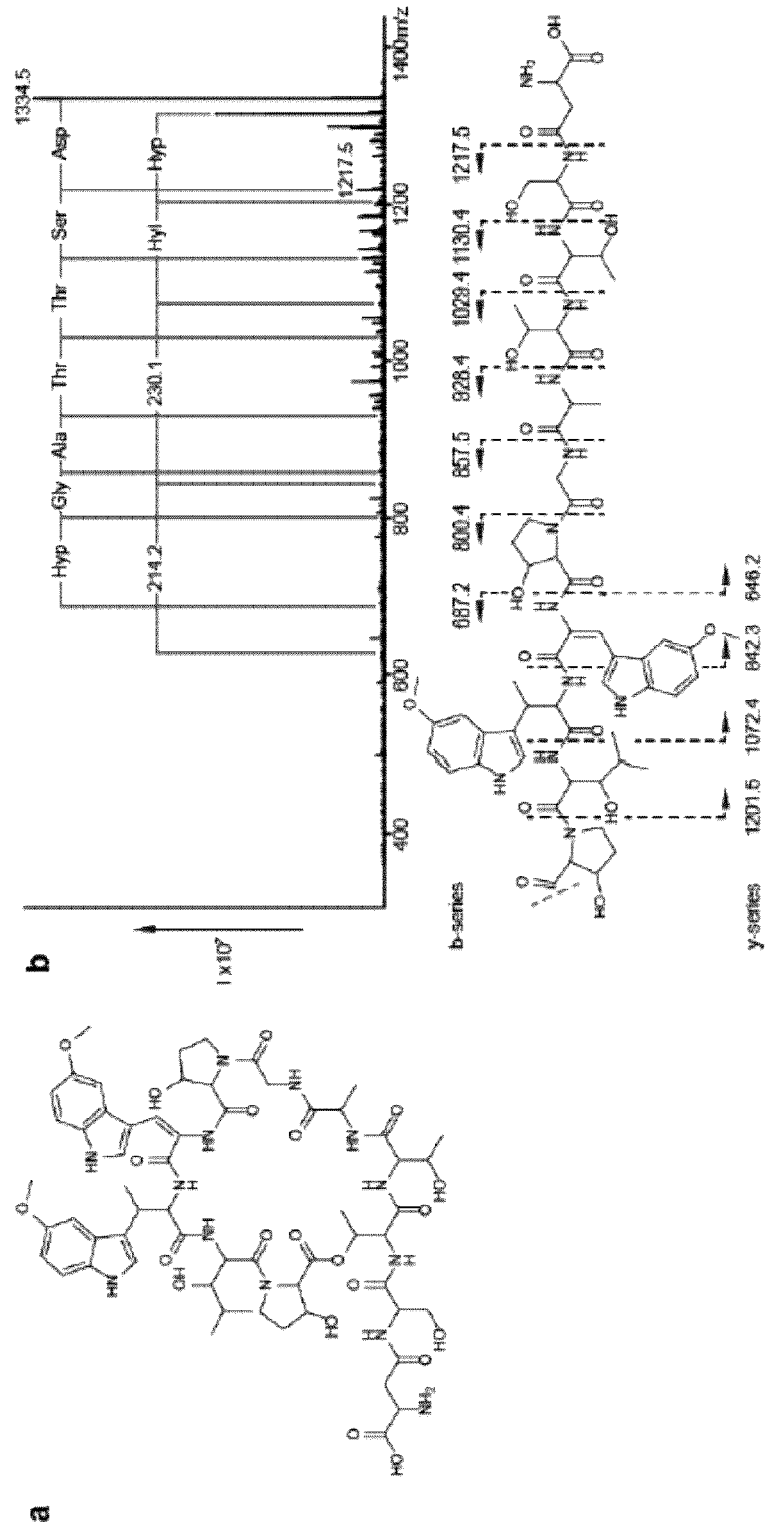
Figure 30:
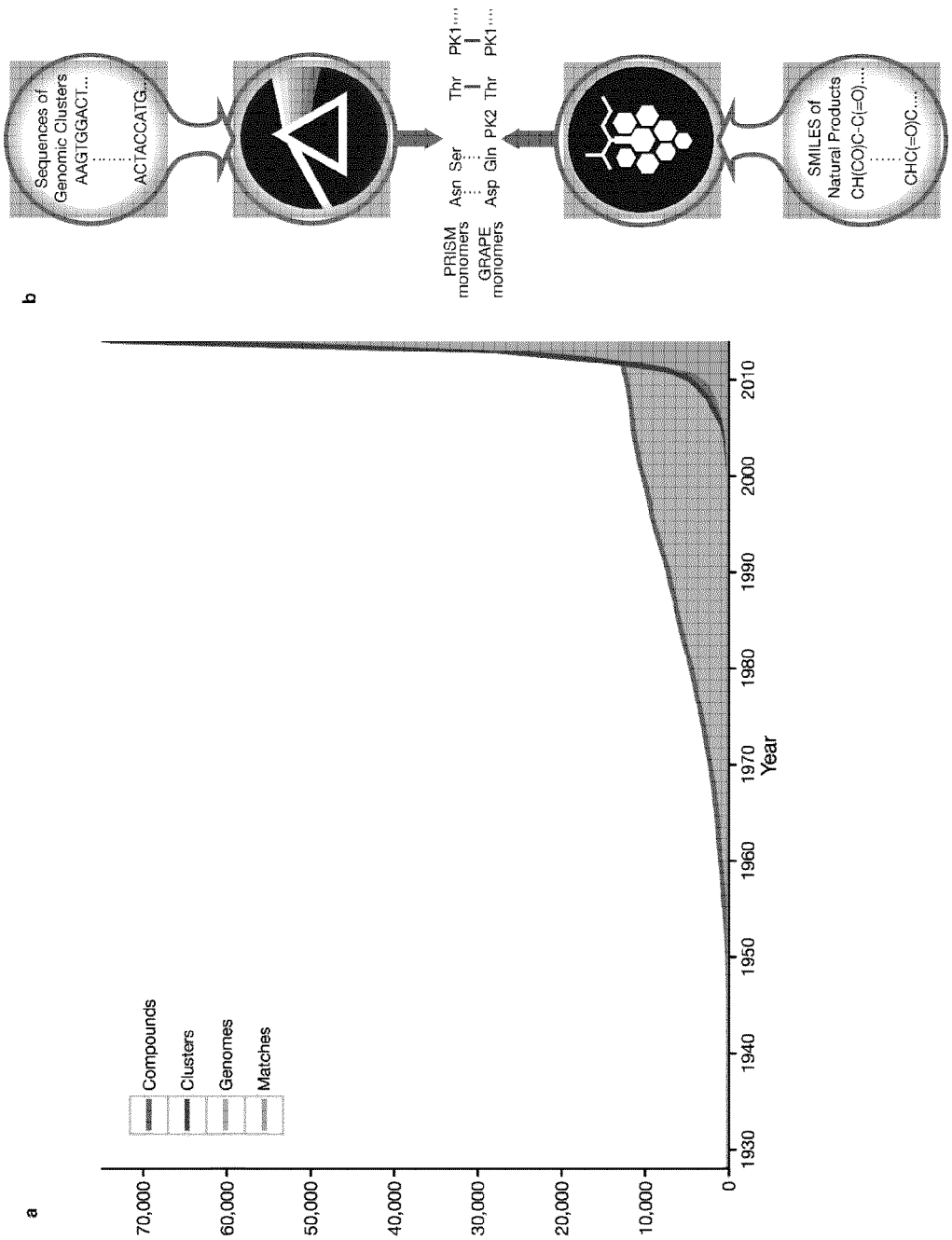
FIG. 30 shows a historical perspective of microbial polyketide and nonribosomal peptide natural products discovery and associated genetic information. (a) Comparison of natural products discovery with sequencing rates of gene clusters and genomes from 1990 to 2015. The compounds in red are microbial natural products that can be processed in GRAPE. The genetic sequences in yellow are nucleotide sequences that are over 100 kb from NCBI. In blue are the number of clusters identified via PRISM using all nucleotide sequences that are over 100 kb and are able to be processed in GRAPE. Matches in green are all known natural products with known biosynthetic clusters. (b) A pipeline created to match unknown gene clusters with known natural products: PRISM takes in genetic information to infer assembly line monomers and tailoring enzymes, while GRAPE takes small molecules to produce analogous information which can be compared.
Figure 31:
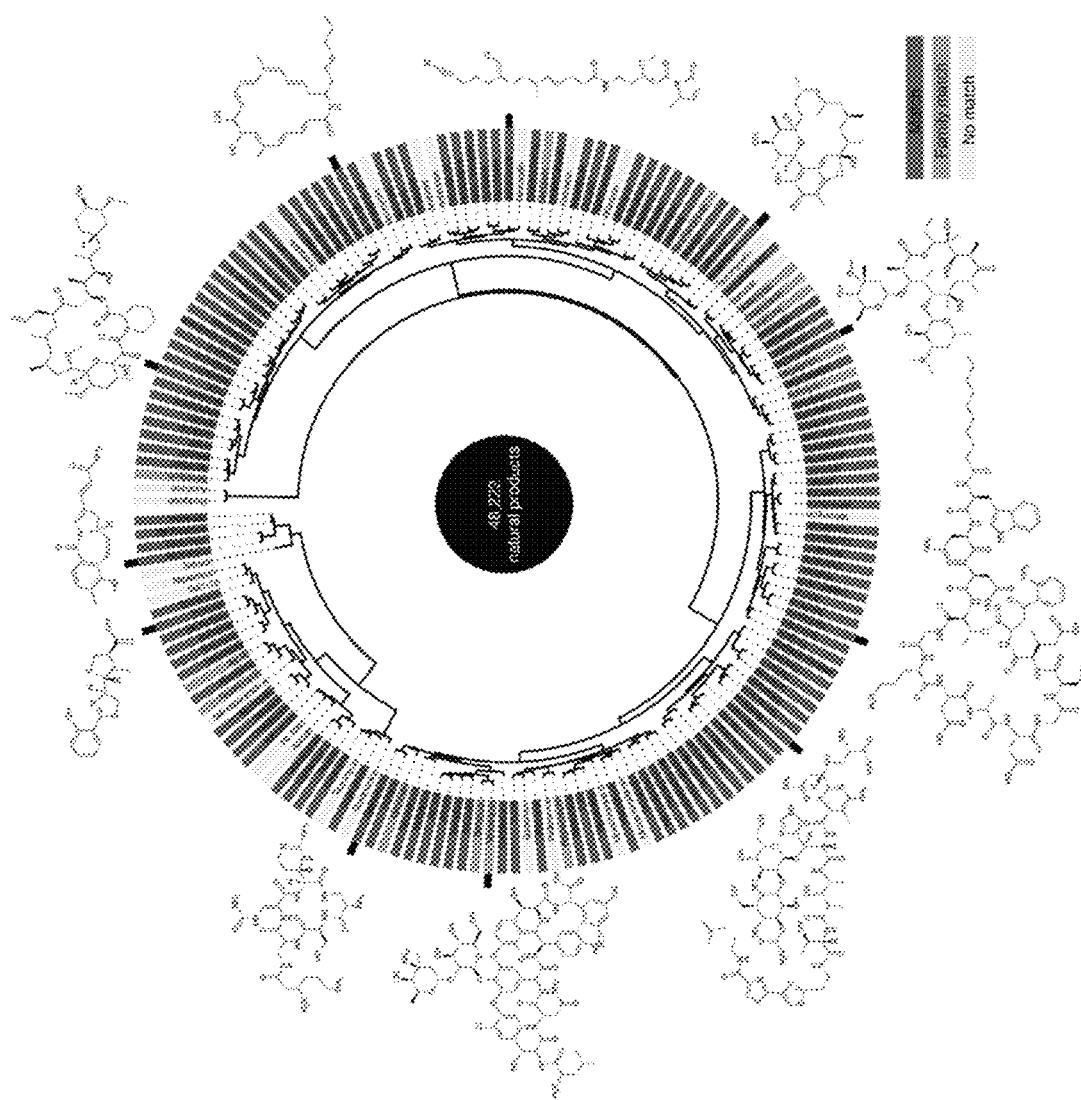
FIG. 31 shows the matching results of the test clusters (171 NRP, non-trans AT type 1 PK and hybrid PK/NRP) to in-house compound database (48,222 microbial natural products that can be processed via GRAPE).
Figure 32:
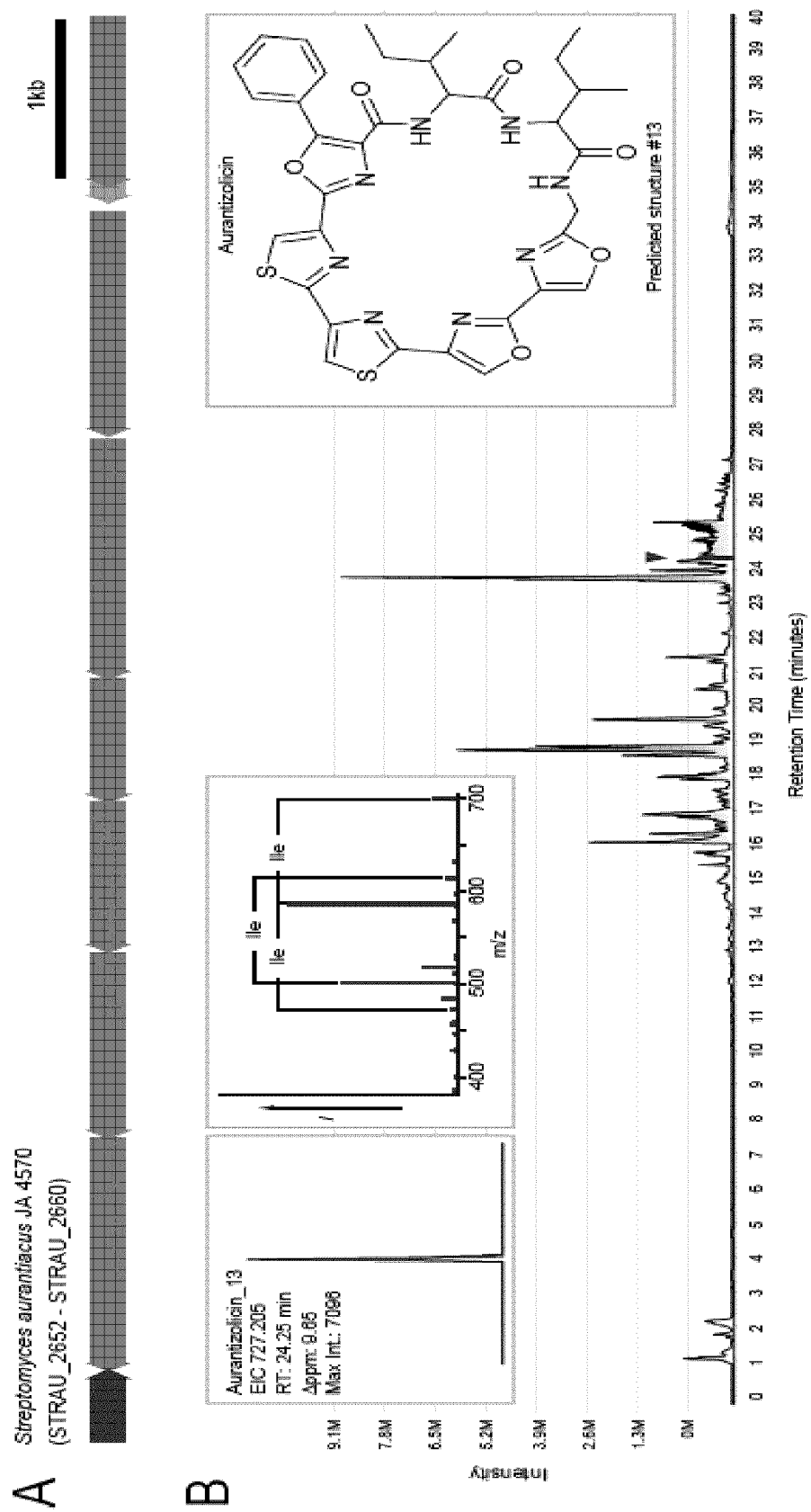
FIG. 32 shows a visualization of a gene cluster and natural product.

Telomycin is a lytic antibacterial agent, demonstrating rapid lysis of Gram positive bacteria including *S. aureus* and *B. subtilis* at concentrations above the minimum inhibitory concentration (MIC; FIG. 16B). Telomycin also does not display apparent cytotoxicity, as previous studies with Chinese Hamster ovary (CHO) cells did not observe toxicity at concentrations up to 40 μg mL$^{-1}$, and we did not observe cytotoxicity with human kidney (HEK293) cells at concentrations up to 128 μg mL$^{-1}$. Further, telomycin has demonstrated efficacy in animal studies without apparent toxicity and is not hemolytic (FIG. 18). To determine the mechanism of specific bacterial lysis, *S. aureus* and *B. subtilis* strains were exposed to telomycin to generate and select for spontaneous suppressor mutants which were sequenced to reveal candidate target loci. Telomycin-resistant bacteria generated with limited passaging were refractory to lysis (FIG. 19A) and demonstrated a 16-fold increase in MIC. Comparison of spontaneously resistant mutant genomes with those of their sensitive parent strains revealed a series of inactivating mutations in cardiolipin synthase (*S. aureus* cls2; *B. subtilis* clsA). Cardiolipin is a phospholipid dimer formed from the condensation of two phosphatidylglycerol monomers, found in the lipid membranes of bacteria and the inner membranes of mitochondria. As telomycin-resistant mutants possessed truncating- or missense mutations near the active site of cardiolipin synthase and were refractory to telomycin-mediated lysis, cardiolipin was investigated as a potential target. Resistant mutants possessed levels of cardiolipin ranging from 2 to 10% of wild type concentrations, with residual cardiolipin presumably produced by the remaining auxiliary cardiolipin synthase gene (*S. aureus* cls1; *B. subtilis* clsB). Cardiolipin levels are known to increase following growth in conditions of high salinity, and this was shown to correlate with improved telomycin activity. Having demonstrated that cardiolipin levels were strongly correlated with the antibacterial activity of telomycin, we sought to test whether telomycin specifically interacts with cardiolipin. In contrast to mixtures of telomycin with other lipids, telomycin and cardiolipin rapidly formed an opaque precipitant in a dose-dependent manner (FIG. 19B). This molecule-specific turbidity often occurs with peptide antibiotics that specifically bind membrane lipids, for instance cinnamycin binding to phosphatidylethanolamine, or lysocin binding bacterial menaquinone. Consistent with this observation and the hypothesis that telomycin exerts lytic activity through a specific interaction with cardiolipin, excess cardiolipin is able to completely abolish the antibacterial action of telomycin, in contrast to other bacterial phospholipids (FIG. 19C and FIG. 19D). This effect is dose-dependent (FIG. 19C) and is largely cardiolipin specific, although the monomeric cardiolipin analogue phosphatidylglycerol also demonstrates some protective effect when provided in 10× molar excess.

Cardiolipin possesses significant negative curvature relative to other phospholipids, which causes it to accumulate at poles and septa of bacterial cells. Although this has previously been established with microscopy, the only dye available to image cardiolipin is a simple derivative of acridine orange (10-N-nonyl acridine orange; NAO)—which was recently found to promiscuously stain anionic lipids in general, with limited selectivity for cardiolipin. Nevertheless, to investigate whether telomycin also localizes to these cardiolipin rich areas, we generated a fluorescein-labelled telomycin conjugate. Telomycin possesses a single free amine from the N-terminal aspartate residue, which is notably absent on the related molecule LL-AO341β and does not appear to impact activity. This amine was reacted with N-hydroxysuccinimide carboxyfluorescein to generate a fluorescent conjugate that demonstrated a slight decrease in antimicrobial activity. Imaging studies with live *B. subtilis* revealed that telomycin localizes to poles and septa (FIG. 19E) in a similar manner to the established cardiolipin dye NAO, albeit with less background signal from seemingly non-specific staining.

Although telomycin possesses a unique mechanism of action of and has demonstrated value in vivo, the emergence of spontaneous resistance could be problematic in a clinical setting. Interestingly, LL-AO341β demonstrates improved activity relative to telomycin, but lacks the N-terminal aspartate residue, as well as a hydroxylation on the C-terminal proline, suggesting that alterations to the telomycin scaffold or tailoring may improve activity. To assess the impacts of structural alterations on antibacterial activity, we isolated six telomycin congeners and elucidated their structures using HRMS, MS/MS sequencing, and 2D NMR experiments. The planar structures of telomycin B-G (2-7) were similar to the telomycin A scaffold, but demonstrated incomplete tailoring, including loss of the cis-3-hydroxyproline hydroxylation (B-G), of the trans-3-hydroxyproline hydroxylation (C, E-G), loss of the erythro-hydroxyleucine hydroxylation (F-G), and saturation of the double bond in $Z$-$\Delta_{2,3}$-tryptophan. Although $Z$-$\Delta_{2,3}$-tryptophan saturation negatively affected bioactivity, the successive loss of each hydroxylation improved it, indicating that general hydrophobicity and tryptophan orientation may be important in driving the interaction with membranes in general and cardiolipin in particular. To assess the role of tryptophan in initiating this interaction we generated additional telomycin A analogues through directed biosynthesis, incorporating methyl-, methoxyl-, or hydroxyl groups at indole position 5 in both tryptophan residues (FIGS. 19-29). Consistent with a role for the indole rings in embedding in the membrane and initiating an interaction, hydroxylation completely abolished telomycin activity, methoxy groups caused a modest decrease in activity, and methylation improved activity (FIG. 46). Importantly, telomycin F and di-5-methyltryptophan telomycin (8) possessed activity against resistant strains that was comparable with the activity of telomycin A against sensitive strains, suggesting that engineered variants with superior bioactivity can overcome potential resistance and take advantage of cardiolipin as a promising antibacterial target.

The chemical and mechanistic diversity of antibacterial natural products has provided privileged scaffolds for drug development along with chemical probes of cellular processes. Here, we systematically profiled antibiotic scaffolds, using a new algorithm to sort these natural products according to their biosynthetic building blocks. Using this approach we could accurately group these diverse chemical structures into families and subfamilies for downstream analysis. Identified subfamilies could be profiled with extant metadata and passed through our comprehensive resistance pipeline to enrich for rare chemical families with unknown mechanisms of action. As an example of this approach, telomycin was identified as an uncommon scaffold with a novel mechanism of action. Substrate and tailoring promiscuity is a hallmark of these modular antibiotic assembly lines and we leveraged this to produce improved telomycin analogues with superior activities against resistant isolates that were raised in the laboratory.

The selectivity of telomycin for cardiolipin is intriguing, as cardiolipin is a unique phospholipid dimer found in the membranes of nearly all bacteria and archaea. Telomycin is not hemolytic and is not known to possess significant toxicity to mammals and we define a lack of cytotoxicity at concentrations up to 128 μg mL$^{-1}$ in keeping with previous reports against cultured lines where cardiolipin is exclusively sequestered to the inner mitochondrial membrane. Unlike most other peptide antibiotics, it has been demonstrated that some members of the telomycin family of natural products may be orally-bioavailable.

Materials and Methods Used in Accordance with Example C

Cataloguing the Natural Antibiotic Collective

We compiled a comprehensive database of all known antibiotics isolated from microbial sources. The Handbook of Antibiotics[102] was supplemented by an exhaustive review of published antibiotic literature and patents. For each antibiotic, chemical structures were generated in SMILES format, and both the known or suspected mechanism of action of the compound and relevant toxicity data were also recorded. In total, 10,343 microbially produced antibiotics were identified. Of these, 3,159 were selective to bacteria, meaning they had no broad cytotoxicity or activity against eukaryotic cells or organisms. A number of computational and manual curation processes were performed in order to ensure the high quality data. When chemical structures of the same molecule within two different data sources differed, the molecule was manually inspected and its SMILES redrawn. Publicly available SMILES were observed to frequently represent tautomers of their natural products, so an algorithm was implemented to redraw enol and iminol tautomers of ester and amide bonds, respectively. Finally, SMILES representing salts of their corresponding natural products were redrawn in their non-charged states.

Development of a Retrobiosynthetic Similarity Scoring Algorithm for Natural Products In order to organize antibacterial natural products based on the biosynthetic history of these evolved small molecules, we developed a software package consisting of two algorithms. The first algorithm, termed GRAPE, performs in silico retrobiosynthesis of peptide, polyketide, and carbohydrate-containing compounds. GRAPE first cleaves defined biosynthetic bonds (chemical bridges [disulfide bonds, aromatic ethers, etc], heterocycles, core bonds [esters, amides, lactones, etc.], and tailoring modifications [glycosylation, methylation, sulfation, etc.]), then attempts to match remaining monomers with a comprehensive library of known biosynthetic units (amino acids, carbohydrates, etc.). Remaining units are parsed through a polyketide retrobiosynthetic module which scans the carbon backbone and assesses likelihood of polyketide origin, and predicts the architecture of the parent polyketide synthase (PKS). This collection of ordered monomers for each natural product deconstructed by GRAPE is then passed to a second algorithm for pairwise analysis based on order and composition. The second algorithm, termed GARLIC, aligns units of biosynthetic information identified by the retrobiosynthetic algorithm (i.e., proteinogenic and non-proteinogenic amino acids, ketide units, sugars, halogens, nonribosomal peptide and polyketide starter moieties, and selected tailoring modifications) to all molecules within the database of targeted antibiotics using a modified Needleman-Wunsch algorithm. GRAPE and GARLIC implement chemical abstractions developed by the Chemistry Development Kit, version 1.4.19.

Generation of the Antibacterial Tree

A subset of our antibacterial small molecule collection, consisting of 2,026 targeted antibiotics, was retrobiosynthetically decomposed using GRAPE, and the decomposed natural products were aligned to one another using GARLIC. The similarity matrices generated by GARLIC alignments of biosynthetic information were converted to dissimilarity matrices. The generated dissimilarity matrices were used to hierarchically cluster the antibiotics using the hclust function within the stats R package. A tree was generated with the ape R package. The tree was visualized and clades were collapsed in Dendroscope based on observed families of natural products.

Development of a Database of Hidden Markov Models for Antibiotic Resistance Genes In order to identify resistance determinants within biosynthetic gene clusters, we compiled a comprehensive database of 257 profile hidden Markov models for genes associated with antimicrobial resistance. 166 hidden Markov models were obtained from the Resfams antibiotic resistance profile hidden Markov model database. A single model (PFAM12847, a generic methyltransferase model) was removed as it was observed not to be specific to antibiotic resistance. The Resfams database was supplemented by the development of an additional 91 profile hidden Markov models associated with antibiotic resistance. Sequences were manually collected based on homology to experimentally annotated sequences, aligned using MUSCLE, and trimmed using trimAI to remove gaps present in fewer than 50% of sequences. Hidden Markov models were generated from the resulting alignments using the hmmbuild program, version 3.1b1, from the HMMER3 software package. Bitscore cutoffs for each hidden Markov model were determined by manual analysis of the results of a search of the UniProtKB database (UniProt Knowledgebase for the collection of function information on proteins), using the HMMER web server.

General Chemical Procedures Used in Accordance with Example C 1D ($^1$H and $^{13}$C) and 2D ($^1$H-$^{13}$C HMBC, HSQC, $^1$H-$^1$H NOESY, TOCSY, and COSY) NMR spectra for telomycins were recorded on a Bruker AVIII 700 MHz NMR spectrometer in $d_6$-DMSO (Sigma Aldrich). High-resolution MS spectra were collected on a Thermo LTQ OrbiTrap XL mass spectrometer (ThermoFisher Scientific) with an electrospray ionization source (ESI) and using CID with helium for fragmentation. LCMS data was collected using a Bruker AmazonX ion trap mass spectrometer coupled with a Dionex UltiMate 3000 HPLC system, using a Luna C18 column (150 mm×4.6 mm, Phenomenex) for analytical separations, running acetonitrile with 0.1% formic acid and ddH$_2$O with 0.1% formic acid as the mobile phase.

Microbial Strains and Telomycin Production

Streptomyces canus was purchased from the American Type Culture Collection (ATCC, ATCC no. 12647). S. canus was maintained on Bennett's agar at 28° C. S. aureus Newman was maintained on cation adjusted Mueller Hinton broth (CAMHB) agar at 37° C. B. subtilis 168 was maintained on CAMHB agar at 28° C.

Fresh colonies of Streptomyces canus were used to inoculate 50 mL cultures of GYM media containing 0.5% glycine (GGYM), and then grown for 72 h at 28° C. and 250 rpm. 10 mL of starter culture was used to inoculate 500 mL of the same media, followed by growth for 72 h at 28° C. and 250 rpm. Cultures were harvested by centrifugation, followed by a methanol extraction of the pellet and extraction of the supernatant with 2% absorbent HP-20 resin (Diaion). Resins were eluted with excess methanol, and the eluent was pooled with the pellet methanol extract and evaporated to dryness. The extract was resuspended in a small volume of methanol and separated on an open gravity column of LH-20 size exclusion resin (Sephadex) with methanol as a mobile phase. Fractions containing telomycin were pooled, evaporated to dryness, and resuspended in methanol. Telomycin was isolated by preparative scale LC-MS using a Luna 5 μm C$_{18}$ column (250×15 mm, Phenomenex) with water (0.1% formic acid) and acetonitrile (0.1% formic acid) as the mobile phase, at a flow rate of 10 mL/min. After 4 min, acetonitrile was increased in a linear manner (curve 5) from 5% to 30% at 14 min, then increased 31% by 20 min, then to 40% by 40 min, followed by a wash of 100% methanol. Telomycins eluted at the following retention times: A—26 min, B—28 min, C—31.5 min, D—32.5 min, E—34 min, F—35 min, G—38 min.

Directed Biosynthesis of New Telomycins

Fresh colonies of Streptomyces canus were used to inoculate 50 mL cultures of GYM media containing 0.5% glycine (GGYM), and then grown at 28° C. and 250 rpm. After 24 h, non-natural amino acids were added by sterile syringe filtration, to a final concentration of 4 mM. Cultures were grown for an additional 48 h and harvested, following the same isolation and purification procedure of natural telomycins. Unnatural amino acids were purchased from Sigma Aldrich. Individual analogue retention times were recorded and candidate peaks selected for purification and testing. Chemical structures were assigned using NMR and high-resolution mass spectrometry Determination of Antibacterial Activity Minimum inhibitory concentrations (MICs) for telomycins were determined using broth microdilution in cation-adjusted Mueller Hinton broth (CAMHB). Bacillus subtilis strains were cultured at 28° C., and S. aureus strains were cultured at 37° C. The MIC was determined as the lowest concentration of drug at which no growth was observed after 16 h. For assessing the impact of treating strains with sodium chloride concentrations prior to telomycin, S. aureus was grown overnight in CAMHB containing 0, 0.5, 1, or 1.5 M NaCl and then MICs were recorded as described above. Broth microdilution assays were performed in fresh media with identical NaCl concentrations and again MIC was determined as the lowest concentration of drug at which no growth was observed after 16 h.

Measuring Turbidity of Telomycin-Lipid Mixtures

To measure the turbidity of telomycin-lipid mixtures, telomycin was dissolved in methanol at a concentration of 12.8 mg/mL, and cardiolipin (Sigma Aldrich; C0563; 98% pure), phosphatidylglycerol (Sigma Aldrich; 63371; ≥98% pure), phosphatidylcholine (Sigma Aldrich; P3556; ≥99% pure), and phosphatidylethanolamine (Sigma Aldrich; P7943; 97% pure) were dissolved in methanol at a concentration of 10 mg/mL. 20 μL of telomycin was mixed with 20, 10, 5, 1, or 0.5 μL of each lipid (final reaction volume 40 μL) in a flat-bottom polystyrene 96-well plate. Optical density (OD=600 nm) was measured after 10 min.

Colony Forming Unit (CFU) Assays

Cultures of S. aureus and B. subtilis were grown overnight in CAMHB. Starter cultures were used to inoculate fresh media and were grown to OD=0.2, after which they were transferred to 96-well plates. Cultures were serially diluted and plated on CAMHB agar to determine initial colony-forming units. Telomycin dissolved in DMSO was added to each well (1:100) and incubated for 90 min, followed by serial dilution and plating to determine colony-forming units. Results are shown as ±s.d.; n=4; Two-tailed students t-test.

Red Blood Cell (RBC) Hemolysis Assay

Hemolytic activity of telomycin was measured against a 0.25% sheep red blood cell (RBC, Fisher Scientific) suspension in phosphate-buffered saline. Telomycin was serially diluted from 256 to 2 μg/mL and incubated with the RBC suspension for 1 h at 37° C. in a polypropylene 96-well plate with conical wells. After 1 h, RBCs were pelleted (1000×g for 5 min) and the supernatant was transferred to a flat-bottom polystyrene 96-well plate, measuring absorbance at 540 nm. 1% Triton X-100 was used as a positive control, while DMSO alone and RBCs alone were used as negative controls.

Measuring Bioactivity of Telomycin-Lipid Mixtures

To assess the impact of various lipids on telomycin's antibacterial activity on solid agar, 10 μL of 10 mM telomycin was mixed with 10 μL of 20 mM cardiolipin (Sigma Aldrich; C0563; ≥98% pure), phosphatidylglycerol (Sigma Aldrich; 63371; ≥98% pure), phosphatidylcholine (Sigma Aldrich; P3556; ≥99% pure), or phosphatidylethanolamine (Sigma Aldrich; P7943; ≥97% pure). All compounds were dissolved in methanol. Mixtures were incubated for 10 min, then added to diffusion disks, allowed to dry, then placed on a CAMHB agar plate with B. subtilis as an indicator organism. The plate was incubated overnight at 28° C.

To assess the impact of various lipids on telomycin's antibacterial activity in liquid media, telomycin was dissolved in methanol at 12.8 mg/mL (approx. 10 mM) and 1 μL was added to a 96-well plate. Lipids were dissolved in methanol and 10 μL of 10, 5, 2, 1, or 0.5 mM lipid was added to each telomycin-containing well. CAMHB inoculated with B. subtilis was added to each well and serially diluted to determine the minimum inhibitory concentration of each telomycin-lipid mixture. Plates were incubated shaking at 28° C. for 16 h.

Preparation of N-Fluorescein Labelled Telomycin

To generated a telomycin-fluorescein conjugate, 2.5 mg of telomycin A was dissolved in 200 μL DMSO and mixed with 10 mg 5(6)-carboxyfluorescein N-hydroxysuccinimide ester (Sigma Aldrich) dissolved in 180 μL DMSO, and 20 μL 0.5 M sodium bicarbonate. The reaction was allowed to proceed overnight at room temperature, after which the reaction was quenched by the addition of formic acid and N-labelled telomycin was purified by preparative scale LC-MS.

Measuring Cardiolipin Content of Bacterial Cells

Cardiolipin was extracted using an acidic Bligh Dyer method. A 50 mL culture of bacteria grown for 24 h was pelleted and resuspended in 1 mL 0.1 N HCl. 2.5 mL of methanol and 1.25 mL of chloroform was added to each sample, followed by 30 min incubation at room temperature. After this, 1.25 mL of 0.1 N HCl and 1.25 mL of chloroform was added to create a two-phase solution that was then centrifuged at 3000×g for 10 min. The bottom phase was recovered, evaporated to dryness, and then resuspended in methanol. An established LC-MS method was used to quantify cardiolipin content, using a reverse-phase Luna C18 column (150 mm×4.6 mm, Phenomenex). The mobile phases were A (90% acetonitrile, 10% water, 0.5% glacial acetic acid, 0.5% triethylamine) and B (90% isopropanol, 10% water, 0.5% glacial acetic acid, 0.5% triethylamine), running at 0.8 mL/min. After 3 min, solvent B was increased from 50% to 100% by 22 min, then held for 15 min, before returning to 50% by 38 min. Cardiolipin species eluted between 27 and 32 min. Relative cardiolipin content was assessed by summing the areas associated with cardiolipin species ions in simultaneously and identically extracted wild type and mutant bacteria, presenting percentage of cardiolipin signal detected in the mutant strain, relative to wild type.

Genome Sequencing and Analysis of Antibiotic Biosynthetic Gene Clusters

A single colony of Streptomyces canus (ATCC 12647) was used to inoculate a 50 mL culture of GYM media containing 0.5% glycine (GGYM), and then grown for 96 h at 30° C. and 250 rpm. 500 μL of culture was centrifuged at 12×g for 5 min and resuspended in 500 μL SET buffer (75 mM NaCl, 25 mM EDTA pH 8.0, 20 mM Tris HCl pH 7.5, 2 mg/mL lysozyme) to lyse for 2 h at 37° C. Proteinase K and SDS were added after lysis to final concentrations of 0.5 mg/mL and 1%, respectively. Lysis mixtures were incubated at 55° C. for 2 h before adjusting the concentration of NaCl to 1.25 M and extracting twice with phenol-chloroform. Isopropanol was added (equivalent to 60% the volume of the solution) to precipitate genomic DNA, which was subsequently washed twice with 70% ethanol and resuspended in sterile water for sequencing. For sequencing Staphylococcus aureus and Bacillus subtilis strains, single colonies were used to inoculate 3 mL overnight cultures in tryptic soy broth (TSB), incubated a 37° C. and 30° C. respectively. Genomic DNA was isolated using a GenElute Genomic DNA Extraction kit (Sigma Alrich). Genomic DNA for all strains was sent for library preparation and Illumina sequencing at the Farncombe Metagenomics Facility at McMaster University, using an Illumina HiSeq DNA sequencer. Contigs were assembled using the ABySS genome assembly program and with Geneious bioinformatic software.

Identification of Telomycin-Resistance Mutations in Sequenced Isolate Genomes

To identify mutations that conferred resistance to telomycin, we isolated colonies of S. aureus Newman that appeared inside the zone of inhibition observed during telomycin disk diffusion assays. Colonies were cultured overnight in TSB containing 50 μg/mL telomycin (~5×MIC), then used to inoculate a 96-well plates containing a serial dilution of telomycin, up to 128 μg/mL. Genomic DNA was extracted from highly resistant isolates and their sensitive parental strain, and sequenced with an Illumina MiSeq platform. Sequences were compared using BreSeq, which exclusively identified mutations in the predominant, house-keeping cardiolipin synthase (cls2). Bacillus subtilis telomycin-resistant mutants were identified in a similar manner, and mutations in cardiolipin synthase were confirmed by sequencing PCR products of the two cardiolipin synthase genes: clsA and clsB. A point mutation was observed next to the second HKD motif active site in clsA, which resulted in a 90% decrease in cardiolipin levels. PCR primers used for the amplification of B. subtilis cardiolipin synthase genes are as follows— clsAF: 5'-GTTTTAAAGAAATCTGCCCG-3' (SEQ ID NO: 1);

clsAR: 5'-GCGAGACGGATTCTTTTATT-3' (SEQ ID NO: 2);

clsBF: 5'-ATGAAGGTATTTATCGTGAT-3' (SEQ ID NO: 3);

clsBR: 5'-TTATAAGAAATAAGATAATG-3' (SEQ ID NO: 4).

Structure Elucidation

The structure of telomycin A was confirmed by a series of 1D and 2D NMR spectroscopy experiments, high resolution mass measurement, and MS/MS fragmentation and annotation. Structures of new naturally occurring variants were elucidated by MS/MS fragmentation and annotation, high resolution mass measurements, and comparison of 1D and 2D NMR experiments to those of telomycin A. Structures of telomycins generated by directed biosynthesis were confirmed by MS/MS fragmentation and annotation, and high resolution mass measurements. The structure of di-5-methyltryptophan telomycin was also confirmed by 10 and 2D NMR experiments.

Cytotoxicity Assay

HEK293 cells were obtained from the American Type Culture Collection (ATCC; ATCC CRL-1573) and maintained in Minimal Essential Media (MEM) Alpha modifications supplemented with 10% fetal bovine serum. Cellular identity was confirmed by Cells were cultured in 96-well plates containing 200 µL of media and 5000 cells per well. After 3 h of incubation, cells were treated with a serial dilution of telomycin A. Experiments were performed in duplicate with DMSO as a negative control and mitomycin C as a positive control. After 48 h incubation, 10% (22 µL) Alamar Blue (Life Technologies) was added and incubated with cells for 4 h at 37° C. Fluorescence was measured at an excitation wavelength of 530 nm and an emission wavelength of 590 nm and compared to a no-drug control.

Fluorescence Microscopy

A stationary phase culture of Bacillus subtilis 168 was washed twice in LB medium to remove extracellular debris, centrifuging at 10,000 rpm for 1 min each wash. Both N-carboxyfluorescein telomycin and 10-N-nonyl acridine orange (NAO) were added to cells to compare probe localization. N-carboxyfluorescein telomycin was added to a final concentration of about 1 µM, and NAO was added at a final concentration of 0.5 µM. Both probes were incorporated for 20 min in the dark. The suspensions were washed again to remove extracellular probe, then added to a poly-L-lysine coated 0.17 µm glass bottom microplate (Brooks Automation). To these samples, the membrane dye FM 4-64 was added to a final concentration of 1 µg/mL. Cells were imaged using a Nikon Eclipse Ti inverted microscope at 1000× magnification with a Nikon Plan Apo λ 100× oil-immersion objective. Overlays were prepared using the Nikon Elements software suite. Profile plots were prepared in ImageJ[134] by cropping regions of interest, and converting to 8-bit greyscale images. No background subtractions were made, and the grey values across the length of a cell were plotted for FM 4-64, N-carboxyfluorescein telomycin, and overlay, to highlight probe localization.

Statistical Analysis

Significance of CFU assays were calculated with two-tailed student T-tests, using Excel 2013 (Microsoft). All CFU experiments were performed at least twice in the laboratory, with four replicates (n=4) for each condition.

Example 1

Microbial Natural Products with Specific Antibacterial Activity Define a Diverse Range of Antibacterial Targets A comprehensive review of the antibacterial natural products identified 54 distinct molecular targets of known antibacterials, including membrane components and membrane-bound enzymes (1-14), cell wall associated enzymes (15-18), amino acid biosynthesis and metabolism (19-38), fatty acid biosynthesis (39-44), individual metabolic enzymes (45-47), and macromolecular machineries (48-54) such as the ribosome (50) or RNA polymerase (52).

Example 2

A Retrobiosynthetic Strategy for Charting Antibacterial Natural Products and Identifying Rare Scaffolds with New Molecular Targets a) A retrobiosynthetic algorithm was devised to deconstruct antibiotics according to their modular biosynthetic origins and facilitate high fidelity clustering of related families. Products of modular assembly architectures are broken down with class-specific rules, providing biosynthetic monomers that can be aligned and scored using a similarity matrix that can be used for hierarchical molecular clustering. (b) A sampled collection of antibacterials, including 1,908 modular natural products with specific antibacterial activity. Families are colored by known or unknown mechanism of action, and natural product chemotypes are highlighted by color (outer ring). A section of the peptide antibiotics is inset, demonstrating distinct branches for a number of antibacterial peptide subfamilies. (c) Schematic for PRISM-based HMM resistance network screening, outlining the automated detection of biosynthetic gene clusters and detection of known resistance determinants guiding focus towards gene clusters with potentially novel mechanisms of action.

Example 3

Telomycin—a Nonribosomal Peptide that Lyses Bacteria Through an Unknown Mechanism (a) Structure of telomycin. (b) Telomycin lyses S. aureus at high concentrations. Wild type S. aureus (OD 0.2) was exposed to 8 (1×MIC) or 256 µg ml$^{-1}$ (32×MIC) telomycin. Colony-forming units (CFUs) were taken before treatment (black) and after 90 min (white). Results are shown as ±s.d.; n=4; Two-tailed students t-test. P=0.0023. Data are representative of three independent experiments.

Example 4

PRISM Results for the Telomycin Biosynthetic Gene Cluster (a) Detection of the telomycin biosynthetic gene cluster. Red indicates nonribosomal peptide synthetase genes, brown indicates resistance genes, green indicates tailoring enzymes, and gray represents other biosynthetic enzymes. (b) Detection of a generic ABC transporter as the sole known resistance determinant detected in the telomycin gene cluster.

Example 5

Telomycin does not Cause Hemolysis

A solution of 0.25% sheep red blood cell suspension in phosphate buffered saline was incubated for 1 h at 37° C. with either a serial dilution of telomycin, 1% Triton X100 (positive lysis control), DMSO alone (1%; negative lysis control), or without added content (negative lysis control). After 1 h RBCs were pelleted and lysis was assessed by measuring absorbance of the supernatant at 540 nm.

Example 6

Telomycin Exerts Bactericidal Activity by Interacting with Cardiolipin (a) Mutating cardiolipin synthase provides spontaneous telomycin resistance. Wild type and spontaneously-resistant S. aureus (left) and B. subtilis (right) were exposed to 32×MIC concentrations of telomycin for 90 min. CFUs were taken before treatment (black) and after 90 min (white). Results are shown as ±s.d.; n=4; Two-tailed students t-test. P=0.0018. Data are representative of three independent experiments. (b) Telomycin-cardiolipin mixtures uniquely and rapidly acquire turbidity. Telomycin (final concentration 5 mM; 6.3 mg ml$^{-1}$) was mixed with CL, PG, PE, or PC at concentrations ranging from 0.125 to 5 mg ml$^{-1}$. Mixtures were incubated for 5 min before turbidity was measured using absorbance at 600 nm. (c) Cardiolipin reduces telomycin's antibacterial activity in a dose-dependent manner. Telomycin (0.1 mM) was exposed to lipids at concentrations ranging from 1 to 0.05 mM, then used to determine MICs against wild type *B. subtilis*. Identical results were observed for PE and PC (gray). (d) Cardiolipin abolishes telomycin's antibacterial activity. Telomycin (10 mM; I) was mixed with 2× molar equivalent of CL (II), PG (III), PE (IV), or PC (V). Mixtures were added to diffusion disks using *B. subtilis* as an indicator organism and grown overnight. (e) One-day cultures of *B. subtilis* were labelled with the membrane dye FM4-64 (left) and a fluorescent conjugate of telomycin (middle). Telomycin accumulated at poles and septa. Summed pixel intensities of a selected bacteria are depicted below. Scale bar, 5 μm.

Example 7

Structure Confirmation of Telomycin A (1)

(a) Structure of telomycin A confirmed by NMR spectroscopy, HRMS, and MS/MS fragmentation. (b) Annotated MS2 spectra of base-hydrolyzed telomycin A, including observed b- and y-ions resulting from amide bond cleavage.

Example 8

Structure Elucidation of Telomycin B (2)

(a) Structure of telomycin B elucidated by comparative NMR spectroscopy, HRMS, and MS/MS fragmentation. (b) Annotated MS2 spectra of base-hydrolyzed telomycin B, including observed b- and y-ions resulting from amide bond cleavage.

Example 9

Structure Elucidation of Telomycin C (3)

(a) Structure of telomycin C elucidated by comparative NMR spectroscopy, HRMS, and MS/MS fragmentation. (b) Annotated MS2 spectra of base-hydrolyzed telomycin C, including observed b- and y-ions resulting from amide bond cleavage.

Example 10

Structure Elucidation of Telomycin D (4)

(a) Structure of telomycin D elucidated by comparative NMR spectroscopy, HRMS, and MS/MS fragmentation. (b) Annotated MS2 spectra of base-hydrolyzed telomycin D, including observed b- and y-ions resulting from amide bond cleavage.

Example 11

Structure Elucidation of Telomycin E (5)

(a) Structure of telomycin E elucidated by comparative NMR spectroscopy, HRMS, and MS/MS fragmentation. (b) Annotated MS2 spectra of base-hydrolyzed telomycin E, including observed b- and y-ions resulting from amide bond cleavage.

Example 12

Structure Elucidation of Telomycin F (6)

(a) Structure of telomycin F elucidated by comparative NMR spectroscopy, HRMS, and MS/MS fragmentation. (b) Annotated MS2 spectra of base-hydrolyzed telomycin F, including observed b- and y-ions resulting from amide bond cleavage.

Example 13

Structure Elucidation of Telomycin G (7)

(a) Structure of telomycin G elucidated by comparative NMR spectroscopy, HRMS, and MS/MS fragmentation (b) Annotated MS2 spectra of base-hydrolyzed telomycin G, including observed b- and y-ions resulting from amide bond cleavage.

Example 14

Structure Elucidation of Di-5-Methyltryptophan Telomycin (8)

(a) Structure of di-5-methyltryptophan telomycin elucidated by NMR spectroscopy, HRMS, and MS/MS fragmentation. (b) Annotated MS2 spectra of di-5-methyltryptophan telomycin, including observed b- and y-ions resulting from amide bond cleavage.

Example 15

Structure Elucidation of Di-5-Hydroxytryptophan Telomycin (9)

(a) Structure of di-5-hydroxytryptophan telomycin elucidated by HRMS and MS/MS fragmentation. (b) Annotated MS2 spectra of di-5-hydroxytryptophan telomycin, including observed b- and y-ions resulting from amide bond cleavage.

Example 16

Structure Elucidation of Di-5-Methoxytryptophan Telomycin (10)

(a) Structure of di-5-methoxytryptophan telomycin elucidated by HRMS and MS/MS fragmentation. (b) Annotated MS2 spectra of di-5-methoxytryptophan telomycin, including observed b- and y-ions resulting from amide bond cleavage.

It is to be understood that the above description it is intended to be illustrative, and not restrictive. Many other embodiments will be apparent to those skilled in the art, upon reviewing the above description. The scope of the invention should, therefore, be determined with reference to the appended claims, along with the full scope of equivalents to which such claims are entitled.

Although the present invention has been described with reference to specific exemplary embodiments, it will be evident that various modifications and changes may be made to these embodiments without departing from the broader spirit and scope of the disclosed subject matter as defined by the appended claims.

What is claimed is:

1. A computer-implemented method for identifying a first natural product of interest that is producible by an organism from a polynucleotide sequence resident in the organism, the method comprising automatically executing, using one or more digital processors of a computing platform, a bioinformatics tool for:
   (a) receiving as input into the bioinformatics tool the polynucleotide sequence to:
      (i) identify a given gene cluster defined within the polynucleotide sequence; and
      (ii) determine a set of gene cluster-encoded chemical monomers encoded by said given gene cluster;
   (b) aligning, using a molecular alignment engine in the bioinformatics tool, said set of gene cluster-encoded chemical monomers with a set of deconstructed chemical monomers determined by deconstruction of a plurality of known second natural products;
   (c) calculating a similarity score based on a computed molecular similarity between said gene cluster-encoded chemical monomers and said deconstructed chemical monomers, given said aligning, for each of the known second natural products, wherein said similarity score is based at least in part on a chemical structure most closely correlated to said given gene cluster;
   (d) associating a highest-scoring one of said known second natural products having a known molecular structure of interest with said given gene cluster manifesting a most similar chemical structure; and
   (e) directing, as an output, synthesis of the first natural product from said set of gene cluster-encoded chemical monomers encoded by said given gene cluster and investigation of the first natural product to determine that the first natural product is of interest for having chemical properties similar to that of said highest-scoring one of said second known natural products;
   wherein the bioinformatics tool defines a digital interface to receive as input the polynucleotide sequence and output said output.

2. The method of claim 1, wherein said similarity score is defined at least in part by a Tanimoto coefficient.

3. The method of claim 1, the method further comprising, prior to said aligning:
   comparing a predicted mass spectral signature predictably associated with said given gene cluster based on said set of gene cluster-encoded chemical monomers, with corresponding mass spectral signatures associated with multiple second known natural products; and selecting said plurality of known natural products as having a comparable mass spectral signature at least in part based on said comparing.

4. The method of claim 1, wherein:

said identifying comprises identifying a plurality of gene clusters defined within said polynucleotide sequence;

the method further comprises, prior to said aligning, comparing at least some of said identified gene clusters with a set of previously known gene clusters to identify a relatively unique one of said identified gene clusters; and said aligning, calculating and associating are executed, at least in part, in respect of said set of gene cluster-encoded chemical monomers associated with said relatively unique gene cluster.

5. The method of claim 4, wherein said comparing comprises:

respectively aligning said set of gene cluster-encoded chemical monomers associated with each of said identified gene clusters with a set of previously known gene cluster-encoded chemical monomers associated with said previously known gene clusters;

calculating respective similarity scores based on said aligning of gene cluster-encoded chemical monomers; and defining a set of gene cluster-encoded chemical monomers with the lowest similarity score as said unique gene cluster.

6. The method of claim 1, wherein said given gene cluster encodes for a ribosomally synthesized and/or post-translationally modified polypeptide (RiPP).

7. The method of claim 1, wherein said given gene cluster encodes for a nonribosomal peptide (NRP).

8. The method of claim 1, wherein said given gene cluster is derived from said polynucleotide sequence via Hidden Markov Modeling.

9. The method of claim 1, wherein said deconstructed chemical monomers are determined by a generalized retro-biosynthetic assembly prediction engine (GRAPE).

10. The method of claim 1, wherein said similarity score is calculated via a global alignment for natural products cheminformatics engine (GARLIC).

11. The method of claim 1, wherein said similarity score is computed via a Needleman and Wunsch method.

12. The computer-implemented method of claim 1, further comprising, based on said directing, synthesizing, and investigating the first natural product for manifesting similar chemical properties of interest.

13. A non-transitory computer readable medium having statements and instructions stored thereon to be executed by one or more digital processors of a computing platform to identify a first natural product of interest from a polynucleotide sequence by implementing the method of claim 1.

14. A computerized system for identifying a natural product of interest from a polynucleotide sequence, the system comprising:

a computer-readable medium as defined in claim 13;

said one or more digital processors; and said interface to receive as input the polynucleotide sequence and output said output;

wherein the interface is a network interface directly or indirectly interfacing over a data network with said one or more digital processors and said computer-readable medium.

15. The system of claim 14, wherein said network interface is a Web interface.

* * * * *